United States Patent
Novarino et al.

(10) Patent No.: US 11,441,251 B2
(45) Date of Patent: Sep. 13, 2022

(54) NONWOVEN FABRICS COMPRISING POLYLACTIC ACID HAVING IMPROVED STRENGTH AND TOUGHNESS

(71) Applicants: Fitesa Germany GmbH, Peine (DE); Fitesa Simpsonville, Inc., Simpsonville, SC (US)

(72) Inventors: Elena Novarino, Hannover (DE); Gary Drews, Greenville, SC (US); Jason Hamilton, Peine (DE); Stephen Chester, Simpsonville, SC (US); Alfredo Izzo, Peine (DE); David D. Newkirk, Greer, SC (US)

(73) Assignees: Fitesa Germany GmbH, Peine (DE); Fitesa Simpsonville, Inc., Simpsonville, SC (US)

(*) Notice: Subject to any disclaimer, the term of this patent is extended or adjusted under 35 U.S.C. 154(b) by 353 days.

(21) Appl. No.: 15/676,163

(22) Filed: Aug. 14, 2017

(65) Prior Publication Data
US 2018/0051404 A1    Feb. 22, 2018

Related U.S. Application Data

(60) Provisional application No. 62/375,648, filed on Aug. 16, 2016.

(51) Int. Cl.
*D04H 3/009* (2012.01)
*D04H 3/011* (2012.01)
(Continued)

(52) U.S. Cl.
CPC ....... *D04H 3/009* (2013.01); *A61F 13/15707* (2013.01); *A61F 13/51* (2013.01); *D01D 5/38* (2013.01); *D01D 7/00* (2013.01); *D01F 1/10* (2013.01); *D01F 6/625* (2013.01); *D01F 8/14* (2013.01); *D04H 3/011* (2013.01); *D04H 3/147* (2013.01); *D04H 3/16* (2013.01);
(Continued)

(58) Field of Classification Search
CPC ..................................................... D04H 3/009
See application file for complete search history.

(56) References Cited

U.S. PATENT DOCUMENTS 3,338,992 A    8/1967    Kinney
3,692,613 A    9/1972    Pederson
(Continued)

FOREIGN PATENT DOCUMENTS

EP    0 977 912 B1    2/2000
EP    1 432 860 A1    6/2004
(Continued)

OTHER PUBLICATIONS

"Pure Concentration: Sukano® as PLA S546-Q1"; Sukano Polymers Corporation; Revision Feb. 25, 2016; 1 page.
(Continued)

*Primary Examiner* — Andrew T Piziali
(74) *Attorney, Agent, or Firm* — Rimon, P.C.

(57) ABSTRACT

Nonwoven fabrics having a plurality of fibers that are bonded to each other to form a coherent web, wherein the fibers comprise a blend of a polylactic acid (PLA) and at least one secondary alkane sulfonate are provided. The nonwoven fabrics exhibit increased tensile strengths, elongation and toughness.

24 Claims, 8 Drawing Sheets

(51) Int. Cl.
  *D01F 8/14* (2006.01)
  *D01F 1/10* (2006.01)
  *D01F 6/62* (2006.01)
  *D04H 3/147* (2012.01)
  *A61F 13/15* (2006.01)
  *A61F 13/51* (2006.01)
  *D01D 5/38* (2006.01)
  *D01D 7/00* (2006.01)
  *D04H 3/16* (2006.01)
  *D01D 5/098* (2006.01)

(52) U.S. Cl.
  CPC ............... *A61F 2013/15959* (2013.01); *A61F 2013/51004* (2013.01); *A61F 2013/51028* (2013.01); *D01D 5/0985* (2013.01)

(56) References Cited

U.S. PATENT DOCUMENTS

| | | |
|---|---|---|
| 3,802,817 A | 4/1974 | Matsuki et al. |
| 3,849,241 A | 11/1974 | Butin et al. |
| 4,405,297 A | 9/1983 | Appel et al. |
| 4,789,592 A | 12/1988 | Taniguchi et al. |
| 4,795,668 A | 1/1989 | Krueger et al. |
| 5,057,368 A | 10/1991 | Largman et al. |
| 5,069,970 A | 12/1991 | Largman et al. |
| 5,108,820 A | 4/1992 | Kaneko et al. |
| 5,162,074 A | 11/1992 | Hills |
| 5,277,976 A | 1/1994 | Hogle et al. |
| 5,336,552 A | 8/1994 | Strack et al. |
| 5,344,297 A | 9/1994 | Hills |
| 5,382,400 A | 1/1995 | Pkie et al. |
| 5,466,410 A | 11/1995 | Hills |
| 5,525,706 A | 6/1996 | Gruber et al. |
| 5,575,874 A | 11/1996 | Griesbach, III et al. |
| 5,593,778 A * | 1/1997 | Kondo .................. C08G 63/60 264/239 |
| 5,665,300 A | 9/1997 | Brignola et al. |
| 5,814,349 A | 9/1998 | Geus et al. |
| 6,176,952 B1 | 1/2001 | Maugans et al. |
| 6,200,669 B1 | 3/2001 | Marmon et al. |
| 6,375,886 B1 | 4/2002 | Angadjivand et al. |
| 6,455,156 B1 | 9/2002 | Tanaka et al. |
| 6,500,540 B1 | 12/2002 | Langohr et al. |
| 6,506,873 B1 | 1/2003 | Ryan et al. |
| 6,517,648 B1 | 2/2003 | Bouchette et al. |
| 6,562,938 B2 | 5/2003 | Haile et al. |
| 6,646,178 B2 | 11/2003 | Furuya et al. |
| 6,710,135 B2 | 3/2004 | Tan et al. |
| 6,756,331 B2 | 6/2004 | Kasemura et al. |
| 6,759,356 B1 | 7/2004 | Myers |
| 6,787,613 B2 | 9/2004 | Bastioli et al. |
| 6,807,973 B2 | 10/2004 | Fratello et al. |
| 6,881,375 B2 | 4/2005 | Topolkaraev et al. |
| 6,890,872 B2 | 5/2005 | Bond et al. |
| 6,905,987 B2 | 6/2005 | Noda et al. |
| 7,014,803 B2 | 3/2006 | Perez et al. |
| 7,045,173 B2 | 5/2006 | Hirsch et al. |
| 7,083,697 B2 | 8/2006 | Dao et al. |
| 7,174,612 B2 | 2/2007 | Ortega et al. |
| 7,192,604 B2 | 3/2007 | Brown et al. |
| 7,314,840 B2 | 1/2008 | Baychar |
| 7,338,355 B2 | 3/2008 | Sanders, Jr. et al. |
| 7,390,760 B1 | 6/2008 | Chen et al. |
| 7,576,019 B2 | 8/2009 | Bond et al. |
| 7,582,694 B2 | 9/2009 | Jiang et al. |
| 7,601,659 B2 | 10/2009 | Bomberger et al. |
| 7,604,859 B2 | 10/2009 | Liu et al. |
| 7,622,188 B2 | 11/2009 | Kayiyama et al. |
| 7,628,829 B2 | 12/2009 | Woo et al. |
| 7,645,839 B2 | 1/2010 | Bastioli et al. |
| 7,660,040 B2 | 2/2010 | Starry et al. |
| 7,695,794 B2 | 4/2010 | Osterbroek et al. |
| 7,700,500 B2 | 4/2010 | Jordan et al. |
| 7,757,811 B2 | 7/2010 | Fox et al. |
| 7,767,297 B2 | 8/2010 | Tajima et al. |
| 7,779,521 B2 | 8/2010 | Topolkaraev et al. |
| 7,780,903 B2 | 8/2010 | Topolkaraev et al. |
| 7,799,708 B2 | 9/2010 | Francis et al. |
| 7,914,637 B2 | 3/2011 | Pedoja |
| 7,959,751 B2 | 6/2011 | Hanson et al. |
| 7,968,480 B2 | 6/2011 | Bishop et al. |
| 7,972,692 B2 | 7/2011 | Chakravarty et al. |
| 7,989,062 B2 | 8/2011 | Chakravarty et al. |
| 7,994,078 B2 | 8/2011 | Reichmann et al. |
| 7,998,889 B2 | 8/2011 | Stralin et al. |
| 8,021,996 B2 | 9/2011 | Walser et al. |
| 8,026,188 B2 | 9/2011 | Mor |
| 8,043,679 B2 | 10/2011 | Bastioli et al. |
| 8,101,253 B2 | 1/2012 | Bastioli et al. |
| 8,101,688 B2 | 1/2012 | Kimura et al. |
| 8,163,036 B1 | 4/2012 | Vempati et al. |
| 8,178,021 B2 | 5/2012 | Suzuki |
| 8,182,725 B2 | 5/2012 | Green et al. |
| 8,257,640 B2 | 9/2012 | Anneaux et al. |
| 8,268,738 B2 | 9/2012 | McEneany et al. |
| 8,287,983 B2 | 10/2012 | Emirze et al. |
| 8,349,232 B2 | 1/2013 | Pourdeyhimi et al. |
| 8,410,006 B2 | 4/2013 | Chappas et al. |
| 8,465,611 B2 | 6/2013 | Farell et al. |
| 8,512,844 B2 | 8/2013 | Dijkema et al. |
| 8,513,144 B2 | 8/2013 | Ting et al. |
| 8,518,311 B2 | 8/2013 | He et al. |
| 8,529,671 B2 | 9/2013 | Sebastian et al. |
| 8,530,557 B2 | 9/2013 | Noda et al. |
| 8,535,727 B2 | 9/2013 | Pourdeyhimi et al. |
| 8,551,378 B2 | 10/2013 | Velev et al. |
| 8,597,555 B2 | 12/2013 | Pedoja |
| 8,598,406 B2 | 12/2013 | Ponomarenko et al. |
| 8,636,942 B2 | 1/2014 | Komura et al. |
| 8,637,728 B2 | 1/2014 | Fingal et al. |
| 8,703,627 B2 | 4/2014 | Matsuda et al. |
| 8,709,591 B2 | 4/2014 | Sumi et al. |
| 8,721,943 B2 | 5/2014 | Moore et al. |
| 8,828,895 B2 | 9/2014 | Foss et al. |
| 8,835,709 B2 | 9/2014 | Isele et al. |
| 8,846,825 B2 | 9/2014 | Bastioli |
| 8,858,986 B2 | 10/2014 | Scholz et al. |
| 8,865,964 B2 | 10/2014 | Bellini et al. |
| 8,871,237 B2 | 10/2014 | Zussman et al. |
| 8,906,815 B2 | 12/2014 | Moore et al. |
| 8,926,877 B2 | 1/2015 | Melik et al. |
| 8,927,443 B2 | 1/2015 | Chakravarty et al. |
| 8,936,740 B2 | 1/2015 | Topolkaraev et al. |
| 8,974,890 B2 | 3/2015 | Mitsuno |
| 9,029,149 B2 | 5/2015 | Nain |
| 9,062,393 B2 | 6/2015 | Ito et al. |
| 9,080,258 B2 | 7/2015 | Cuculo et al. |
| 9,103,057 B2 | 8/2015 | Polosa et al. |
| 9,108,839 B2 | 8/2015 | Dijkema et al. |
| 9,156,980 B2 | 10/2015 | Bastioli |
| 9,194,065 B2 | 11/2015 | Moore et al. |
| 9,279,202 B2 | 3/2016 | Matsumura et al. |
| 9,290,868 B2 | 3/2016 | Iwata et al. |
| 9,382,643 B2 | 7/2016 | Moore et al. |
| 9,452,239 B2 | 9/2016 | West et al. |
| 9,475,034 B2 | 10/2016 | Vincent et al. |
| 9,498,742 B2 | 11/2016 | Hosoya et al. |
| 9,511,528 B2 | 12/2016 | Wong et al. |
| 9,539,357 B2 | 1/2017 | Ashraf et al. |
| 9,540,746 B2 | 1/2017 | Ashraf et al. |
| 9,546,440 B2 | 1/2017 | Mitsuno et al. |
| 9,555,167 B2 | 1/2017 | Schmid et al. |
| 9,580,845 B2 | 2/2017 | Ashraf |
| 9,604,168 B2 | 3/2017 | Menkhaus et al. |
| 9,611,572 B2 | 4/2017 | Moore et al. |
| 2003/0041953 A1 | 3/2003 | Farell et al. |
| 2005/0082723 A1 | 4/2005 | Brock et al. |
| 2005/0087288 A1 | 4/2005 | Haynes et al. |
| 2006/0046593 A1 | 3/2006 | Senellart et al. |
| 2008/0176475 A1 | 7/2008 | Sahasrabudhe et al. |
| 2011/0306260 A1 | 12/2011 | Katsuya |
| 2012/0040185 A1 | 2/2012 | Topolkaraev et al. |

(56) References Cited

U.S. PATENT DOCUMENTS

| | | |
|---|---|---|
| 2012/0077886 A1 | 3/2012 | Scholz et al. |
| 2012/0149273 A1 | 6/2012 | Moore et al. |
| 2012/0164401 A1 | 6/2012 | Vieth et al. |
| 2012/0184166 A1 | 7/2012 | Kurihara et al. |
| 2012/0220680 A1 | 8/2012 | Bastioli et al. |
| 2012/0329352 A1 | 12/2012 | Yoshida et al. |
| 2013/0037481 A1 | 2/2013 | Lalouch et al. |
| 2013/0053479 A1 | 2/2013 | Bond et al. |
| 2013/0072889 A1 | 3/2013 | Yang |
| 2013/0072891 A1 | 3/2013 | Fung |
| 2013/0101805 A1 | 4/2013 | Altshuler et al. |
| 2013/0108097 A1 | 5/2013 | Neilson et al. |
| 2013/0108831 A1 | 5/2013 | Wu et al. |
| 2013/0190408 A1* | 7/2013 | Scholz .................. A61L 15/26 514/772.3 |
| 2013/0210308 A1 | 8/2013 | McEneany et al. |
| 2013/0252500 A1 | 9/2013 | Bradley et al. |
| 2013/0309932 A1 | 11/2013 | He et al. |
| 2013/0316608 A1 | 11/2013 | Lin et al. |
| 2013/0337710 A1 | 12/2013 | Rocafort et al. |
| 2014/0038487 A1 | 2/2014 | Polosa et al. |
| 2014/0045397 A1 | 2/2014 | Stachnik et al. |
| 2014/0080968 A1 | 3/2014 | Quintana et al. |
| 2014/0120322 A1 | 5/2014 | Fu et al. |
| 2014/0170922 A1 | 6/2014 | Poruthoor et al. |
| 2014/0242309 A1 | 8/2014 | Foss et al. |
| 2014/0263033 A1 | 9/2014 | Fu et al. |
| 2014/0272360 A1 | 9/2014 | Yang |
| 2014/0272362 A1 | 9/2014 | Dugan et al. |
| 2014/0276517 A1 | 9/2014 | Chester et al. |
| 2014/0277572 A1 | 9/2014 | Martin et al. |
| 2014/0300024 A1 | 10/2014 | Takeda et al. |
| 2015/0017866 A1 | 1/2015 | Schroer et al. |
| 2015/0044924 A1 | 2/2015 | Yi et al. |
| 2015/0056471 A1 | 2/2015 | Joo et al. |
| 2015/0056880 A1 | 2/2015 | Lee et al. |
| 2015/0086760 A1 | 3/2015 | Castillo |
| 2015/0111019 A1 | 4/2015 | Huang et al. |
| 2015/0126091 A1 | 5/2015 | Kamann et al. |
| 2015/0136693 A1 | 5/2015 | Hwang et al. |
| 2015/0247271 A1 | 9/2015 | Fung |
| 2015/0265746 A1 | 9/2015 | Martin et al. |
| 2015/0283285 A1 | 10/2015 | Karls et al. |
| 2015/0290354 A1 | 10/2015 | Loboa et al. |
| 2015/0322604 A1 | 11/2015 | Brunner et al. |
| 2015/0322606 A1 | 11/2015 | Stralin et al. |
| 2015/0330004 A1 | 11/2015 | Stralin et al. |
| 2015/0343455 A1 | 12/2015 | Schultz et al. |
| 2016/0008519 A1 | 1/2016 | Gonzalez Padilla et al. |
| 2016/0038645 A1 | 2/2016 | Pereira Matrins et al. |
| 2016/0066620 A1 | 3/2016 | Atchley et al. |
| 2016/0073689 A1 | 3/2016 | Sebastian et al. |
| 2016/0108564 A1 | 4/2016 | Topolkaraev et al. |
| 2016/0115630 A1 | 4/2016 | Kubota et al. |
| 2016/0145780 A1 | 5/2016 | Chou et al. |
| 2016/0145781 A1 | 5/2016 | Chou et al. |
| 2016/0151213 A1 | 6/2016 | Bauduin et al. |
| 2016/0206984 A1 | 7/2016 | Berrigan et al. |
| 2016/0243788 A1 | 8/2016 | Steiner et al. |
| 2016/0298266 A1 | 10/2016 | Zillig et al. |
| 2016/0333509 A1 | 11/2016 | Novarino et al. |
| 2017/0007950 A1 | 1/2017 | Tong et al. |
| 2017/0022642 A1 | 1/2017 | Pan |
| 2017/0056253 A1 | 3/2017 | Chester et al. |
| 2017/0058510 A1 | 3/2017 | Seabaugh et al. |
| 2017/0071607 A1 | 3/2017 | Johnson et al. |
| 2017/0072430 A1 | 3/2017 | Maier et al. |
| 2017/0073515 A1 | 3/2017 | Wong et al. |
| 2017/0102372 A1 | 4/2017 | Zussman et al. |
| 2017/0107651 A1 | 4/2017 | Zhao et al. |
| 2017/0121860 A1 | 5/2017 | Dahringer et al. |
| 2017/0121872 A1 | 5/2017 | Ashraf |
| 2017/0173916 A1 | 6/2017 | Widenbrant et al. |

FOREIGN PATENT DOCUMENTS

| | | |
|---|---|---|
| EP | 1 355 985 B1 | 8/2004 |
| EP | 1 280 948 B1 | 10/2004 |
| EP | 1 057 844 B1 | 12/2004 |
| EP | 1 215 225 B9 | 3/2005 |
| EP | 1 082 479 B1 | 5/2005 |
| EP | 1 432 860 B1 | 9/2005 |
| EP | 1 000 102 B1 | 11/2005 |
| EP | 1 227 129 B1 | 9/2006 |
| EP | 1 460 096 B1 | 11/2006 |
| EP | 1 345 635 B1 | 1/2007 |
| EP | 1 756 368 A1 | 2/2007 |
| EP | 1 418 201 B1 | 8/2007 |
| EP | 1 575 390 B1 | 3/2008 |
| EP | 1 260 533 B1 | 5/2008 |
| EP | 1 360 235 B1 | 5/2008 |
| EP | 1 838 784 B1 | 6/2008 |
| EP | 1 257 703 B1 | 7/2008 |
| EP | 1 283 285 B1 | 9/2008 |
| EP | 2 001 956 A2 | 12/2008 |
| EP | 1 630 265 B1 | 2/2009 |
| EP | 1 130 149 B1 | 6/2009 |
| EP | 1 979 412 B1 | 6/2009 |
| EP | 2 050 850 B1 | 6/2009 |
| EP | 2 066 834 A1 | 6/2009 |
| EP | 2 076 382 A1 | 7/2009 |
| EP | 1 537 260 B1 | 11/2009 |
| EP | 1 493 555 B1 | 12/2009 |
| EP | 1 947 145 B1 | 12/2009 |
| EP | 1 986 583 B1 | 12/2009 |
| EP | 2 044 260 B1 | 2/2010 |
| EP | 2 074 176 B1 | 5/2010 |
| EP | 1 525 008 B1 | 6/2010 |
| EP | 1 548 161 B1 | 8/2010 |
| EP | 1 731 634 B1 | 8/2010 |
| EP | 1 184 020 B1 | 9/2010 |
| EP | 1 966 419 B1 | 9/2010 |
| EP | 1 998 731 B1 | 9/2010 |
| EP | 1 094 755 B1 | 12/2010 |
| EP | 2 150 646 B1 | 12/2010 |
| EP | 1 264 860 B1 | 2/2011 |
| EP | 2 291 285 A1 | 3/2011 |
| EP | 1 944 395 B1 | 4/2011 |
| EP | 1 397 535 B1 | 6/2011 |
| EP | 1 458 915 B1 | 7/2011 |
| EP | 1 579 048 B1 | 7/2011 |
| EP | 1 993 621 B1 | 8/2011 |
| EP | 2 126 166 B1 | 9/2011 |
| EP | 2 167 712 B1 | 10/2011 |
| EP | 2 004 396 B1 | 11/2011 |
| EP | 2 051 607 B1 | 11/2011 |
| EP | 2 201 162 B1 | 11/2011 |
| EP | 2 041 346 B1 | 12/2011 |
| EP | 1 966 423 B1 | 1/2012 |
| EP | 2 401 429 B1 | 1/2012 |
| EP | 1 532 299 B1 | 2/2012 |
| EP | 2 173 931 B1 | 2/2012 |
| EP | 2 203 511 B1 | 2/2012 |
| EP | 1 766 121 B1 | 3/2012 |
| EP | 1 861 524 B1 | 4/2012 |
| EP | 1 889 900 B1 | 4/2012 |
| EP | 1 885 923 B1 | 6/2012 |
| EP | 2 098 565 B1 | 6/2012 |
| EP | 2 467 516 A2 | 6/2012 |
| EP | 1 842 944 B9 | 7/2012 |
| EP | 1 885 922 B1 | 7/2012 |
| EP | 1 991 287 B1 | 7/2012 |
| EP | 2 261 410 B1 | 7/2012 |
| EP | 1 381 720 B1 | 9/2012 |
| EP | 1 874 991 B1 | 10/2012 |
| EP | 2 512 607 A1 | 10/2012 |
| EP | 2 512 802 A1 | 10/2012 |
| EP | 2 272 886 B1 | 11/2012 |
| EP | 1 988 202 B1 | 12/2012 |
| EP | 2 182 890 B1 | 12/2012 |
| EP | 1 953 191 B1 | 5/2013 |
| EP | 2 140 048 B1 | 5/2013 |
| EP | 2 331 854 B1 | 6/2013 |

(56) References Cited

FOREIGN PATENT DOCUMENTS

| | | |
|---|---|---|
| EP | 1 771 612 B1 | 7/2013 |
| EP | 2 190 923 B1 | 7/2013 |
| EP | 2 431 512 B1 | 7/2013 |
| EP | 2 456 585 B1 | 7/2013 |
| EP | 2 532 775 B1 | 7/2013 |
| EP | 2 627 810 A1 | 8/2013 |
| EP | 1 846 611 B1 | 9/2013 |
| EP | 2 185 120 B1 | 10/2013 |
| EP | 2 301 743 B1 | 10/2013 |
| EP | 2 411 221 B1 | 10/2013 |
| EP | 2 456 399 B1 | 10/2013 |
| EP | 1 702 001 B1 | 11/2013 |
| EP | 2 422 005 B1 | 12/2013 |
| EP | 1 660 323 B2 | 1/2014 |
| EP | 2 122 021 B1 | 1/2014 |
| EP | 2 237 754 B1 | 1/2014 |
| EP | 2 515 689 B1 | 2/2014 |
| EP | 2 691 458 A1 | 2/2014 |
| EP | 2 692 923 A1 | 2/2014 |
| EP | 2 692 924 A1 | 2/2014 |
| EP | 2 103 723 B1 | 3/2014 |
| EP | 2 281 080 B1 | 3/2014 |
| EP | 2 572 691 B1 | 4/2014 |
| EP | 1 604 622 B1 | 5/2014 |
| EP | 2 572 690 B1 | 5/2014 |
| EP | 2 664 702 B1 | 6/2014 |
| EP | 2 276 789 B1 | 7/2014 |
| EP | 2 222 466 B1 | 8/2014 |
| EP | 2 561 130 B1 | 8/2014 |
| EP | 2 311 360 B1 | 9/2014 |
| EP | 2 582 866 B1 | 9/2014 |
| EP | 1 771 613 B1 | 10/2014 |
| EP | 2 231 912 B1 | 10/2014 |
| EP | 2 376 693 B1 | 10/2014 |
| EP | 2 436 814 B1 | 10/2014 |
| EP | 2 115 200 B1 | 11/2014 |
| EP | 2 152 217 B1 | 11/2014 |
| EP | 2 411 061 B1 | 11/2014 |
| EP | 2 571 466 B1 | 12/2014 |
| EP | 2 582 875 B1 | 12/2014 |
| EP | 2 561 127 B1 | 1/2015 |
| EP | 2 561 128 B1 | 1/2015 |
| EP | 2 826 895 A1 | 1/2015 |
| EP | 2 826 897 A1 | 1/2015 |
| EP | 1 689 923 B1 | 2/2015 |
| EP | 1 802 358 B1 | 2/2015 |
| EP | 2 479 320 B1 | 2/2015 |
| EP | 2 470 136 B1 | 3/2015 |
| EP | 2 844 791 A1 | 3/2015 |
| EP | 2 401 317 B1 | 4/2015 |
| EP | 2 446 075 B1 | 4/2015 |
| EP | 2 247 448 B1 | 5/2015 |
| EP | 2 885 449 A1 | 6/2015 |
| EP | 2 496 768 B1 | 7/2015 |
| EP | 2 648 669 B1 | 7/2015 |
| EP | 2 899 016 A1 | 7/2015 |
| EP | 2 101 572 B1 | 8/2015 |
| EP | 2 266 791 B1 | 8/2015 |
| EP | 2 906 161 A1 | 8/2015 |
| EP | 2 907 387 A1 | 8/2015 |
| EP | 2 559 794 B1 | 9/2015 |
| EP | 2 918 709 A1 | 9/2015 |
| EP | 2 473 348 B1 | 10/2015 |
| EP | 2 935 667 A1 | 10/2015 |
| EP | 2 345 430 B1 | 11/2015 |
| EP | 2 473 660 B1 | 11/2015 |
| EP | 2 627 813 B1 | 11/2015 |
| EP | 2 235 245 B1 | 12/2015 |
| EP | 2 301 403 B1 | 1/2016 |
| EP | 2 305 862 B1 | 1/2016 |
| EP | 2 450 487 B1 | 1/2016 |
| EP | 2 784 114 B1 | 1/2016 |
| EP | 1 070 097 B1 | 2/2016 |
| EP | 2 297 212 B1 | 2/2016 |
| EP | 2 539 496 B1 | 2/2016 |
| EP | 2 311 359 B1 | 4/2016 |
| EP | 2 619 269 B1 | 4/2016 |
| EP | 2 573 242 B1 | 5/2016 |
| EP | 2 496 631 B1 | 6/2016 |
| EP | 2 496 769 B1 | 6/2016 |
| EP | 2 781 636 B1 | 6/2016 |
| EP | 2 496 644 B1 | 7/2016 |
| EP | 2 841 263 B1 | 7/2016 |
| EP | 2 125 953 B1 | 8/2016 |
| EP | 2 429 681 B1 | 8/2016 |
| EP | 2 812 469 B1 | 8/2016 |
| EP | 2 496 630 B1 | 9/2016 |
| EP | 2 497 797 B1 | 9/2016 |
| EP | 2 847 382 B1 | 11/2016 |
| EP | 2 847 383 B1 | 11/2016 |
| EP | 2 331 634 B1 | 12/2016 |
| EP | 3 107 660 A1 | 12/2016 |
| EP | 3 107 712 A2 | 12/2016 |
| EP | 3 108 076 A1 | 12/2016 |
| EP | 3 119 930 A1 | 1/2017 |
| EP | 3 124 665 B1 | 2/2017 |
| EP | 3 129 530 A1 | 2/2017 |
| EP | 3 130 704 A1 | 2/2017 |
| EP | 1 981 557 B1 | 3/2017 |
| EP | 2 282 884 B1 | 3/2017 |
| EP | 3 071 639 B1 | 3/2017 |
| EP | 2 118 028 B1 | 4/2017 |
| EP | 2 605 736 B1 | 4/2017 |
| EP | 2 630 165 B1 | 4/2017 |
| EP | 3 156 229 A1 | 4/2017 |
| EP | 2 481 771 B1 | 5/2017 |
| EP | 2 608 957 B1 | 5/2017 |
| EP | 1 591 132 B1 | 6/2017 |
| EP | 2 326 359 B1 | 6/2017 |
| EP | 2 847 384 B1 | 6/2017 |
| EP | 2 167 005 B1 | 7/2017 |
| EP | 2 291 558 B1 | 7/2017 |
| EP | 2 826 817 B1 | 7/2017 |
| EP | 2 934 413 B1 | 7/2017 |
| EP | 2 995 321 B1 | 7/2017 |
| EP | 3 196 144 A2 | 7/2017 |
| EP | 2 681 355 B1 | 8/2017 |
| EP | 2 913 429 B1 | 8/2017 |
| EP | 2 930 260 B1 | 8/2017 |
| EP | 2 933 294 B9 | 8/2017 |
| EP | 3 210 584 | 8/2017 |
| EP | 2 183 420 B1 | 9/2017 |
| EP | 3 216 433 A1 | 9/2017 |
| EP | 3 216 435 A1 | 9/2017 |
| EP | 2 984 138 B1 | 10/2017 |
| JP | 2010516914 A | 5/2010 |
| JP | 201596617 A | 10/2010 |
| JP | 2011524202 A | 9/2011 |
| JP | 2013520583 A | 6/2013 |
| JP | 2015510555 A | 4/2015 |
| JP | 2016536474 A | 11/2016 |
| WO | WO 2004/025004 A1 | 3/2004 |
| WO | WO 2005/124028 A1 | 12/2005 |
| WO | WO 2007/030494 A2 | 3/2007 |
| WO | WO 2007/047263 A1 | 4/2007 |
| WO | WO 2007/095214 A2 | 8/2007 |
| WO | WO 2007/115081 A2 | 10/2007 |
| WO | WO 2007/128466 A1 | 11/2007 |
| WO | WO 2008/049142 A1 | 5/2008 |
| WO | WO 2008/082872 A1 | 7/2008 |
| WO | WO 2008/117805 A1 | 10/2008 |
| WO | WO 2009/041518 A1 | 4/2009 |
| WO | WO 2009/152345 A1 | 12/2009 |
| WO | WO 2010/073149 A2 | 7/2010 |
| WO | WO 2010/077929 A1 | 7/2010 |
| WO | WO 2010/117612 A2 | 10/2010 |
| WO | WO 2010/146240 A2 | 12/2010 |
| WO | WO 2011/031558 A2 | 3/2011 |
| WO | WO 2011/106205 A2 | 9/2011 |
| WO | WO 2011/155731 A2 | 12/2011 |
| WO | WO 2011/163393 A2 | 12/2011 |
| WO | WO 2012/020336 A2 | 2/2012 |
| WO | WO 2012/027539 A2 | 3/2012 |
| WO | WO 2012/047511 A1 | 4/2012 |

(56) References Cited

FOREIGN PATENT DOCUMENTS

| | | |
|---|---|---|
| WO | WO 2012/051479 A1 | 4/2012 |
| WO | WO 2012/082517 A2 | 6/2012 |
| WO | WO 2012/118090 A1 | 9/2012 |
| WO | WO 2012/138552 A2 | 10/2012 |
| WO | WO 2012/145143 A2 | 10/2012 |
| WO | WO 2012/158403 A2 | 11/2012 |
| WO | WO 2012/175979 A1 | 12/2012 |
| WO | WO 2013/015735 A1 | 1/2013 |
| WO | WO 2013/022347 A1 | 2/2013 |
| WO | WO 2013/036848 A1 | 3/2013 |
| WO | WO 2013/056978 A2 | 4/2013 |
| WO | WO 2013/090652 A1 | 6/2013 |
| WO | WO 2013/118009 A1 | 8/2013 |
| WO | WO 2013/118019 A2 | 8/2013 |
| WO | WO 2013/135926 A1 | 9/2013 |
| WO | WO 2013/150528 A2 | 10/2013 |
| WO | WO 2013/188674 A1 | 12/2013 |
| WO | WO 2014/001340 A1 | 1/2014 |
| WO | WO 2014/027906 A1 | 2/2014 |
| WO | WO 2014/104955 A1 | 7/2014 |
| WO | WO 2014/104956 A1 | 7/2014 |
| WO | WO 2014/124564 A1 | 8/2014 |
| WO | WO 2014/138588 A1 | 9/2014 |
| WO | WO 2014/138898 A1 | 9/2014 |
| WO | WO 2014/145312 A2 | 9/2014 |
| WO | WO 2014/170348 A1 | 10/2014 |
| WO | WO 2014/192976 A1 | 12/2014 |
| WO | WO 2014/199274 A1 | 12/2014 |
| WO | WO 2014/202481 A1 | 12/2014 |
| WO | WO 2014/209698 A1 | 12/2014 |
| WO | WO 2015/006566 A1 | 1/2015 |
| WO | WO 2015/009707 A1 | 1/2015 |
| WO | WO 2015/034799 A1 | 3/2015 |
| WO | WO 2015/047806 A1 | 4/2015 |
| WO | WO 2015/047890 A1 | 4/2015 |
| WO | WO 2015/047924 A1 | 4/2015 |
| WO | WO 2015/047987 A1 | 4/2015 |
| WO | WO 2015/047988 A1 | 4/2015 |
| WO | WO 2015/049027 A1 | 4/2015 |
| WO | WO 2015/055177 A1 | 4/2015 |
| WO | WO 2015/066299 A1 | 5/2015 |
| WO | WO 2015/066300 A1 | 5/2015 |
| WO | WO 2015/080913 A1 | 6/2015 |
| WO | WO 2015/112844 A1 | 7/2015 |
| WO | WO 2015/114126 A1 | 8/2015 |
| WO | WO 2015/124242 A1 | 8/2015 |
| WO | WO 2015/126645 A1 | 8/2015 |
| WO | WO 2015/155182 A1 | 10/2015 |
| WO | WO 2015/160027 A1 | 10/2015 |
| WO | WO 2015/164447 A2 | 10/2015 |
| WO | WO 2015/165919 A1 | 11/2015 |
| WO | WO 2015/169257 A1 | 11/2015 |
| WO | WO 2015/176063 A1 | 11/2015 |
| WO | WO 2015/183354 A2 | 12/2015 |
| WO | WO 2015/191229 A1 | 12/2015 |
| WO | WO 2015/191493 A1 | 12/2015 |
| WO | WO 2015/199998 A1 | 12/2015 |
| WO | WO 2016/000968 A1 | 1/2016 |
| WO | WO 2016/010297 A1 | 1/2016 |
| WO | WO 2016/010302 A1 | 1/2016 |
| WO | WO 2016/010303 A1 | 1/2016 |
| WO | WO 2016/018965 A2 | 2/2016 |
| WO | WO 2016/020236 A1 | 2/2016 |
| WO | WO 2016/028840 A1 | 2/2016 |
| WO | WO 2016/033097 A1 | 3/2016 |
| WO | WO 2016/066640 A1 | 5/2016 |
| WO | WO 2016/079724 A2 | 5/2016 |
| WO | WO 2016/094779 A1 | 6/2016 |
| WO | WO 2016/106273 A1 | 6/2016 |
| WO | WO 2016/114564 A2 | 7/2016 |
| WO | WO 2016/179384 A1 | 11/2016 |
| WO | WO 2016/187435 A2 | 11/2016 |
| WO | WO 2016/199079 A1 | 12/2016 |
| WO | WO 2016/199139 A1 | 12/2016 |
| WO | WO 2016/200923 A1 | 12/2016 |
| WO | WO 2016/206659 A1 | 12/2016 |
| WO | WO 2016/207444 A1 | 12/2016 |
| WO | WO 2017/007842 A1 | 1/2017 |
| WO | WO 2017/015477 A1 | 1/2017 |
| WO | WO 2017/025271 A1 | 2/2017 |
| WO | WO 2017/037550 A1 | 3/2017 |
| WO | WO 2017/042290 A1 | 3/2017 |
| WO | WO 2017/042362 A1 | 3/2017 |
| WO | WO 2017/048553 A1 | 3/2017 |
| WO | WO 2017/052442 A1 | 3/2017 |
| WO | WO 2017/059834 A1 | 4/2017 |
| WO | WO 2017/063680 A1 | 4/2017 |
| WO | WO 2017/066432 A1 | 4/2017 |
| WO | WO 2017/086851 A1 | 5/2017 |
| WO | WO 2017/099169 A1 | 6/2017 |
| WO | WO 2017/101974 A1 | 6/2017 |
| WO | WO 2017/103261 A1 | 6/2017 |
| WO | WO 2017/106191 A1 | 6/2017 |
| WO | WO 2017/112756 A1 | 6/2017 |
| WO | WO 2017/124092 A1 | 7/2017 |
| WO | WO 2017/165889 A2 | 9/2017 |
| WO | WO 2017/134171 A1 | 8/2018 |

OTHER PUBLICATIONS

Bhat, G.S et al.; "Development structure and properties during thermal calendaring of polylactic acid (PLA)"; eXPRESS Polymer Letters; vol. 2, No. 1; (2008) 49-56.

International Search Report and Written Opinion for corresponding International Application No. PCT/IB2017/054741, dated Nov. 21, 2017, 14 pages.

International Search Report and Written Opinion for corresponding International Application No. PCT/IB2017/054971, dated Nov. 21, 2017, 16 pages.

Primer on Antistatic Masterbatches [online] [retrieved Sep. 27, 2017]. Retrieved from the Internet: <URL:http://www.ampacet.com/faqs/antistatic-masterbatches/>. 3 pages.

Static Control in Converting [online] [retrieved Sep. 27, 2017]. Retrieved from the Internet: <URL:http://www.electrostaticanswers.com/Publications/2009_Robinson_AIMCAL_PFFC_Webinar_Handout-Static_Control_in_Converting.pdf>. (dated Jun. 11, 2009) 11 pages.

Office Action for corresponding European Application No. 17768511.2 dated Feb. 15, 2019, 54 pages.

Japanese Office Action, Application No. 2019-505153, dated Feb. 12, 2020.

Office Action for U.S. Appl. No. 15/666,675 dated Jan. 11, 2019, 11 pages.

* cited by examiner

NONWOVEN FABRICS COMPRISING POLYLACTIC ACID HAVING IMPROVED STRENGTH AND TOUGHNESS

FIELD

The presently-disclosed invention relates generally to nonwoven fabrics, and more particularly to nonwoven fabrics comprising polylactic acid (PLA).

BACKGROUND

Nonwoven fabrics are used in a variety of applications such as garments, disposable medical products, diapers, personal hygiene products, among others. New products being developed for these applications have demanding performance requirements, including comfort, conformability to the body, freedom of body movement, good softness and drape, adequate tensile strength and durability, and resistance to surface abrasion, pilling or fuzzing. Accordingly, the nonwoven fabrics which are used in these types of products must be engineered to meet these performance requirements.

Traditionally, such nonwoven fabrics are prepared from thermoplastic polymers, such as polyester, polystyrene, polyethylene, and polypropylene. These polymers are generally very stable and can remain in the environment for a long time. Recently, however, there has been a trend to develop articles and products that are considered environmentally friendly and sustainable. As part of this trend, there has been a desire to produce ecologically friendly products comprised of increased sustainable content in order to reduce the content of petroleum based materials.

Polylactic acid or polylactide-based polymers (PLA) provide a cost-effective path to sustainable content spunbond nonwovens that can be readily converted into consumer products. To fully capture the cost-effective benefits of PLA-based consumer products, PLA must be convertible into nonwovens and then into the final consumer product at very high speeds with minimal waste. However, due to the propensity of static generation and accumulation on fibers with PLA polymer on the surface, it is difficult to combine the steps of spinning, web formation, and bonding at the very high speeds needed for the economically attractive production of spunbond PLA with optimum fabric properties.

To address this need, nonwovens have been developed having a sheath/core bicomponent structure in which the PLA is present in the core, and a synthetic polymer, such as polypropylene, is in the sheath. An example of such a nonwoven fabric is described in U.S. Pat. No. 6,506,873. The presence of the synthetic polymer in the sheath provides the necessary properties for commercial production of nonwovens comprising PLA at high speeds. Although commercial production of nonwovens comprising PLA with synthetic polymers in the sheath is possible, the industry (and its consumers) are seeking nonwovens having PLA on the surface of the fabric by either having PLA in the sheath or being 100% PLA.

Accordingly, there still exists a need for fabrics having PLA that exhibit improved mechanical properties.

SUMMARY

One or more embodiments of the invention may address one or more of the aforementioned problems. Certain embodiments according to the invention provide polylactic acid (PLA) spunbond nonwoven fabrics, sustainable composites including said fabrics, and sustainable articles including said fabrics and/or composites. In particular, embodiments of the invention are directed to fabrics, composites, and articles comprising PLA.

Certain embodiments according to the invention are directed to a spunbond nonwoven fabric comprising a plurality of fibers that are bonded to each other to form a coherent web, wherein the fibers comprise a blend of a polylactic acid (PLA) and at least one secondary alkane sulfonate. In some embodiments, the blend is present at a surface of the plurality of fibers.

In one embodiment, the at least one secondary alkane sulfonate comprises an alkane chain having from $C_{10}$-$C_{18}$, and wherein at least one of the secondary carbons of the alkane chain includes a sulfonate moiety. For example, the at least one secondary alkane sulfonate has one of the following structures:

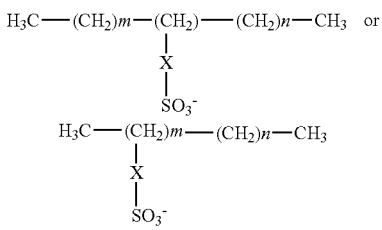

wherein m+n is a number between 7 and 16, and X is independently a $C_1$-$C_4$ alkyl or absent. In some embodiments, the at least one secondary alkane sulfonate has the following structure:

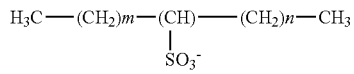

wherein m+n is a number between 8 and 15, and in particular, wherein m+n is a number between 11 and 14. In some embodiments, the at least one secondary alkane sulfonate comprises a salt of sodium or potassium.

In certain embodiments, the at least one secondary alkane sulfonate is present in an amount ranging from about 0.0125 to 2.5 weight percent, based on the total weight of the fiber. For example, the fiber may have a sheath/core bicomponent arrangement in which the blend is present in the sheath, and wherein the secondary alkane sulfonate is present in the sheath in an amount ranging from about 0.1 to 0.75 weight percent, based on the total weight of the sheath. In another embodiment, the fiber may have a sheath/core bicomponent arrangement in which the blend is present in the sheath, and wherein the secondary alkane sulfonate is present in the sheath in an amount ranging from about 0.2 to 0.6 weight percent, based on the total weight of the sheath. In yet another embodiment, the fiber has a sheath/core bicomponent arrangement in which the blend is present in the sheath, and wherein the secondary alkane sulfonate is present in the sheath in an amount ranging from about 0.3 to 0.4 weight percent, based on the total weight of the sheath.

In one embodiment, the plurality of fibers comprise bicomponent fibers. In some embodiments, the plurality of fibers comprise bicomponent fibers and the at least one secondary alkane sulfonate is present in only one of the component of the fibers. In one embodiment, the bicomponent fibers have a sheath/core configuration and the sheath comprises a blend of the PLA and the at least one secondary alkane sulfonate. In some embodiments, the core comprises PLA and does not include the at least one secondary alkane sulfonate. In still other embodiments, the bicomponent fibers comprise a side-by-side arrangement.

In one embodiment, the core comprises at least one of a polyolefin, a polyester, a PLA, or any combination thereof. In a preferred embodiment, each of the sheath and the core comprises PLA. In certain embodiments, the sheath comprises a first PLA grade, the core comprises a second PLA grade, and the first PLA grade and the second PLA grade are different.

Surprisingly, the inventors have discovered that the addition of the secondary alkane sulfonate to the PLA resin improves the mechanical properties of the fabric. In particular, the fabric may exhibit an increase in tensile strength, elongation and toughness in at least one of the machine direction or cross direction in comparison to an identical fabric that does not include the at least one secondary alkane sulfonate. For example, the fabric may exhibit an increase in tensile strength in at least one of the machine direction or cross direction of at least 50% in comparison to an identical fabric that does not include the at least one secondary alkane sulfonate.

In yet another aspect, embodiments of the invention are directed to a spunbond nonwoven fabric comprising a plurality of fibers that are bonded to each other to form a coherent web, wherein the fibers comprise from 95 to 100% polylactic acid (PLA), and wherein the fibers exhibit a root mean square of a Toughness Index per basis weight having a value that is at least 55 $N/m^2$. In one embodiment, the fabric has a root mean square of the Toughness Index per basis weight is a value that is greater than 65 $N\text{-}\%/g/m^2$, such as a value that is greater than 85 $N\text{-}\%/g/m^2$. In a preferred embodiment, the fabric has a root mean square of the Toughness Index per basis weight is a value from about from about 65 to 150 $N\text{-}\%/g/m^2$. Preferably, the fabric comprises fibers having less than 5 weight % of additives, and more preferably less than 4 weight %, based on the total weight of the fabric.

Additional aspects of the invention are directed to articles comprising the nonwoven fabric and to a process and system for preparing the fabric.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION

Figure 1A:
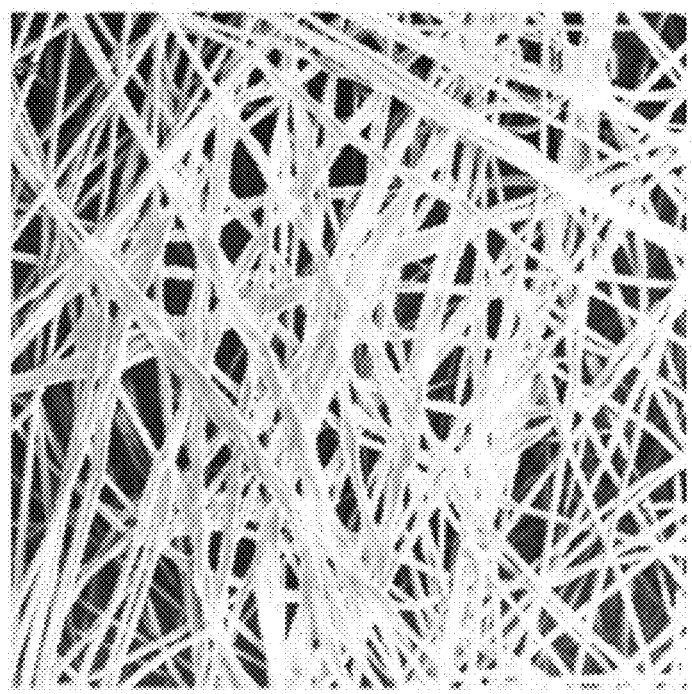
FIGS. 1A and 1B are SEM images of individual bond points on a surface of a nonwoven fabric that does not include a secondary alkane sulfonate.

The invention now will be described more fully hereinafter with reference to the accompanying drawings, in which some, but not all embodiments of the inventions are shown. Indeed, this inventions may be embodied in many different forms and should not be construed as limited to the embodiments set forth herein; rather, these embodiments are provided so that this disclosure will satisfy applicable legal requirements. Like numbers refer to like elements throughout. As used in the specification, and in the appended claims, the singular forms "a", "an", "the", include plural referents unless the context clearly dictates otherwise.

The invention includes, according to certain embodiments, polylactic acid (PLA) spunbond nonwoven fabrics, sustainable composites including said fabrics, and absorbent articles including said fabrics and/or composites. In particular, embodiments of the invention are directed to fabrics, composites, and articles in which PLA is present on the fabric surface.

PLA spunbond nonwoven fabrics and sustainable composites including said fabrics may be used in a wide variety of applications, including diapers, feminine care products, wiper products, incontinence products, agricultural products (e.g., root wraps, seed bags, crop covers and/or the like), industrial products (e.g., work wear coveralls, airline pillows, automobile trunk liners, sound proofing articles and/or the like), and household products (e.g., furniture scratch pads, mattress coil covers and/or the like).

I. Definitions

For the purposes of the present application, the following terms shall have the following meanings:

The term "fiber" can refer to a fiber of finite length or a filament of infinite length.

As used herein, the term "monocomponent" refers to fibers formed from one polymer or formed from a single blend of polymers. Of course, this does not exclude fibers to which additives have been added for color, anti-static properties, lubrication, hydrophilicity, liquid repellency, etc.

As used herein, the term "multicomponent" refers to fibers formed from at least two polymers (e.g., bicomponent fibers) that are extruded from separate extruders. The at least two polymers can each independently be the same or different from each other, or be a blend of polymers. The polymers are arranged in substantially constantly positioned distinct zones across the cross-section of the fibers. The components may be arranged in any desired configuration, such as sheath-core, side-by-side, pie, island-in-the-sea, and so forth. Various methods for forming multicomponent fibers are described in U.S. Pat. No. 4,789,592 to Taniguchi et al. and U.S. Pat. No. 5,336,552 to Strack et al., U.S. Pat. No. 5,108,820 to Kaneko, et al., U.S. Pat. No. 4,795,668 to Kruege, et al., U.S. Pat. No. 5,382,400 to Pike, et al., U.S. Pat. No. 5,336,552 to Strack, et al., and U.S. Pat. No. 6,200,669 to Marmon, et al., which are incorporated herein in their entirety by reference. Multicomponent fibers having various irregular shapes may also be formed, such as described in U.S. Pat. No. 5,277,976 to Hogle, et al., U.S.

Pat. No. 5,162,074 to Hills, U.S. Pat. No. 5,466,410 to Hills, U.S. Pat. No. 5,069,970 to Largman, et al., and U.S. Pat. No. 5,057,368 to Largman, et al., which are incorporated herein in their entirety by reference.

As used herein, the terms "nonwoven," "nonwoven web" and "nonwoven fabric" refer to a structure or a web of material which has been formed without use of weaving or knitting processes to produce a structure of individual fibers or threads which are intermeshed, but not in an identifiable, repeating manner. Nonwoven webs have been, in the past, formed by a variety of conventional processes such as, for example, meltblown processes, spunbond processes, and staple fiber carding processes.

As used herein, the term "meltblown" refers to a process in which fibers are formed by extruding a molten thermoplastic material through a plurality of fine, usually circular, die capillaries into a high velocity gas (e.g. air) stream which attenuates the molten thermoplastic material and forms fibers, which can be to microfiber diameter. Thereafter, the meltblown fibers are carried by the gas stream and are deposited on a collecting surface to form a web of random meltblown fibers. Such a process is disclosed, for example, in U.S. Pat. No. 3,849,241 to Buntin et al.

As used herein, the term "machine direction" or "MD" refers to the direction of travel of the nonwoven web during manufacturing.

As used herein, the term "cross direction" or "CD" refers to a direction that is perpendicular to the machine direction and extends laterally across the width of the nonwoven web.

As used herein, the term "spunbond" refers to a process involving extruding a molten thermoplastic material as filaments from a plurality of fine, usually circular, capillaries of a spinneret, with the filaments then being attenuated and drawn mechanically or pneumatically. The filaments are deposited on a collecting surface to form a web of randomly arranged substantially continuous filaments which can thereafter be bonded together to form a coherent nonwoven fabric. The production of spunbond non-woven webs is illustrated in patents such as, for example, U.S. Pat. Nos. 3,338,992; 3,692,613; 3,802,817; 4,405,297 and 5,665,300. In general, these spunbond processes include extruding the filaments from a spinneret, quenching the filaments with a flow of air to hasten the solidification of the molten filaments, attenuating the filaments by applying a draw tension, either by pneumatically entraining the filaments in an air stream or mechanically by wrapping them around mechanical draw rolls, depositing the drawn filaments onto a foraminous collection surface to form a web, and bonding the web of loose filaments into a nonwoven fabric. The bonding can be any thermal or chemical bonding treatment, with thermal point bonding being typical.

As used herein, the term "thermal point bonding" involves passing a material such as one or more webs of fibers to be bonded between a heated calender roll and an anvil roll. The calender roll is typically patterned so that the fabric is bonded in discrete point bond sites rather than being bonded across its entire surface.

As used herein, the term "polymer" generally includes, but is not limited to, homopolymers, copolymers, such as, for example, block, graft, random and alternating copolymers, terpolymers, etc. and blends and modifications thereof. Furthermore, unless otherwise specifically limited, the term "polymer" shall include all possible geometrical configurations of the material, including isotactic, syndiotactic and random symmetries.

The term "composite", as used herein, may be a structure comprising two or more layers, such as a film layer and a fiber layer or a plurality of fiber layers molded together. The two layers of a composite structure may be joined together such that a substantial portion of their common X-Y plane interface, according to certain embodiments of the invention.

Embodiments of the invention are directed to nonwoven fabrics comprising polylactic acid that exhibit improvements in strengths and toughness. In one embodiment, the present invention provides a spunbond nonwoven fabric comprising a plurality of fibers that are bonded to each other to form a coherent web, and wherein the plurality fibers comprise a blend of a PLA resin and at least one secondary alkane sulfonate. As explained in greater detail below, the inclusion of a secondary alkane sulfonate in the PLA resin improves the strength and toughness of the fabric in comparison to an identical fabric that does not include the secondary alkane sulfonate.

The at least one secondary alkane sulfonate typically comprises an alkane chain having from $C_{10}$-$C_{18}$, and wherein at least one of the secondary carbons of the alkane chain includes a sulfonate moiety. In particular, the at least one secondary alkane sulfonate may comprise a sulfonic acid, C13-C17-secondary alkane, sodium salt.

The alkane chain is generally linear although some chains may include some minor branching (e.g., $C_1$-$C_4$ side chain branching). Typically, the alkane chain will have from 10 to 18 carbon atoms, with an alkane chain length of 14 to 17 carbon atoms being somewhat more preferred. The secondary alkane sulfonate may include both mono- and disulfonic acids. However, the amount of monosulfonic acids in the secondary alkane sulfonate may generally be greater than 90%.

In one embodiment, the at least one secondary alkane sulfonate has one of the following structures:

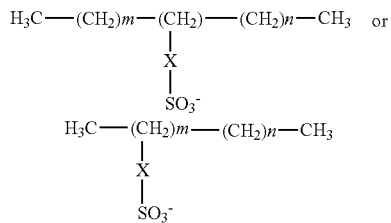

wherein m+n is a number between 7 and 16, and X is independently a $C_1$-$C_4$ alkyl or absent. In a preferred embodiment, the secondary alkane sulfonate has the following structure:

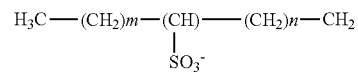

wherein m+n is a number between 8 and 15, and more preferably m+n is a number between 11 and 14. The secondary alkane sulfonate typically comprises a salt of sodium or potassium, but other cations could be used, such as a salt of calcium or magnesium. Alternatively, a quaternary ammonium comprised of modified fatty alkyl substrates such as those based on coco or stearyl substrates could be used. Such quaternary amines are available from Air Products and Chemicals, Inc. of Allentown, Pa. 18195-1501, USA.

In one embodiment, the secondary alkane sulfonate may be provided in a masterbatch carrier resin. For example, in one embodiment, the secondary alkane sulfonate is provided in a PLA polymer carrier resin that is blended with the PLA prior to spinning of the fibers. Typically, the amount of secondary alkane sulfonate in the PLA masterbatch is from about 5 to 25 weight percent based on the total weight of the masterbatch, with an amount from 10 to 20 weight percent being somewhat more typical. The masterbatch may also include additional additives, such as one or more compatibilizers. A commercial example of a secondary alkane sulfonate that may be used in embodiments of the claimed invention includes SUKANO® under the product name S546-Q1, which is a C14-C17 secondary alkane sulfonate sodium salt in a PLA masterbatch. One skilled in the art would recognize that design of a masterbatch for a secondary alkane sulfonate is a compromise between maximizing the use of PLA resins with very similar melt flow as observed for the base resin of the fiber, such as, for example, NatureWorks 6202D or 6252 D (Melt Index g/10 minutes (210° C.) 15-30 or 15, respectively, and the ease of suspending the secondary alkane sulfonate in a PLA polymer. Thus, a suitable masterbatch may be comprised of a PLA grade such as Nature Works 6362D with a higher melt Index (Melt Index g/10 minutes (210° C.) of 70-85.

A wide variety of different PLA resins may be used to prepare nonwoven fabrics in accordance with embodiments of the invention. Generally, polylactic acid based polymers are prepared from dextrose, a source of sugar, derived from field corn. In North America corn is used since it is the most economical source of plant starch for ultimate conversion to sugar. However, it should be recognized that dextrose can be derived from sources other than corn. Sugar is converted to lactic acid or a lactic acid derivative via fermentation through the use of microorganisms. Lactic acid may then be polymerized to form PLA. In addition to corn, other agricultural based sugar sources may be used including rice, sugar beets, sugar cane, wheat, cellulosic materials, such as xylose recovered from wood pulping, and the like.

The PLA resin should have proper molecular properties to be spun in spunbond processes. Examples of suitable include PLA resins are supplied from NatureWorks LLC, of Minnetonka, Minn. 55345 such as, grade 6752D, 6100D, and 6202D, which are believed to be produced as generally following the teaching of U.S. Pat. Nos. 5,525,706 and 6,807,973 both to Gruber et al. Other examples of suitable PLA resins may include L130, L175, and LX175, all from Corbion of Arkelsedijk 46, 4206 A C Gorinchem, the Netherlands.

In some embodiments, the nonwoven fabrics may be biodegradable. "Biodegradable" refers to a material or product which degrades or decomposes under environmental conditions that include the action of microorganisms. Thus, a material is considered as biodegradable if a specified reduction of tensile strength and/or of peak elongation of the material or other critical physical or mechanical property is observed after exposure to a defined biological environment for a defined time. Depending on the defined biological conditions, a fabric comprised of PLA might or might not be considered biodegradable.

A special class of biodegradable products made with a bio-based material might be considered as compostable if it can be degraded in a composing environment. The European standard EN 13432, "Proof of Compostability of Plastic Products" may be used to determine if a fabric or film comprised of sustainable content could be classified as compostable.

In some embodiments, the PLA nonwoven fabrics may comprise sustainable polymer components of biodegradable products that are derived from an aliphatic component possessing one carboxylic acid group (or a polyester forming derivative thereof, such as an ester group) and one hydroxyl group (or a polyester forming derivative thereof, such as an ether group) or may be derived from a combination of an aliphatic component possessing two carboxylic acid groups (or a polyester forming derivative thereof, such as an ester group) with an aliphatic component possessing two hydroxyl groups (or a polyester forming derivative thereof, such as an ether group).

The term "aliphatic polyester" covers—besides polyesters which are made from aliphatic and/or cycloaliphatic components exclusively also polyesters which contain besides aliphatic and/or cycloaliphatic units aromatic units, as long as the polyester has substantial sustainable content.

In addition to PLA based resins, nonwoven fabrics in accordance with embodiments of the invention may include other polymers derived from an aliphatic component possessing one carboxylic acid group and one hydroxyl group, which are alternatively called polyhydroxyalkanoates (PHA). Examples thereof are polyhydroxybutyrate (PHB), poly-(hydroxybutyrate-co-hydroxyvaleterate) (PHBV), poly-(hydroxybutyrate-co-polyhydroxyhexanoate) (PHBH), polyglycolic acid (PGA), poly-(epsilon-caprolactione) (PCL) and preferably polylactic acid (PLA).

Examples of additional polymers that may be used in embodiments of the invention include polymers derived from a combination of an aliphatic component possessing two carboxylic acid groups with an aliphatic component possessing two hydroxyl groups, and are polyesters derived from aliphatic diols and from aliphatic dicarboxylic acids, such as polybutylene succinate (PBSU), polyethylene succinate (PESU), polybutylene adipate (PBA), polyethylene adipate (PEA), polytetramethy-lene adipate/terephthalate (PTMAT).

Nonwoven fabrics in accordance with the invention may comprise monocomponent, bicomponent, or multicomponent fibers. Examples of bicomponent fibers include side-by-side, islands in the sea, and sheath/core arrangements. Preferably, the fibers have a sheath/core structure in which the sheath comprises a first polymer component, and the core comprises a second polymer component. In this arrangement, the polymers of the first and second polymer components may be the same or different from each other.

In a preferred embodiment, the fibers of the nonwoven fabric have a bicomponent arrangement in which the PLA blend comprising the secondary alkane sulfonate comprises a first polymer component defining a sheath, and a second polymer component comprises the core. Advantageously, the inventors have discovered that by blending the secondary alkane sulfonate into the polymer component defining the sheath, nonwoven fabrics having improved strength and toughness are provided. In addition, such improvements in physical properties may be obtainable in the absence of blending the secondary alkane sulfonate into the polymer component defining the core, which may help reduce the overall costs of preparing the nonwoven fabric.

In preferred embodiments, the sheath and the core both comprise a PLA resin. In these embodiments, a PLA spunbond nonwoven fabric may be provided that is substantially free of synthetic polymer components, such as petroleum-based materials and polymers. For example, the fibers of the PLA spunbond nonwoven fabric may have a bicomponent arrangement in which the both components are PLA based to thus produce a fiber that is 100% PLA.

As used herein, "100% PLA" may also include up to 5% additives including additives and/or masterbatches of additives to provide, by way of example only, color, softness, slip, antistatic protection, lubricity, hydrophilicity, liquid repellency, antioxidant protection and the like. In this regard, the nonwoven fabric may comprise 95-100% PLA, such as from 96-100% PLA, 97-100% PLA, 98-100% PLA, 99-100% PLA, etc. When such additives are added as a masterbatch, for instance, the masterbatch carrier may primarily comprise PLA in order to facilitate processing and to maximize sustainable content within the fibers.

For example, the PLA spunbond nonwoven fabric layer may comprise one or more additional additives. In such embodiments, for instance, the additive may comprise at least one of a colorant, a softening agent, a slip agent, an antistatic agent, a lubricant, a hydrophilic agent, a liquid repellent, an antioxidant, and the like, or any combination thereof.

In one embodiment, the PLA polymer of the sheath may be the same PLA polymer as that of the core. In other embodiments, the PLA polymer of the sheath may be a different PLA polymer than that of the core. For example, the bicomponent fibers may comprise PLA/PLA reverse bicomponent fibers such that the sheath comprises a first PLA grade, the core comprises a second PLA grade, and the first PLA grade and the second PLA grade are different (e.g., the first PLA grade has a higher melting point than the second PLA grade). By way of example only, the first PLA grade may comprise up to about 5% crystallinity, and the second PLA grade may comprise from about 40% to about 50% crystallinity.

In other embodiments, for instance, the first PLA grade may comprise a melting point from about 125° C. to about 135° C., and the second PLA grade may comprise a melting point from about 155° C. to about 170° C. In further embodiments, for example, the first PLA grade may comprise a weight percent of D isomer from about 4 wt. % to about 10 wt. %, and the second PLA grade may comprise a weight percent of D isomer of about 2 wt. %.

For example, in one embodiment, the core may comprise a PLA having a lower % D isomer of polylactic acid than that of the % D isomer PLA polymer used in the sheath. The PLA polymer with lower % D isomer will show higher degree of stress induced crystallization during spinning while the PLA polymer with higher D % isomer will retain a more amorphous state during spinning. The more amorphous sheath will promote bonding while the core showing a higher degree of crystallization will provide strength to the fiber and thus to the final bonded web. In one particular embodiment, the Nature Works PLA Grade PLA 6752 with 4% D Isomer can be used as the sheath while NatureWorks Grade 6202 with 2% D Isomer can be used as the core.

Generally, the weight percentage of the sheath to that of the core in the fibers may vary widely depending upon the desired properties of the nonwoven fabric. For example the weight ratio of the sheath to the core may vary between about 10:90 to 90:10, and in particular from about 20:80 to 80:20. In a preferred embodiment, the weight ratio of the sheath to the core is about 25:75 to 35:65, with a weight ratio of about 30:70 being preferred.

In other embodiments, a nonwoven fabric comprising bicomponent fibers is provided in which one of the polymer components comprises a blend of a PLA polymer and the secondary alkane sulfonate, and the other polymer component comprises a synthetic polymer, such as a petroleum derived polymer. Examples of synthetic polymers that may be used in embodiments of the invention may include polyolefins, such as polypropylene and polyethylene, polyesters, such as polyethylene terephthalate (PET), polytrimethylene terephthalate (PTT), and polybutylene terephthalate (PBT), nylons, polystyrenes, copolymers, and blends thereof, and other synthetic polymers that may be used in the preparation of fibers.

The amount of the secondary alkane sulfonate in the fibers will generally depend on where the secondary alkane sulfonate is present in the structure of the fibers, and the final desired properties of the nonwoven fabric. In general, the amount of the secondary alkane sulfonate may range from about 0.0125 weight percent to about 2.5 weight percent, based on the total weight of the polymeric component of the fiber in which the secondary alkane sulfonate is present. For example, in monocomponent fibers the weight percent of the secondary alkane sulfonate in the fibers will be based on the total weight of the fiber. In such a case, the amount secondary alkane sulfonate may range from about 0.0125 weight percent to about 2.5 weight percent, based on the total weight of the fiber. However, in the case of a bicomponent fiber, the weight percent of the secondary alkane sulfonate will be based on the total weight of the component in which the secondary alkane sulfonate is present. For example, in the case of a bicomponent fiber having a sheath to core weight ratio of 30:70, and in which the secondary alkane sulfonate is only present in the sheath, the weight percent of the secondary alkane sulfonate in the fiber may range from about 0.0125 weight percent to about 2.5 weight percent, based on the total weight of the sheath, which results in a weight percent of the secondary alkane sulfonate that is from 0.00375 to 0.750, based on the total weight of the fiber.

In one embodiment, the amount of the secondary alkane sulfonate may be at least about any one of the following: at least 0.0125, at least 0.0250, at least 0.0375, at least 0.050, at least 0.0625, at least 0.075, at least 0.100, at least 0.125, at least 0.150, at least 0.1875, at least 0.2, at least 0.2475, at least 0.25, at least 0.3 at least 0.375, at least 0.40, at least 0.495, at least 0.50, at least 0.60, at least 0.80, at least 0.9904, at least 1.0, at least 1.25, at least 1.2375, at least 1.5, at least 1.875, at least 2.0, and at least 2.50, based on the total weight of the polymeric component of the fiber in which the secondary alkane sulfonate is present. In other embodiments, the amount of the secondary alkane sulfonate may be less than about any one of the following: 0.0250, 0.0375, 0.050, 0.0625, 0.075, 0.100, 0.125, 0.150, 0.1875, 0.2, 0.2475, 0.25, 0.3, 0.375, 0.40, 0.495, 0.50, 0.60, 0.80, 0.9904, 1.0, 1.25, 1.2375, 1.5, 1.875, 2.0, and 2.50 weight percent. It should also be recognized that the amount of the secondary alkane sulfonate present in a polymer component of the fiber also encompasses ranges between the aforementioned amounts.

In a preferred embodiment, the fibers have a bicomponent structure in which the core and sheath both comprise a PLA polymer, and the sheath includes the secondary alkane sulfonate that is present in an amount that is from about 0.1 to 1 weight percent, based on the total weight of the sheath component, and in particular, from about 0.1 to 0.75, and more particularly from about 0.2 to 0.6 weight percent, and even more particularly, from about 0.3 to 0.4 weight percent, based on the total weight of the sheath component. Although, the secondary alkane sulfonate has generally discussed as being present in a monocomponent fiber or the sheath of a bicomponent fiber, it should be recognized that other arrangements are within the embodiments of the present invention. For example, the secondary alkane sulfonate may be present in only the core and not the sheath of a bicomponent fiber, or the secondary alkane sulfonate may be present in both the sheath and the core.

As the amount of the secondary alkane sulfonate in the fibers may vary depending on the amount of the secondary alkane sulfonate in the masterbatch polymer, the structure of the fiber (e.g., monocomponent or bicomponent), and in the case of the bicomponent, the ratio of a first polymer component to a second component in the fiber, the following tables provide exemplary ranges of the secondary alkane sulfonate in various fiber structures and at various loadings of the secondary alkane sulfonate in the masterbatch polymer, and at various loadings of the masterbatch in the PLA polymer.

TABLE 1A

Amounts of the Secondary Alkane Sulfonate (SAS) in the Sheath of a bicomponent fiber having a sheath to core weight ratio of 50:50 at various SAS and Master Batch (MB) loadings

| Amount of SAS in MB (%) | Amount of SAS in Sheath at an addition of 5% MB to Sheath polymer (%) | Amount of SAS in Sheath at an addition of 10% MB to Sheath polymer (%) | Amount of SAS in Sheath at an addition of 20% MB to Sheath polymer (%) | Amount of SAS in Sheath at an addition of 25% MB to Sheath polymer (%) |
|---|---|---|---|---|
| 0.25% | 0.0125 | 0.025 | 0.050 | 0.0625 |
| 0.50% | 0.025 | 0.050 | 0.100 | 0.125 |
| 0.75% | 0.0375 | 0.075 | 0.150 | 0.1875 |
| 1.0% | 0.050 | 0.100 | 0.200 | 0.250 |
| 2.0% | 0.100 | 0.200 | 0.400 | 0.500 |
| 3.0% | 0.150 | 0.300 | 0.600 | 0.750 |
| 4.0% | 0.200 | 0.400 | 0.800 | 1.000 |
| 4.95% | 0.2475 | 0.495 | 0.9904 | 1.2375 |
| 5.0% | 0.250 | 0.500 | 1.00 | 1.2500 |
| 7.5% | 0.375 | 0.750 | 1.500 | 1.8750 |
| 10.0% | 0.500 | 1.000 | 2.000 | 2.5000 |

TABLE 1B

Amounts of the Secondary Alkane Sulfonate (SAS) in the Fabric comprised of bicomponent fibers having a sheath to core weight ratio of 50:50 at various SAS and Master Batch (MB) loadings

| Amount of SAS in MB (%) | Amount of SAS in Fabric at an addition of 5% MB to Sheath polymer (%) | Amount of SAS in Fabric at an addition of 10% MB to Sheath polymer (%) | Amount of SAS in Fabric at an addition of 20% MB to Sheath polymer (%) | Amount of SAS in Fabric at an addition of 25% MB to Sheath polymer (%) |
|---|---|---|---|---|
| 0.25% | 0.00625 | 0.0125 | 0.025 | 0.03125 |
| 0.50% | 0.01250 | 0.025 | 0.050 | 0.06250 |
| 0.75% | 0.01875 | 0.0375 | 0.075 | 0.09375 |
| 1.0% | 0.02500 | 0.050 | 0.100 | 0.12500 |
| 2.0% | 0.05000 | 0.100 | 0.200 | 0.25000 |
| 3.0% | 0.07500 | 0.150 | 0.300 | 0.37600 |
| 4.0% | 0.10000 | 0.200 | 0.400 | 0.50000 |
| 4.95% | 0.12375 | 0.2475 | 0.495 | 0.61875 |
| 5.0% | 0.12500 | 0.250 | 0.500 | 0.62500 |
| 7.5% | 0.18750 | 0.375 | 0.750 | 0.93750 |
| 10.0% | 0.25000 | 0.500 | 1.000 | 1.25000 |

TABLE 2A

Amounts of the Secondary Alkane Sulfonate (SAS) in Sheath of a bicomponent fiber having a sheath to core weight ratio of 30:70 at various SAS and Master Batch (MB) loadings

| Amount of SAS in MB (%) | Amount of SAS in Sheath at an addition of 5% MB to Sheath polymer (%) | Amount of SAS in Sheath at an addition of 10% MB to Sheath polymer (%) | Amount of SAS in Sheath at an addition of 20% MB to Sheath polymer (%) | Amount of SAS in Sheath at an addition of 25% MB to Sheath polymer (%) |
|---|---|---|---|---|
| 0.25% | 0.0125 | 0.025 | 0.050 | 0.0625 |
| 0.50% | 0.025 | 0.050 | 0.100 | 0.125 |
| 0.75% | 0.0375 | 0.075 | 0.150 | 0.1875 |
| 1.0% | 0.050 | 0.100 | 0.200 | 0.250 |
| 2.0% | 0.100 | 0.200 | 0.400 | 0.500 |
| 3.0% | 0.150 | 0.300 | 0.600 | 0.750 |
| 4.0% | 0.200 | 0.400 | 0.800 | 1.000 |
| 4.95% | 0.2475 | 0.495 | 0.9904 | 1.2375 |
| 5.0% | 0.250 | 0.500 | 1.00 | 1.2500 |
| 7.5% | 0.375 | 0.750 | 1.500 | 1.8750 |
| 10.0% | 0.500 | 1.000 | 2.000 | 2.5000 |

TABLE 2B

Amounts of the Secondary Alkane Sulfonate (SAS) in a Fabric comprising bicomponent fibers having a sheath to core weight ratio of 30:70 at various SAS and Master Batch (MB) loadings

| Amount of SAS in MB (%) | Amount of SAS in Fabric at an addition of 5% MB to Sheath polymer (%) | Amount of SAS in Fabric at an addition of 10% MB to Sheath polymer (%) | Amount of SAS in Fabric at an addition of 20% MB to Sheath polymer (%) | Amount of SAS in Fabric at an addition of 25% MB to Sheath polymer (%) |
|---|---|---|---|---|
| 0.25% | 0.00375 | 0.0075 | 0.015 | 0.01875 |
| 0.50% | 0.00750 | 0.0150 | 0.0300 | 0.0375 |
| 0.75% | 0.01125 | 0.0225 | 0.04500 | 0.05625 |
| 1.0% | 0.0150 | 0.0300 | 0.0600 | 0.0750 |
| 2.0% | 0.030 | 0.060 | 0.1200 | 0.1500 |
| 3.0% | 0.0450 | 0.0900 | 0.1800 | 0.2250 |
| 4.0% | 0.0600 | 0.1200 | 0.2400 | 0.3000 |
| 4.95% | 0.07425 | 0.1485 | 0.2970 | 0.37125 |
| 5.0% | 0.0750 | 0.1500 | 0.3000 | 0.375 |
| 7.5% | 0.1125 | 0.2250 | 0.4500 | 0.5625 |
| 10.0% | 0.1500 | 0.3000 | 0.6000 | 0.7500 |

TABLE 3

Amounts of the Secondary Alkane Sulfonate (SAS) in a Fabric comprising PLA monocomponent fibers at various SAS and Master Batch (MB) loadings

| Amount of SAS in MB (%) | Amount of SAS in Fabric at an addition of 5% MB (%) | Amount of SAS in Fabric at an addition of 10% MB (%) | Amount of SAS in Fabric at an addition of 20% MB (%) | Amount of SAS in Fabric at an addition of 25% (%) |
|---|---|---|---|---|
| 0.25% | 0.0125 | 0.025 | 0.050 | 0.0625 |
| 0.50% | 0.025 | 0.050 | 0.100 | 0.125 |
| 0.75% | 0.0375 | 0.075 | 0.150 | 0.1875 |
| 1.0% | 0.050 | 0.100 | 0.200 | 0.250 |
| 2.0% | 0.100 | 0.200 | 0.400 | 0.500 |
| 3.0% | 0.150 | 0.300 | 0.600 | 0.750 |
| 4.0% | 0.200 | 0.400 | 0.800 | 1.000 |
| 4.95% | 0.2475 | 0.495 | 0.9904 | 1.2375 |
| 5.0% | 0.250 | 0.500 | 1.600 | 1.25 |

TABLE 3-continued

Amounts of the Secondary Alkane Sulfonate (SAS)
in a Fabric comprising PLA monocomponent fibers
at various SAS and Master Batch (MB) loadings

| Amount of SAS in MB (%) | Amount of SAS in Fabric at an addition of 5% MB (%) | Amount of SAS in Fabric at an addition of 10% MB (%) | Amount of SAS in Fabric at an addition of 20% MB (%) | Amount of SAS in Fabric at an addition of 25% MB (%) |
|---|---|---|---|---|
| 7.5% | 0.375 | 0.750 | 1.500 | 1.875 |
| 10.0% | 0.500 | 1.000 | 2.000 | 2.500 |

In accordance with certain embodiments, for example, the nonwoven fabric may have a basis weight from about 7 grams per square meter (gsm) to about 150 gsm. In other embodiments, for instance, the fabric may have a basis weight from about 8 gsm to about 70 gsm. In certain embodiments, for example, the fabric may comprise a basis weight from about 10 gsm to about 50 gsm. In further embodiments, for instance, the fabric may have a basis weight from about 11 gsm to about 30 gsm. As such, in certain embodiments, the fabric may have a basis weight from at least about any of the following: 7, 8, 9, 10, and 11 gsm and/or at most about 150, 100, 70, 60, 50, 40, and 30 gsm (e.g., about 9-60 gsm, about 11-40 gsm, etc.).

Moreover, fabrics prepared in accordance with embodiments of the invention may be characterized by an area shrinkage of less than 5%. In further embodiments, for example, the fabrics may be characterized by an area shrinkage of less than 2%.

According to certain embodiments, for example, the fibers may have a linear mass density from about 1 dtex to about 5 dtex. In other embodiments, for instance, the fibers may have a dtex from about 1.5 dtex to about 3 dtex. In further embodiments, for example, the fibers may have a linear mass density from about 1.6 dtex to about 2.5 dtex. As such, in certain embodiments, the fibers have a linear mass density from at least about any of the following: 1, 1.1, 1.2, 1.3, 1.4, 1.5, and 1.6 dtex and/or at most about 5, 4.5, 4, 3.5, 3, and 2.5 dtex (e.g., about 1.4-4.5 dtex, about 1.6-3 dtex, etc.).

Advantageously, the inventors of the present invention have discovered that the addition of the secondary alkane sulfonate in the PLA resin provides significant increases in mechanical properties in comparison to an identical or similarly prepared nonwoven fabric that does not include the secondary alkane sulfonate. In this regard, nonwoven fabrics in accordance with embodiments of the present invention may exhibit tensile strengths that are 50% greater in comparison to a similarly prepared nonwoven fabric that does not include the secondary alkane sulfonate. In some embodiments, the nonwoven fabric may exhibit a tensile strength that is from 50% to 200% greater than the tensile strength of a similarly prepared nonwoven fabric that does not include the secondary alkane sulfonate.

In particular, nonwoven fabrics in accordance with the present invention may exhibit increases in machine direction (MD) tensile strengths that are from about 55 to 125% in comparison to a similarly prepared nonwoven fabric that does not include the secondary alkane sulfonate. In some embodiments, the inventive nonwoven fabrics may exhibit an increase in MD tensile strength ranging from about 50 to 150%, such as from about 55 to 125%, from about 65 to 110%, from about 85 to 110%, or from about 90 to 110%, in comparison to a similarly prepared nonwoven fabric that does not include the secondary alkane sulfonate.

In some embodiments, nonwoven fabrics in accordance with the present invention may exhibit increases in cross direction (CD) tensile strengths that are from about 50 to 200% in comparison to a similarly prepared nonwoven fabric that does not include the secondary alkane sulfonate. In some embodiments, the inventive nonwoven fabrics may exhibit an increase in CD tensile strength ranging from about 50 to 170%, such as from about 55 to 165%, from about 65 to 160%, from about 85 to 150%, or from about 90 to 125%, in comparison to a similarly prepared nonwoven fabric that does not include the secondary alkane sulfonate.

Nonwoven fabrics in accordance with embodiments of the present invention also exhibit increased toughness in comparison to a similarly prepared nonwoven fabric that does not include the secondary alkane sulfonate. The toughness of nonwoven fabrics may be compared by examining the product resulting from the multiplication of the observed percent elongation and the observed tensile strength of the fabric. The product of this multiplication is referred to as the Index of Toughness, which is approximately proportional to the area under the stress strain curve. As discussed below in the Test Methods section, all tensile and elongation values are obtained according to German Method 10 DIN 53857 in which a sample having a width of 5 cm and a 100 mm gauge length at a cross-head speed of 200 mm/min were recorded at peak. Since Index of Toughness results from the product of multiplying Tensile X % Elongation, the Index of Toughness has units of (N/5 cm)-%. Since all mechanical properties result from testing a 5 cm wide sample, the units for Index of Toughness in this document will be simplified to N-%.

Nonwoven fabrics in accordance with the present invention may exhibit an MD Index of Toughness that is from about 2,000 to 7,500 N-%, and in particular, from about 2,300 to 6,500, and more particularly, from about 2,300 to 6,000 N-%, and a CD Index of Toughness that is from about 1,000 to 5,000 N-%, and in particular, from about 1,250 to 5,000, and more particularly, from about 1,250 to 3,500 N-%.

In one embodiment, the inventive nonwoven fabric may exhibit an increase in MD Index of Toughness that is from 20 to 1,250% in comparison to a similarly prepared nonwoven fabric that does not include the secondary alkane sulfonate. For example, the inventive nonwoven fabric may exhibit an increase in MD Index of Toughness of any one or more of at least 25%, at least 100%, at least 200%, at least 300%, at least 400%, at least 500%, at least 600%, at least 700%, at least 800%, at least 900%, at least 1,000%, at least 1,050%, at least 1,100%, at least 1,150%, at least 1,200%, at least 1,250%, at least 1,300%, or at least 1,500%, in comparison to a similarly prepared nonwoven fabric that does not include the secondary alkane sulfonate.

In some embodiments, the inventive nonwoven fabric may exhibit an increase in CD Index of Toughness that is from about 50 to 1,000% in comparison to a similarly prepared nonwoven fabric that does not include the secondary alkane sulfonate. For example, the inventive nonwoven fabric may exhibit an increase in CD Index of Toughness of any one or more of at least 60%, at least 75%, at least 80%, at least 85%, at least 90%, at least 100%, at least 150%, at least 200%, at least 250%, at least 300%, at least 350%, at least 400%, at least 500%, at least 550%, at least 600%, at least 700%, at least 800%, at least 900%, at least 1,000%, or at least 1,025%, in comparison to a similarly prepared nonwoven fabric that does not include the secondary alkane sulfonate.

To account for variations in basis weights, it may also be useful to consider Relative Index of Toughness for the inventive nonwoven fabrics in comparison to similarly prepared nonwoven fabrics that do not include the secondary alkane sulfonate. The inventive nonwoven fabrics also exhibited significant increases in toughness in comparison to the nonwoven fabrics of the comparative examples. The Relative Index of Toughness is calculated from the Index of Toughness, which is then normalized for basis weight. The Toughness Index can be divided by basis weight to provide a normalized Index of Toughness with units of $N\text{-}\%/g/m^2$.

Nonwoven fabrics in accordance with the present invention may exhibit an MD Relative Index of Toughness that is from about 50 to 150 $N\text{-}\%/g/m^2$, and in particular, from about 75 to 125, and more particularly, from about 85 to 115 $N\text{-}\%/g/m^2$, and a CD Relative Index of Toughness that is from about 40 to 100 $N\text{-}\%/g/m^2$, and in particular, from about 45 to 85, and more particularly, from about 45 to 75 $N\text{-}\%/g/m^2$.

In one embodiment, the inventive nonwoven fabric may exhibit an increase in MD Relative Index of Toughness that is from 100 to 1000% in comparison to a similarly prepared nonwoven fabric that does not include the secondary alkane sulfonate. In a preferred embodiment, the inventive nonwoven fabric may exhibit an increase in MD Relative Index of Toughness that is from about 80 to 500%, and more preferably, from about 140 to 480% in comparison to a similarly prepared nonwoven fabric that does not include the secondary alkane sulfonate. For example, the inventive nonwoven fabric may exhibit an increase in MD Relative Index of Toughness of any one or more of at least 100%, at least 125%, at least 150%, at least 175%, at least 200%, at least 225%, at least 250%, at least 275%, at least 300%, at least 325%, at least 350%, at least 375%, at least 400%, at least 425%, at least 450%, at least 475%, at least 500%, at least 525%, at least 550%, at least 575%, at least 600%, at least 625%, at least 650%, at 675%, at least 700%, at least 725%, at least 750%, at least 775%, at least 800%, at least 825%, at least 850%, at least 875%, at least 900%, at least 925%, at least 950, at least 975%, or at least 1,000%, in comparison to a similarly prepared nonwoven fabric that does not include the secondary alkane sulfonate.

In one embodiment, the inventive nonwoven fabric may exhibit an increase in CD Relative Index of Toughness that is from 100 to 1000% in comparison to a similarly prepared nonwoven fabric that does not include the secondary alkane sulfonate. In a preferred embodiment, the inventive nonwoven fabric may exhibit an increase in CD Relative Index of Toughness that is from about 140 to 500%, and more preferably, from about 140 to 410% in comparison to a similarly prepared nonwoven fabric that does not include the secondary alkane sulfonate. For example, the inventive nonwoven fabric may exhibit an increase in MD Relative Index of Toughness of any one or more of at least 100%, at least 125%, at least 150%, at least 175%, at least 200%, at least 225%, at least 250%, at least 275%, at least 300%, at least 325%, at least 350%, at least 375%, at least 400%, at least 425%, at least 450%, at least 475%, at least 500%, at least 525%, at least 550%, at least 575%, at least 600%, at least 625%, at least 650%, at 675%, at least 700%, at least 725%, at least 750%, at least 775%, at least 800%, at least 825%, at least 850%, at least 875%, at least 900%, at least 925%, at least 950, at least 975%, or at least 1,000%, in comparison to a similarly prepared nonwoven fabric that does not include the secondary alkane sulfonate.

When comparing properties of different nonwovens it is often useful to compare the root mean square of the combined values of the MD and CD property of interest. This method allows comparison of single values. The root mean square provides a single number that combines input from both the MD and the CD values by taking the square root of the sum of the square of the MD value plus the square of the CD value. Use of the root mean square method to combine the MD and the CD results is particularly useful if samples to be compared were made on different machines or under some different condition that might influence the MD/CD ratio. The root mean square of the Toughness Index per basis weight is calculated with the following formula:

$$\left( \sqrt{\frac{(MDTI)^2 + (CDTI)^2}{2}} \right) / \text{Basis weight}$$

Where MDTI is the machine direction Toughness Index and CDTI is the cross direction Toughness Index.

Nonwoven fabrics in accordance with the invention may have a root mean square of the Toughness Index per basis weight that is at least 55 $N\text{-}\%/g/m^2$, and more preferably, at least 65 $N\text{-}\%/g/m^2$, and even more preferably at least 70 $N\text{-}\%/g/m^2$. In one embodiment, the fabric has a root mean square of the Toughness Index per basis weight has a value from about 55 to 250 $N\text{-}\%/g/m^2$, and in particular, from about 65 to 150 $N\text{-}\%/g/m^2$, and more particularly, from about 65 to 100 $N\text{-}\%/g/m^2$. In one embodiment, the fabric has a root mean square of the Toughness Index per basis weight of at least 75, at least 80, at least 85, at least 90, at least 95, at least 100, at least 105, at least 110, at least 115, at least, 120, at least 125, at least, 130, at least 135, at least 140, at least 145, at least 150, at least 155, at least 160, at least 165, at least 170, at least 175, at least 180, at least 185, at least 190, at least 195, and at least 200 $N\text{-}\%/g/m^2$.

By "similarly prepared nonwoven fabric" it should be understood the comparison nonwoven fabric has the identical polymer composition with the exception of the secondary alkane sulfonate, and that slight variations in processing conditions, such as temperature (e.g., extruder, calendaring, and die temperatures), draw speeds, and pressures may exist.

Figure 1B:
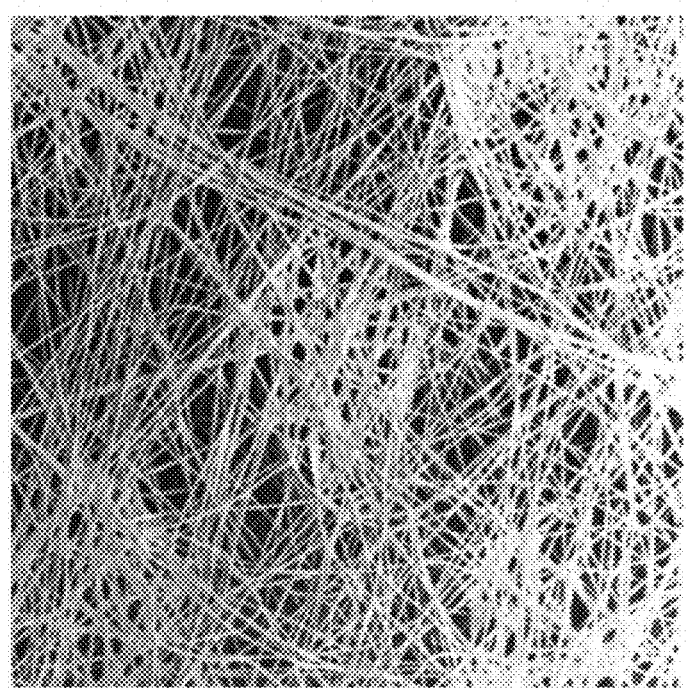
Figure 2A:
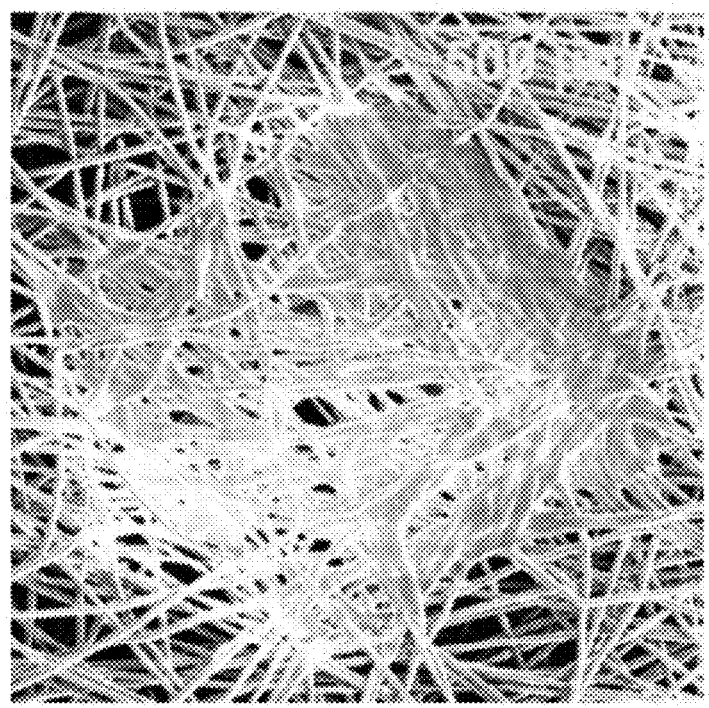
FIGS. 2A and 2B are SEM images of individual bond points on a surface of a nonwoven fabric that includes a secondary alkane sulfonate.
Figure 2B:
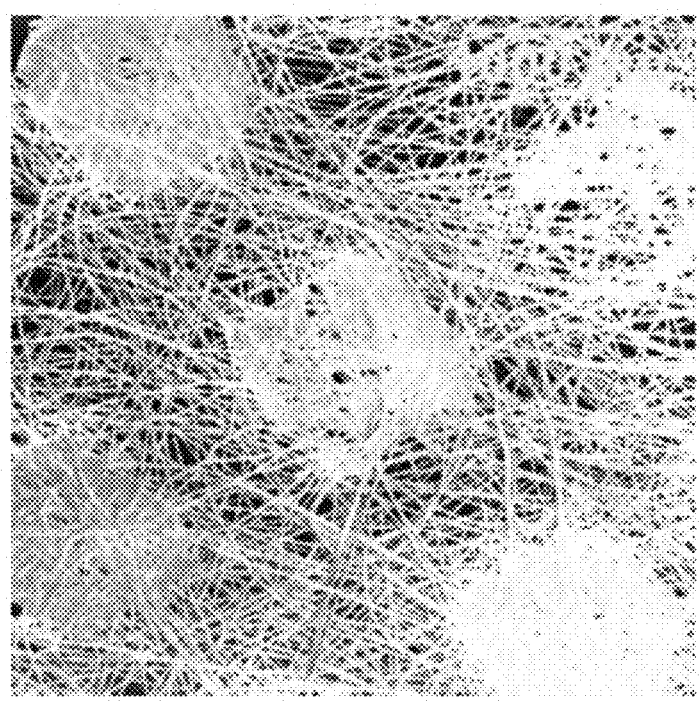

While not wishing to be bound by theory, it is believed that the presence of the secondary alkane sulfonate in the fibers may help improve bonding of fibers to each other, which results in improvements in the mechanical properties of the nonwoven fabric. In this regard, FIGS. 1A and 1B are SEM images of a nonwoven fabric taken at a magnification of 250× and 100×, respectively, and FIGS. 2A and 2B are SEM images of an nonwoven fabric in accordance with the present invention taken at a magnification of 250× and 100×, respectively. The fabric of FIGS. 1A and 1B are identical to the fabric of FIGS. 2A and 2B with the exception that the fabric of FIGS. 1A and 1B do not include a secondary alkane sulfonate. In both fabric, the fabric were point bonded with a calender roll.

The SEM images of the fabric of FIGS. 1A and 1B show that the individual fibers of the bond points were poorly bonded to each other. More specifically, it is observed that the fibers exhibited relatively poor melting and flowing of the polymer during bonding. In contrast, the SEM images of the fabric of FIGS. 2A and 2B exhibited good melting and flow of the polymer within each bond point. As can be seen in FIG. 2B, this resulted in each bond point exhibiting a film like appearance due to the melting and flowing of the polymer. The inventive fabric exhibited significant improvements in bonding in comparison to the fabric that did not include the secondary alkane sulfonate.

According to certain embodiments, for instance, the fabric may comprise a machine direction (MD) tensile strength at peak from about 25 N/5 cm to about 150 N/5 cm. In other embodiments, for example, the fabric may comprise a MD tensile strength at peak from about 50 N/5 cm to about 150 N/5 cm. In further embodiments, for instance, the fabric may comprise a MD tensile strength at peak from about 65 N/5 cm to about 90 N/5 cm. As such, in certain embodiments the fabric may comprise a MD tensile strength at peak from at least about any of the following: 25, 26, 27, 28, 29, 30, 50, 60, 70, 80, 100, 110, 120, 130 N/5 cm, and 140/5 cm, and/or at most about 175, 150, 145, 140, 130, 120 N/5 cm, and 110, 100, and 90 N/5 cm (e.g., about 25-175 N/5 cm, about 80-140 N/5 cm, etc.).

In certain embodiments, for example, the fabric may comprise a cross machine direction (CD) tensile strength at peak from about 20 N/5 cm to about 85 N/5 cm. In other embodiments, for instance, the fabric may comprise a CD tensile strength at peak from about 25 N/5 cm to about 75 N/5 cm. In some embodiments, for example, the fabric may comprise a CD tensile strength at peak from about 29 N/5 cm to about 74 N/5 cm. As such, in certain embodiments, the fabric may comprise a CD tensile strength at peak from at least about any of the following: 20, 21, 22, 23, 24, 25, 26, 27, 28, 29, and 30 N/5 cm and/or at most about 85, 80, 75, 70, 65, 60, and 50 N/5 cm (e.g., about 20-85 N/5 cm, about 25-75 N/5 cm, etc.).

According to certain embodiments, for instance, the fabric may comprise an MD elongation percentage at peak from about 20% to about 50%. In other embodiments, for example, the fabric may comprise an MD elongation percentage at peak from about 25% to about 45%. In further embodiments, for instance, the fabric may comprise an MD elongation percentage at peak from about 28% to about 41%. As such, in certain embodiments, the fabric may comprise an MD elongation percentage at peak from at least about any of the following: 20, 21, 22, 23, 24, 25, 26, 27, 28, 29, 30, 31, 32, 33, 34, 35, 36, 37, 38, 39, and 40% and/or at most about 50, 45, 44, 43, 42, 41, 40, 39, 38, 37, 36, 35, 34, 33, 32, 31, and 30% (e.g., about 20-50%, about 21-45%, etc.).

In certain embodiments, for example, the fabric may comprise a CD elongation percentage at peak from about 30% to about 75%. In other embodiments, for instance, the fabric may comprise a CD elongation percentage at peak from about 35% to about 60%. In some embodiments, for example, the fabric may comprise a CD elongation percentage at peak from about 40% to about 50%. As such, in certain embodiments, the fabric may comprise an CD elongation percentage at peak from at least about any of the following: 10, 15, 20, 25, 30, 35, 36, 37, 38, 39, 40, 41, 42, 43, 44, 45, 46, 47, 48, and 49% and/or at most about 55, 50, 49, 48, and 47% (e.g., about 10-55%, about 15-50%, etc.).

In accordance with certain embodiments, particular processes may be used to prepare the PLA spunbond nonwoven fabrics. In such embodiments, the process may include providing a stream of molten or semi-molten PLA resin that includes at least one secondary alkane sulfonate, forming a plurality of drawn PLA continuous filaments, depositing the plurality of PLA continuous filaments onto a collection surface, exposing the plurality of PLA continuous filaments to ions, and bonding the plurality of PLA continuous filaments to form the PLA spunbond nonwoven fabric. According to certain embodiments, for example, forming the plurality of PLA continuous filaments may comprise spinning the plurality of PLA continuous filaments, drawing the plurality of PLA continuous filaments, and randomizing the plurality of PLA continuous filaments.

In this regard, the spunbond nonwoven web may be produced, for example, by the conventional spunbond process wherein molten polymer is extruded into continuous filaments which are subsequently quenched, attenuated or drawn mechanically by draw rolls or pneumatically by a high velocity fluid, and collected in random arrangement on a collecting surface. After filament collection, any thermal, chemical or mechanical bonding treatment may be used to form a bonded web such that a coherent web structure results.

In accordance with certain embodiments, for instance, the process may occur at a fiber draw speed greater than about 2500 m/min. In other embodiments, for example, the process may occur at a fiber draw speed from about 3000 m/min to about 4000 m/min. In further embodiments, for instance, the process may occur at a fiber draw speed from about 3000 m/min to about 5500 m/min. As such, in certain embodiments, the process may occur at a fiber draw speed from at least about any of the following: 2501, 2550, 2600, 2650, 2700, 2750, 2800, 2850, 2900, 2950, and 3000 m/min and/or at most about 5500, 4000, 3950, 3900, 3850, 3800, 3750, 3700, 3650, 3600, 3550, and 3500 m/min (e.g., about 2700-3800 m/min, about 3000-3700 m/min, etc.).

In accordance with certain embodiments, for instance, bonding the web to form the PLA spunbond nonwoven fabric may comprise thermal point bonding the web with heat and pressure via a calender having a pair of cooperating rolls including a patterned roll. In such embodiments, for example, thermal point bonding the web may comprise imparting a three-dimensional geometric bonding pattern onto the PLA spunbond nonwoven fabric. The patterned roll may comprise a three-dimensional geometric bonding pattern. In some embodiments, for example, the bonding pattern at least one of a diamond pattern, a hexagonal dot pattern, an oval-elliptic pattern, a rod-shaped pattern, or any combination thereof. In some embodiments, the calender may include a release coating to minimize deposit of molten or semi molten polymer on the surface of one or more of the rolls. As an example, such release coating is described in European Patent Application No. 1,432,860, which is incorporated herein in its entirety by reference.

In accordance with certain embodiments, for instance, the process may further comprise dissipating static charge from the PLA spunbond nonwoven fabric proximate to the calender via the static control unit. In some embodiments, for example, the static control unit may comprise an ionization source. In further embodiments, for instance, the ionization source may comprise an ionization bar. However, in other embodiments, for example, dissipating static charge from the PLA spunbond nonwoven fabric may comprise contacting the PLA spunbond nonwoven fabric with a static bar.

In accordance with certain embodiments, for instance, the process may further comprise cutting the PLA spunbond nonwoven fabric to form cut PLA spunbond nonwoven fabric, exposing the cut PLA spunbond nonwoven fabric to ions via a third ionization source, and winding the cut PLA spunbond nonwoven fabric into rolls. In such embodiments, for example, the third ionization source may comprise an ionization bar.

In accordance with certain embodiments, for instance, the process may further comprise increasing humidity while forming the plurality of PLA continuous filaments. In such embodiments, for example, increasing humidity may comprise applying at least one of steam, fog, mist, or any combination thereof to the plurality of PLA continuous filaments.

Certain embodiments according to the invention provide systems for preparing a PLA spunbond nonwoven fabric. In accordance with certain embodiments, the system includes a first PLA source configured to provide a stream of molten or semi-molten PLA resin, a source of at least one secondary alkane sulfonate that is configured to introduce the at least one secondary alkane sulfonate into the PLA source, a spin beam in fluid communication with the first PLA source, a collection surface disposed below an outlet of the spin beam onto which the PLA continuous filaments are deposited to form the PLA spunbond nonwoven fabric, a first ionization source positioned and arranged to expose the PLA continuous filaments to ions, and a calender positioned downstream of the first ionization source. The spin beam, according to certain embodiments, is configured to extrude and draw a plurality of PLA continuous filaments.

In this regard, the spunbond nonwoven web may be produced, for example, by the conventional spunbond process on spunbond machinery such as, for example, the Reicofil-3 line or Reicofil-4 line from Reifenhauser, as described in U.S. Pat. No. 5,814,349 to Geus et al, the entire contents of which are incorporated herein by reference, wherein molten polymer is extruded into continuous filaments which are subsequently quenched, attenuated pneumatically by a high velocity fluid, and collected in random arrangement on a collecting surface. In some embodiments, the continuous filaments are collected with the aid of a vacuum source positioned below the collection surface. After filament collection, any thermal, chemical or mechanical bonding treatment may be used to form a bonded web such that a coherent web structure results. As one skilled in the art will understand, examples of thermal bonding may include thru-air bonding where hot air is forced through the web to soften the polymer on the outside of certain fibers in the web followed by at least limited compression of the web or calender bonding where the web is compressed between two rolls, at least one of which is heated, and typically one is an embossed roll.

In some embodiments, for instance, the collection surface may comprise conductive fibers. The conductive fibers may comprise monofilament wires made from polyethersulfone conditioned with polyamide (e.g., Huycon—LX 135). In the machine direction, the fibers comprise polyamide conditioned polyethersulfone. In the cross-machine direction, the fibers comprise polyamide conditioned polyethersulfone in combination with additional polyethersulfone.

Figure 3:
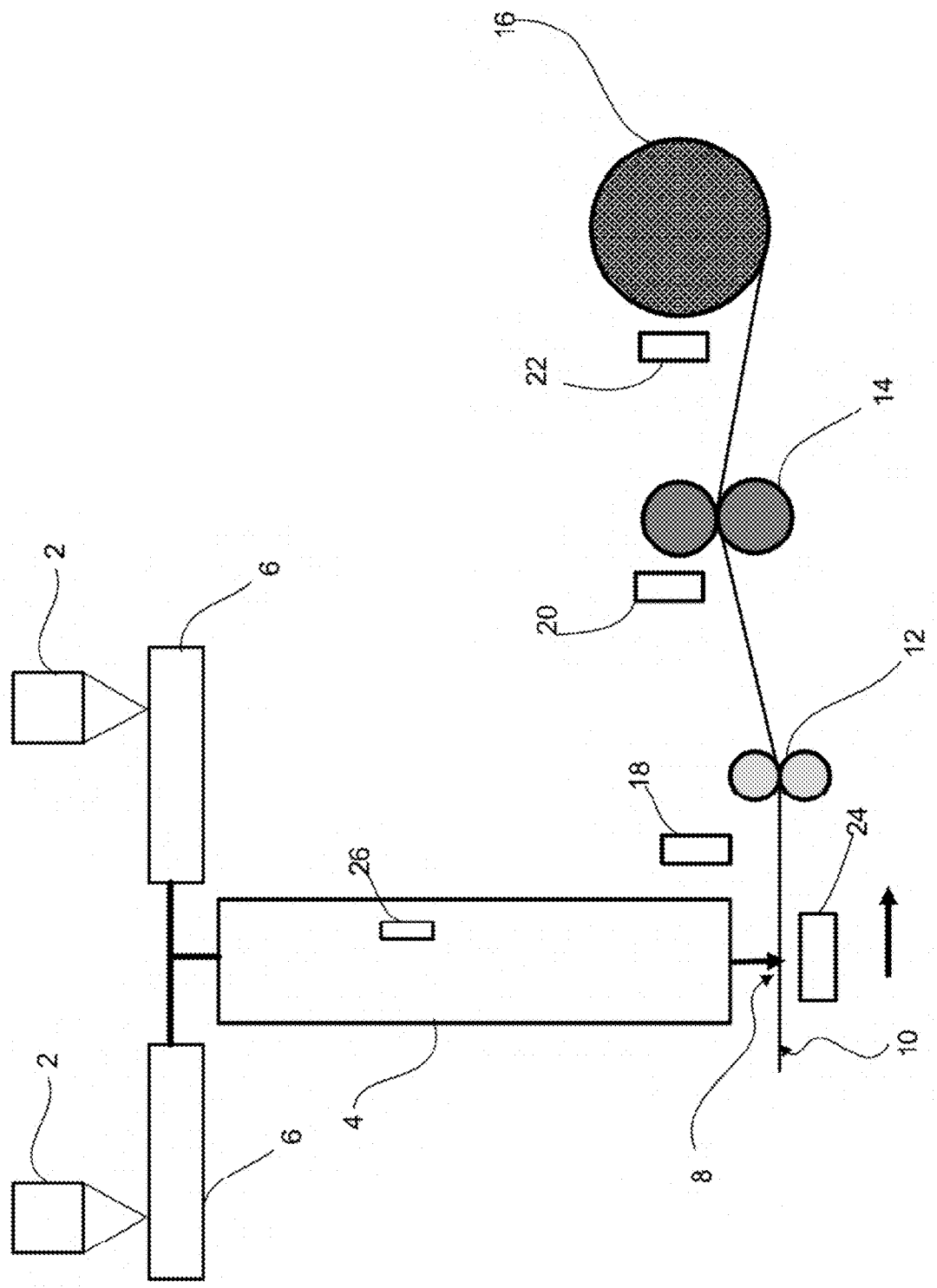
FIG. 3 is a schematic diagram of the PLA spunbond nonwoven fabric preparation system in accordance with certain embodiments of the invention.

With reference to FIG. 3, for example, a schematic diagram of the PLA spunbond nonwoven fabric preparation system in accordance with certain embodiments of the invention is illustrated.

As shown in FIG. 3, a PLA source (i.e. hopper) 2 is in fluid communication with the spin beam 4 via the extruder 6. At least one secondary alkane sulfonate is then blended with PLA resin in the extruder 6 to provide a molten or semi-molten PLA stream that is introduced into the spin beam 4. It should be noted that the secondary alkane sulfonate may be introduced directly into the extruder or may be introduced into the PLA source (e.g., the hopper) prior to the PLA resin being introduced into the extruder.

Although FIG. 3 illustrates an embodiment having two PLA sources 2 and two extruders 6, the system may include any number of polymer sources (e.g., PLA, synthetic polymer, such as polypropylene, polyethylene, etc.) and extruders as dictated by a particular application as understood by one of ordinary skill in the art. Following extrusion, the extruded polymer may then enter a plurality of spinnerets (not shown) for spinning into filaments. Following spinning, the spun filaments may then be drawn (i.e. attenuated) via a drawing unit (not shown) and randomized in a diffuser (28 in FIGS. 4A-4C). The spin beam 4 produces a curtain of filaments (30 in FIGS. 4A-4C) that is deposited on the collection surface 10 at point 8.

In one embodiment, the thus deposited filaments may then be bonded to form a coherent web. In some embodiments, a pair of cooperating rolls 12 (also referred to herein as a "press roll") stabilize the web of the PLA continuous filaments by compressing the web before delivery to the calender 14 for bonding. In some embodiments, for example, the press roll may include a ceramic coating deposited on a surface thereof. In certain embodiments, for instance, one roll of the pair of cooperating rolls 12 may be positioned above the collection surface 10, and a second roll of the pair of cooperating rolls 12 may be positioned below the collection surface 10. Finally, the bonded PLA spunbond nonwoven fabric moves to a winder 16, where the fabric is wound onto rolls.

During the course of their investigation, the inventors have discovered that static generation during fiber spinning and web processing when PLA is exposed on the fiber surface promotes web wraps at the press rolls and calender of the spunbond machine. This web wrap is undesirable and generally has prevented the high speed production of fabrics comprising 100% PLA, or fabrics in which PLA is exposed at the surface of the fibers. One method of addressing web wrap is by increasing the humidity of the spunbond process by, for example, injecting steam into the air stream used to quench the just-spun fibers or providing a fine mist or fog of moisture around the press rolls where the spun fibers are first formed into an unbonded web. Although the extra humidity provides some protection from web wraps, the addition of high moisture over a period of time may promote corrosion of the spunbond machine and growth of mold or microorganisms detrimental to nonwoven use in hygiene and medical operations.

Another method of reducing static charge build up in the nonwoven fabric is to contact the web where the PLA is exposed on the surface of the fiber with a conductive static bar, which helps to ground the web, thereby dissipating charge build-up. However, this approach requires direct contact between the nonwoven web and the conductive substrate, and at such contact points there remains the possibility of direct discharge of static electricity through space with resulting possible harm to the operator, damage to equipment and risk of fire.

Advantageously, the inventors have discovered that fabrics comprising 100% PLA may be prepared at commercially viable processing speeds by positioning one or more ionization sources in close proximity to the nonwoven fabric. For example, in one embodiment, an ionization source 18 may be positioned near the spin beam 4 and the winder 16 to actively dissipate/neutralize static charge without contacting the fabric. As explained below, the ionization source exposes the nonwoven fabric to a stream of ions, which act to neutralize static charges in the nonwoven fabric. The stream of ions may include positive ions, negative ions, and combinations thereof.

In some embodiments, it may also be desirable to position a static control unit 20 near the calender 14. The static control unit 20 may be a passive static bar requiring contact with the fabric or an active ionization bar, which does not require contact with the fabric. Finally, an optional humidity unit 26 may be used in conjunction with the spin beam 4 and/or the press roll 12 to reduce static via added moisture.

In accordance with certain embodiments, for example, the first ionization source may be positioned above the collection surface and downstream of a point at where the PLA continuous filaments are deposited on the collection surface. However, in other embodiments, for instance, the first ionization source may be positioned between the outlet of the spin beam and the collection surface.

As discussed previously, the system may further comprise a press roll positioned downstream from the outlet of the spin beam. In this regard, the press roll may be configured to stabilize the web of the PLA continuous filaments by compressing said web before delivery of the PLA continuous fibers from the outlet of the spin beam towards the calender. In those embodiments including the press roll, for example, the first ionization source may be positioned downstream from the press roll. In other embodiments, for instance, the first ionization source may be positioned between the spin beam and the press roll.

In some embodiments and as shown in FIG. 3, the system may comprise a vacuum source 24 disposed below the collection surface for pulling the plurality of PLA continuous filaments from the outlet of the spin beam onto the collection surface before delivery to the calender.

Figure 4A:
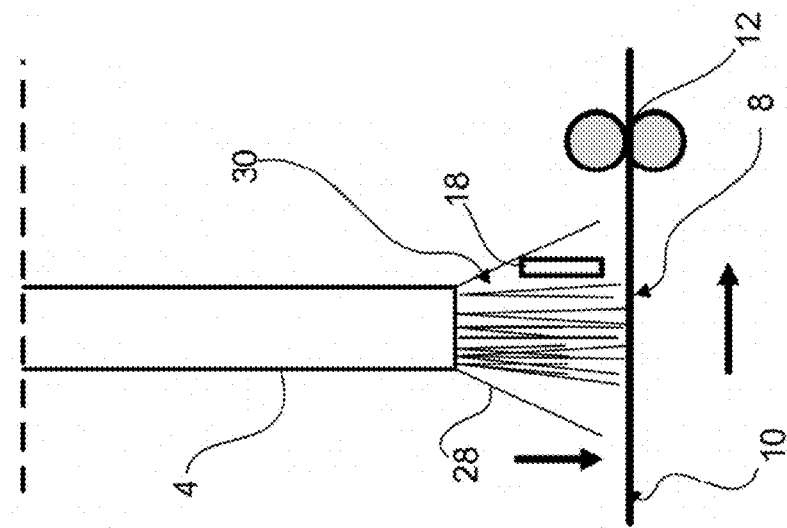
FIGS. 4A-4C are schematic diagrams illustrating positioning of the first ionization source in accordance with certain embodiments of the invention.
Figure 4B:
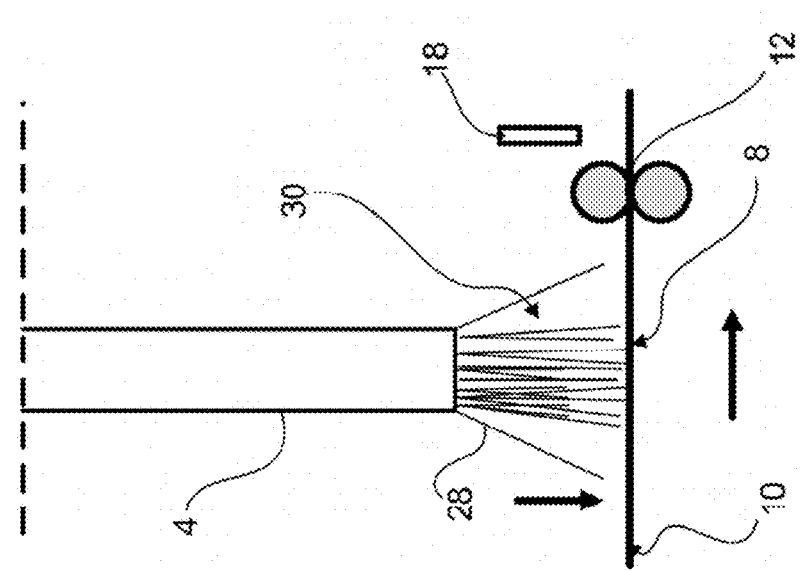
Figure 4C:
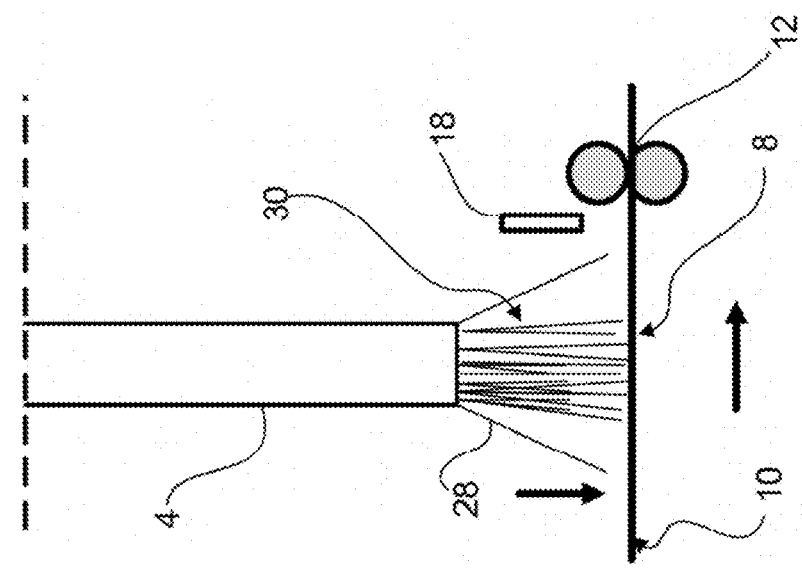

FIGS. 4A-4C, for example, are schematic diagrams illustrating positioning of the first ionization source in accordance with certain embodiments of the invention. As shown in FIG. 4A, the first ionization source 18 is positioned downstream of the outlet (i.e. diffuser) 28 of the spin beam 4 but upstream of the press roll 12. In FIG. 4B, however, the first ionization source 26 is positioned downstream of the press roll 12. In FIG. 2C, the first ionization source is positioned downstream of the point 8 at which the curtain of filaments 30 are deposited on the collection surface but also within the outlet 46.

Preferably, the ionization source comprises a device that is capable of actively discharging ions with the use of electrodes, ionizing air nozzles, ionizing air blowers, and the like. In one embodiment, the ionization source comprises an active discharge ionization bar that actively discharges ions in the direction of the nonwoven fabric. Examples of suitable ionization bars may include Elektrostatik Discharging Electrode E3412, which is available from Iontis.

In one embodiment, the ionization bar may extend over the web in the cross direction. Preferably, the ionization bar extends in the cross direction across the total width of the nonwoven fabric. In further embodiments, the ionization bar may extend under the web and the collection surface in the cross direction. However, positioning the ionization bar under the collection surface may be less effective than positioning the ionization bar over the web in the cross direction.

According to certain embodiments, for example, the first ionization source and the collection surface may be separated by a distance from about 1 inch to about 24 inches. In other embodiments, for instance, the first ionization source and the collection surface may be separated by a distance from about 1 inch to about 12 inches. In further embodiments, for example, the first ionization source and the collection surface may be separated by a distance from about 1 inch to about 5 inches. As such, in certain embodiments, the first ionization source and the collection surface may be separated by a distance from at least about any of the following: 1, 1.25, 1.5, 1.75, and 2 inches and/or at most about 24, 20, 16, 12, 10, 9, 8, 7, 6, and 5 inches (e.g., about 1.5-10 inches, about 2-8 inches, etc.).

In accordance with certain embodiments, for instance, the system may further comprise a static control unit positioned and arranged to dissipate static from the PLA spunbond nonwoven fabric proximate to the calender. In some embodiments, for example, the static control unit may be positioned upstream from, and adjacent to, the calender. In other embodiments, however, the static control unit may be positioned downstream from, and adjacent to, the calender.

In some embodiments, for instance, the static control unit may comprise a passive static bar. In such embodiments, the static control unit may contact the PLA spunbond nonwoven fabric in order to dissipate static charge. In other embodiments, however, the static control unit may comprise a second ionization source. As such, the second ionization source may actively dissipate static charge from the PLA spunbond nonwoven fabric such that contact by the second ionization source with the PLA spunbond nonwoven fabric is not required in order to dissipate the static charge.

According to certain embodiments, for example, the system may further comprise a winder positioned downstream from the calender. In such embodiments, for instance, the system may also include a third ionization source positioned and arranged to expose the PLA spunbond nonwoven fabric to ions proximate to the winder. In some embodiments, for example, at least one of the first ionization source, the static control source (e.g., the second ionization source), and the third ionization source may comprise an ionization bar. In this regard, for instance, the first ionization source, the static control source, and the third ionization source may be configured to actively dissipate static charge created during preparation of the PLA spunbond nonwoven fabric.

In accordance with certain embodiments, for example, the system may further comprise a humidity unit positioned within or downstream from the spin beam. In such embodiments, for instance, the humidity unit may comprise at least one of a steam unit, a fogging unit, a misting unit, or any combination thereof. In this regard, for example, humidity may be added in the spin beam during the formation of the plurality of PLA continuous filaments and/or near the press roll(s) (in those embodiments utilizing at least one press roll) in order to provide additional management of static charge that develops during the production of the PLA spunbond nonwoven fabric.

Nonwoven fabrics in accordance with embodiments of the invention may be used to prepare a variety of different structures. For example, in some embodiments, the inventive nonwoven fabric may be combined with one or more additional layers to prepare a composite or laminate material. Examples of such composites/laminates may include a spunbond composite, a spunbond-meltblown (SM) composite, a spunbond-meltblown-spunbond (SMS) composite, or a spunbond-meltblown-meltblown-spunbond (SMMS) composite. In some embodiments, composites may be prepared comprising a layer of the inventive nonwoven fabric and one or more film layers.

Figure 5A:
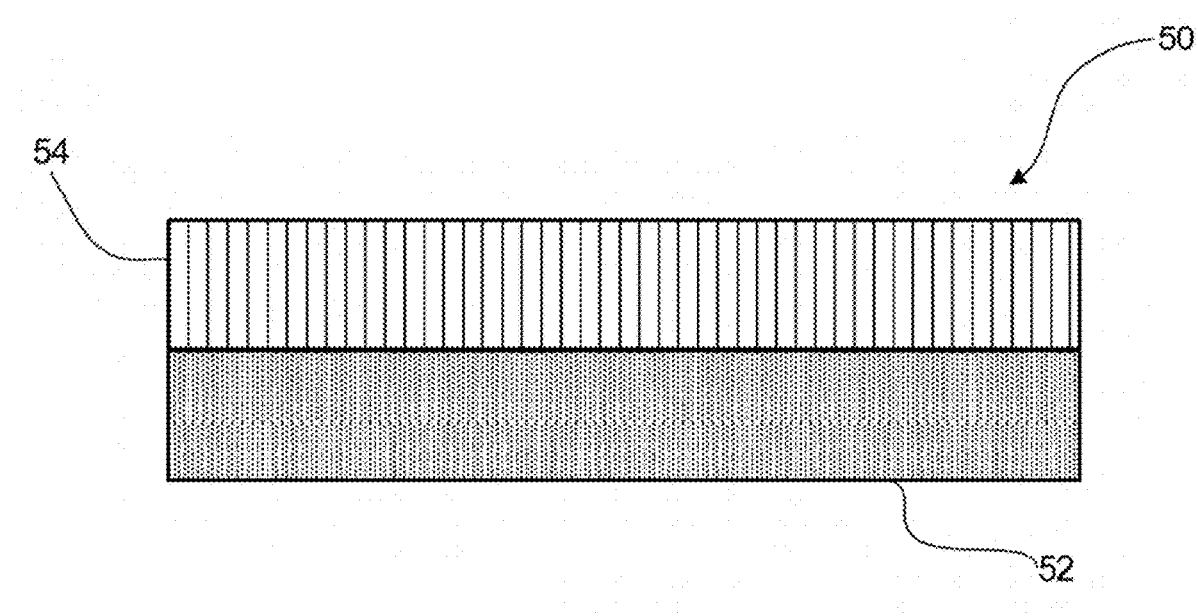
FIGS. 5A-5D are cross-sectional views of composites in accordance with certain embodiments of the invention.
Figure 5B:
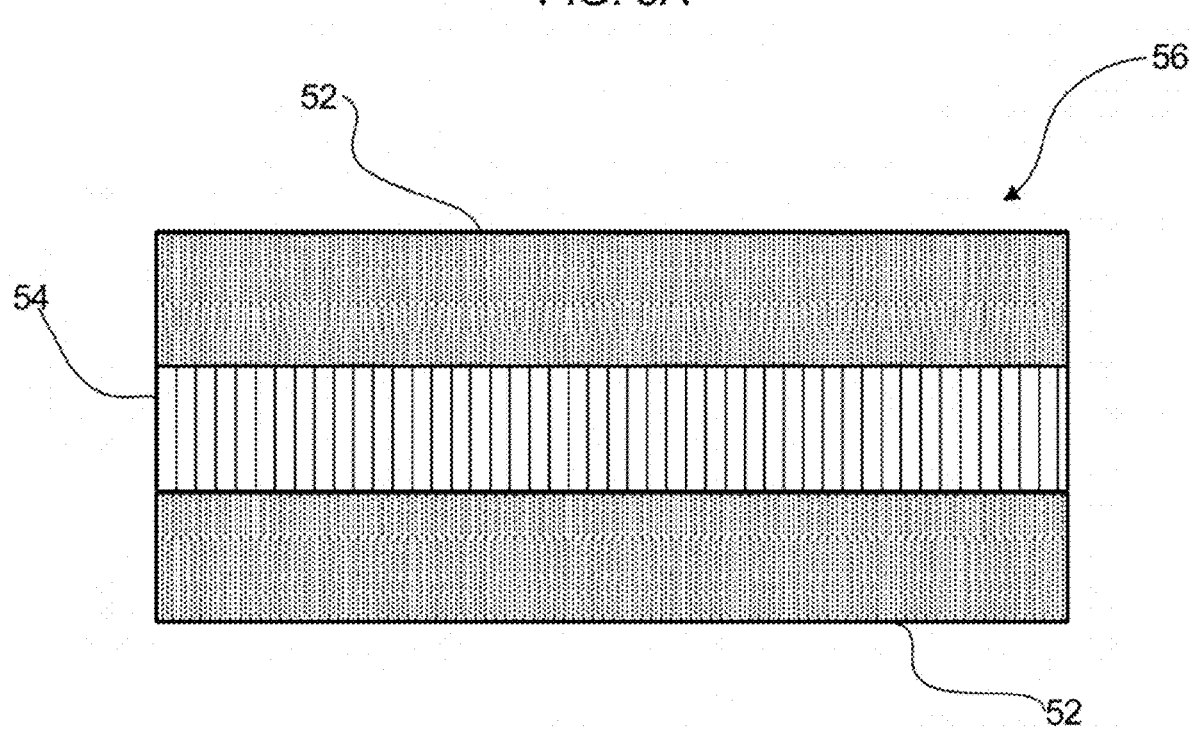
Figure 5C:
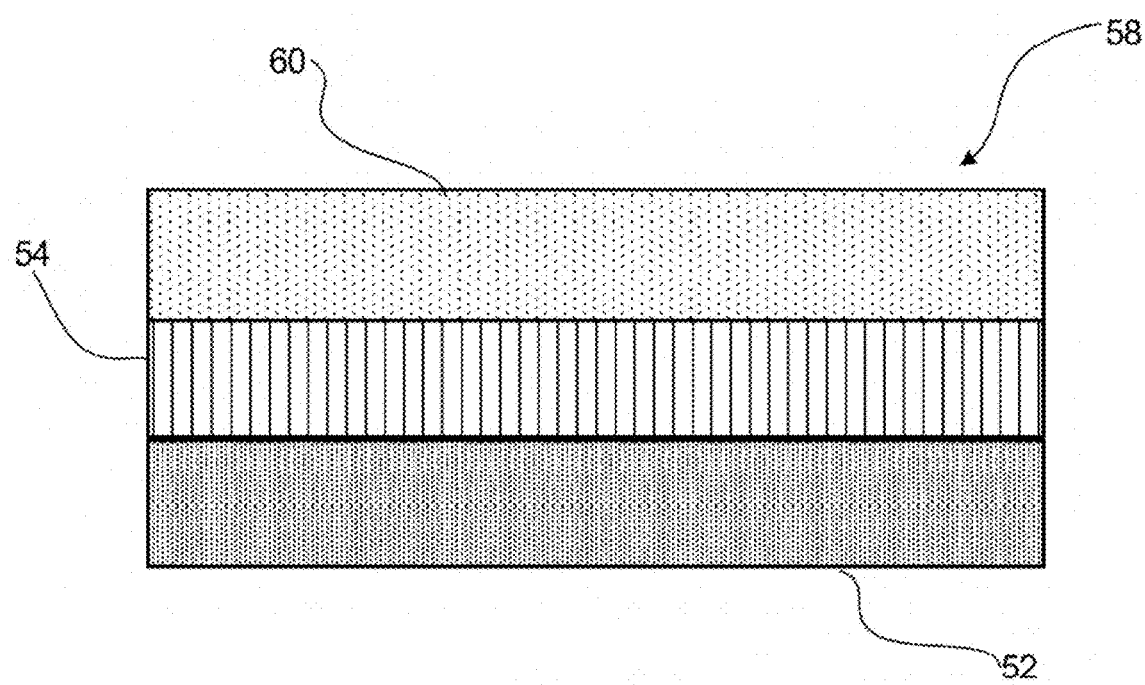
Figure 5D:
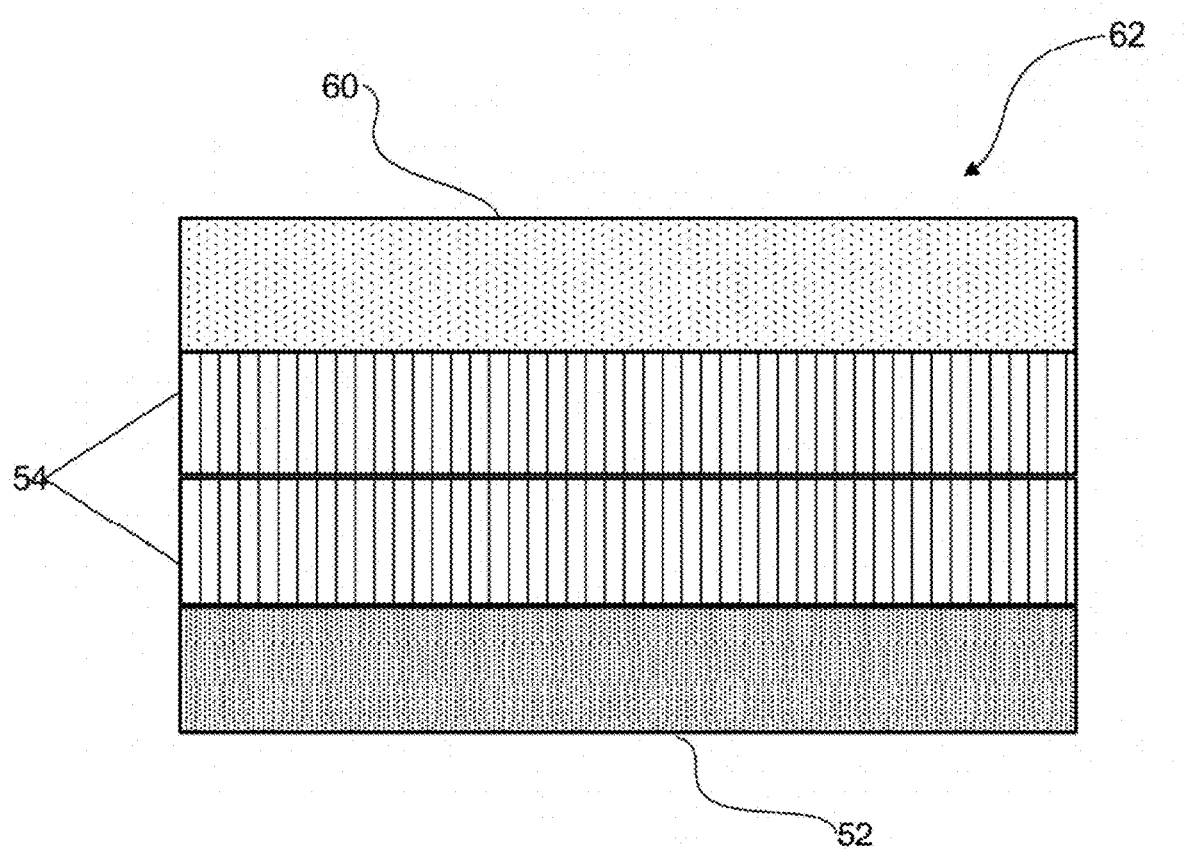

For example, FIGS. 5A-5D are cross-sectional views of composites in accordance with certain embodiments of the invention. For example, FIG. 5A illustrates a spunbond-meltblown (SM) composite 50 having a PLA spunbond nonwoven fabric layer 52 in accordance with embodiments of the present invention, and a meltblown layer 54. FIG. 5B illustrates a spunbond-meltblown-spunbond (SMS) composite 56 having two PLA spunbond nonwoven fabric layers 52 and a meltblown layer 54 sandwiched between the PLA spunbond nonwoven fabric layers 52. FIG. 5C illustrates an SMS composite 58 having a PLA spunbond nonwoven fabric layer 52, a different spunbond layer 60, and a meltblown layer 54 sandwiched between the two spunbond layers 52, 6. Finally, FIG. 4D illustrates a spunbond-meltblown-meltblown-spunbond (SMMS) composite 62 having a PLA spunbond nonwoven fabric layer 52, a different spunbond layer 60, and two meltblown layers 54 sandwiched between the two spunbond layers 52, 60. Although the SMMS composite 62 is shown as having two different spunbond layers 52 and 60, both spunbond layers may be the PLA spunbond nonwoven fabric layer 52.

In these multilayer structures, the basis weight of the PLA spunbond nonwoven fabric layer may range from as low as 7 g/m$^2$ and up to 150 g/m$^2$. In such multilayered laminates, both the meltblown and spunbond fibers could have PLA on the surface to insure optimum bonding. In some embodiments in which the spunbond layer is a part of a multilayer structure (e.g., SM, SMS, and SMMS), the amount of the meltblown in the structure may range from about 5 to 30%, and in particular, from about 5 to 15% of the structure as a percentage of the structure as a whole.

Multilayer structures in accordance with embodiments can be prepared in a variety of manners including continuous in-line processes where each layer is prepared in successive order on the same line, or depositing a meltblown layer on a previously formed spunbond layer. The layers of the multilayer structure can be bonded together to form a multilayer composite sheet material using thermal bonding, mechanical bonding, adhesive bonding, hydroentangling, or combinations of these. In certain embodiments, the layers are thermally point bonded to each other by passing the multilayer structure through a pair of calender rolls.

In yet another aspect, certain embodiments of the invention provide absorbent articles. In accordance with certain embodiments, the absorbent article may include a nonwoven fabric in accordance with the present invention. In one embodiment, a sustainable composite may be provided that includes at least two nonwoven fabric layers such that at least one nonwoven fabric layer may comprise a PLA spunbond nonwoven fabric layer in which a secondary alkane sulfonate is incorporated. The PLA spunbond nonwoven fabric layer may comprise a plurality of fibers such that PLA may be present at a surface of the plurality of fibers. In some embodiments, the absorbent article may be sustainable, but the sustainability of the absorbent article depends upon the other materials incorporated into the absorbent article other than the sustainable composite.

In this regard, fabrics prepared in accordance with embodiments of the invention may be used in wide variety of articles and applications. For instance, embodiments of the invention may be used for personal care applications, for example products for babycare (diapers, wipes), for femcare (pads, sanitary towels, tampons), for adult care (incontinence products), or for cosmetic applications (pads), agricultural applications, for example root wraps, seed bags, crop covers, industrial applications, for example work wear coveralls, airline pillows, automobile trunk liners, sound proofing, and household products, for example mattress coil covers and furniture scratch pads.

Figure 6A:
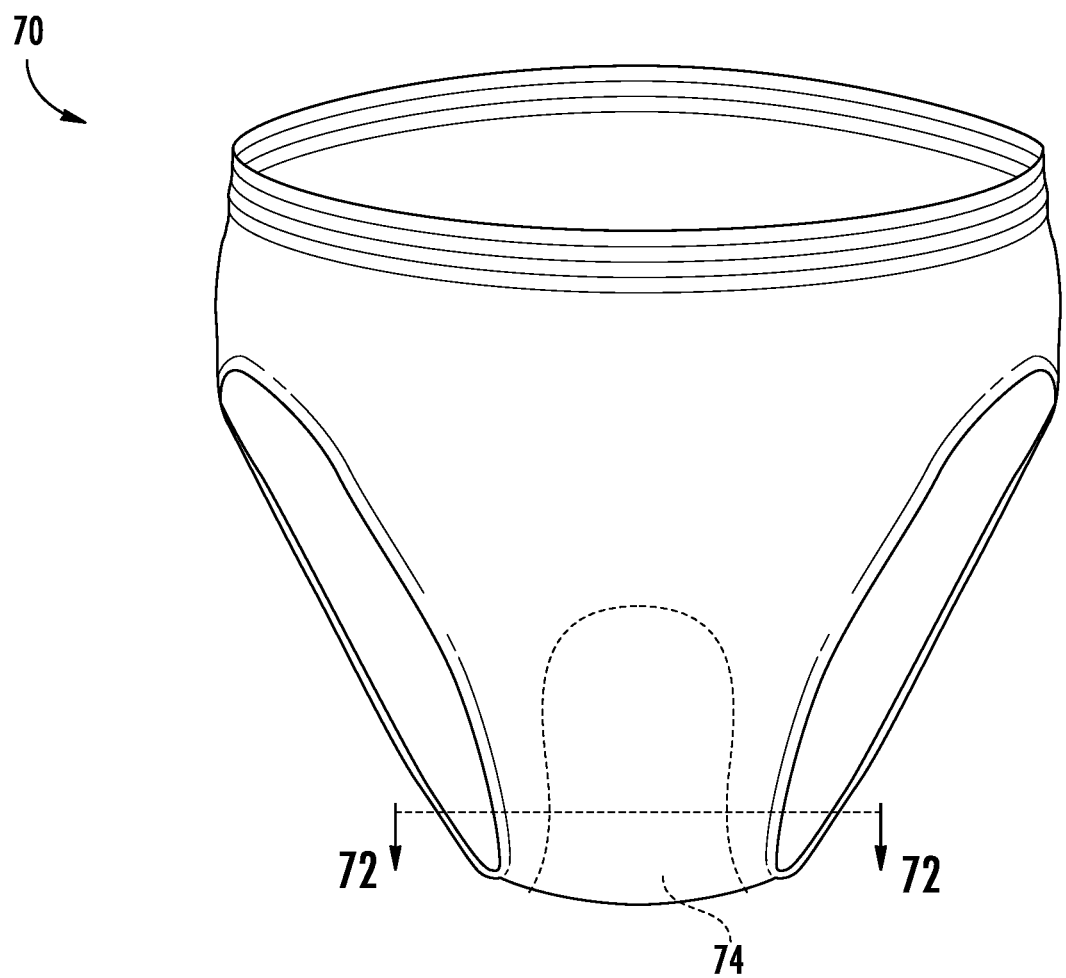
FIG. 6A is an illustration of an absorbent article in accordance with at least one embodiment of the invention.
Figure 6B:
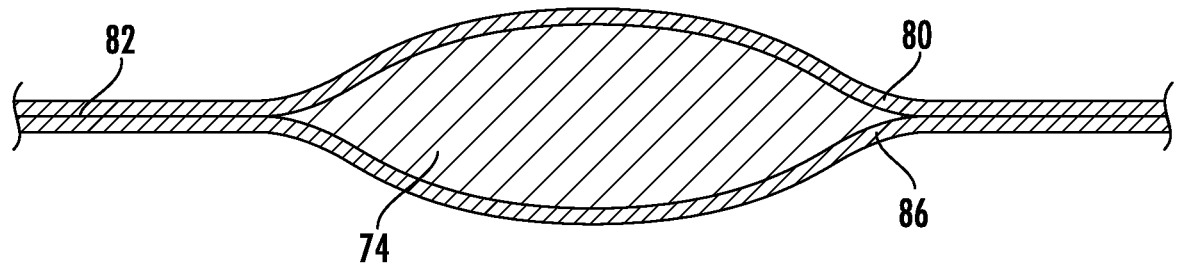
FIG. 6B is a cross-sectional view of the absorbent article of FIG. 6A taken along line 72-72 of FIG. 6A.

FIG. 6A, for example, is an illustration of an absorbent article (shown here as a diaper) in accordance with at least one embodiment of the invention and broadly designated by reference numeral 70. The diaper 70 may include an absorbent core 74. FIG. 6B is a cross-sectional view of the diaper 70 of FIG. 5A taken along line 72-72 of FIG. 5A. As shown in FIG. 6B, the absorbent core 74 may be sandwiched between a topsheet 80 and a backsheet 82. As further discussed herein, one or both of the topsheet 80 and the backsheet 82 may comprise a PLA spunbond nonwoven fabric and/or a sustainable composite including a PLA spunbond nonwoven fabric layer as previously discussed in more detail herein.

The topsheet 30 is positioned adjacent an outer surface of the absorbent core 74 and is preferably joined thereto and to the backsheet 82 by attachment means (not shown) such as those well known in the art. For example, the topsheet 80 may be secured to the absorbent core 74 by a uniform continuous layer of adhesive, a patterned layer of adhesive, or an array of separate lines, spirals, or spots of adhesive.

As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. In a preferred embodiment of the present invention, the topsheet 80 and the backsheet 82 are joined directly to each other in the diaper periphery 86 and are indirectly joined together by directly joining them to the absorbent core 74 by the attachment means (not shown).

Preferably, the topsheet 80 is compliant, soft feeling, and non-irritating to the wearer's skin. Further, the topsheet 80 is liquid pervious permitting liquids (e.g., urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), or a combination of natural and synthetic fibers.

In some embodiments, the topsheet may be treated with a surfactant to help ensure proper liquid transport through the topsheet and into the absorbent core. An example of a suitable surfactant is available from Momentive Performance Materials under the tradename NUWET™ 237.

In one embodiment, at least one of the topsheet and backsheet comprises a nonwoven fabric comprising PLA continuous filaments that includes a secondary alkaline sulfonate as discussed previously.

In a preferred embodiment, the topsheet comprises at least 75 weight percent of bio-based materials, such as at least 75 weight percent of the inventive PLA spunbond nonwoven fabric. Additional examples of bio-based polymers that may be used in embodiments of the invention include polymers directly produced from organisms, such as polyhydroxyalkanoates (e.g., poly(beta-hydroxyalkanoate), poly(3-hydroxybutyrate-co-3-hydroxyvalerate, NODAX™), and bacterial cellulose; polymers extracted from plants and biomass, such as polysaccharides and derivatives thereof (e.g., gums, cellulose, cellulose esters, chitin, chitosan, starch, chemically modified starch), proteins (e.g., zein, whey, gluten, collagen), lipids, lignins, and natural rubber; and current polymers derived from naturally sourced monomers and derivatives, such as bio-polyethylene, bio-polypropylene, polytrimethylene terephthalate, polylactic acid, NYLON 11, alkyd resins, succinic acid-based polyesters, and bio-polyethylene terephthalate.

There are a number of manufacturing techniques which may be used to manufacture the topsheet 80. For example, the topsheet 80 may be a nonwoven web of fibers. When the topsheet comprises a nonwoven web, the web may be spunbonded, carded, wet-laid, meltblown, hydroentangled, combinations of the above, or the like. A preferred topsheet comprises a spunbond nonwoven fabric in which the fibers are thermally bonded to each other to form a coherent web.

The backsheet 82 is positioned adjacent to an opposite surface of the absorbent core 74 and is preferably joined thereto by attachment mechanisms (not shown) such as those well known in the art. Suitable attachment mechanisms are described with respect to joining the topsheet 80 to the absorbent core 74. Alternatively, the attachment means may comprise heat bonds, pressure bonds, ultrasonic bonds, dynamic mechanical bonds, or any other suitable attachment means or combinations of these attachment mechanisms as are known in the art.

The backsheet 82 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 82 prevents the exudates absorbed and contained in the absorbent core 74 from wetting articles which contact the diaper 70 such as bedsheets and undergarments. The backsheet 82 may thus comprise a woven or nonwoven material, polymeric films such as thermoplastic films, or composite materials such as a film-coated nonwoven material.

In some embodiments, material for the backsheet may include the bio-based polymers discussed previously, and in particular, the inventive PLA spunbond fabric described herein. In some embodiments, the backsheet may include additional bio-based polymers. For example, bio-based polymers for use in the backsheet may include polymers directly produced from organisms, such as polyhydroxyalkanoates (e.g., poly(beta-hydroxyalkanoate), poly(3-hydroxybutyrate-co-3-hydroxyvalerate, NODAX™), and bacterial cellulose; polymers extracted from plants and biomass, such as polysaccharides and derivatives thereof (e.g., gums, cellulose, cellulose esters, chitin, chitosan, starch, chemically modified starch), proteins (e.g., zein, whey, gluten, collagen), lipids, lignins, and natural rubber; and current polymers derived from naturally sourced monomers and derivatives, such as bio-polyethylene, bio-polypropylene, polytrimethylene terephthalate, polylactic acid, NYLON 11, alkyd resins, succinic acid-based polyesters, and bio-polyethylene terephthalate.

In one embodiment, the backsheet may comprise a laminate structure having a liquid impervious film layer that is joined to a nonwoven web. Suitable films may be prepared from the bio-based polymers as previously discussed. In one example, the film may comprise a sugar cane derived polyethylene polymer, such as a film grade LDPE polyethylene grade SEB853/72 or SPB681/59 recommended by Braskem S.A. for lamination. Suitable films may also include additives such as $CaCO_3$ to improve film breathability while still maintaining fluid barrier properties. In some embodiments, the backsheet layer may comprise a laminate structure having a bio-based film layer, such as those discussed previously, that is laminated to a fabric layer having a spunbond-meltblown-spunbond (SMS) structure.

The absorbent core 74 may comprise any material that is capable of absorbing fluids and exudates. Preferably, the absorbent core comprises at least 75% by weight of bio-based materials. In one embodiment, materials for the core wrap may comprise a fabric layer comprising a spunbond fabric, spunbond-meltblown fabric (SM), or an SMS fabric. An example of a core wrap comprising an SMS fabric comprises a spunbond nonwoven layer comprising bicomponent fibers having a PLA sheath (e.g., Nature Works PLA Grade PLA 6752 with 4% D Isomer), and a PLA core (e.g. NatureWorks Grade 6202 with 2% D Isomer). In one embodiment, the meltblown layer of the SMS fabric may be comprised of a PLA meltblown fibers (e.g., NatureWorks PLA grade 6252).

Figure 7:
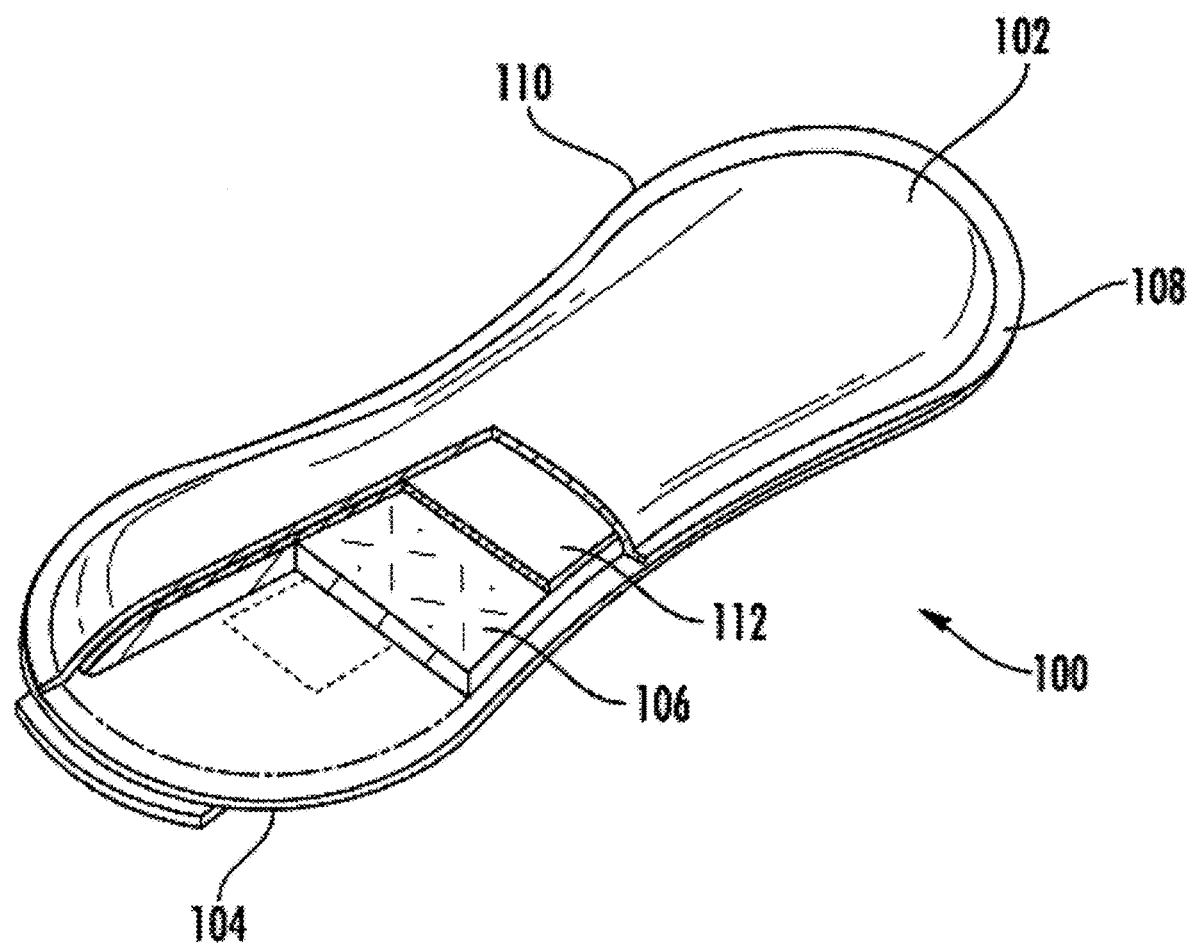
FIG. 7 is an illustration of an absorbent article in accordance with at least one embodiment of the invention in which the absorbent article is in the form of a feminine sanitary pad.

FIG. 7 is an illustration of an absorbent article in accordance with at least one embodiment of the invention in which the absorbent article is in the form of a feminine sanitary pad broad designated by reference numeral 100. Pad 100 may include a topsheet 102, backsheet 104, and an absorbent core 106 disposed there between. Preferably, topsheet 102 and backsheet 104 are joined to each other about along opposing outer edges to define a continuous seam 108 that extends about the periphery 110 of the pad 100. Continuous seam 108 may comprise a heat seal that is formed from thermally bonding the topsheet and backsheet to each other. In other embodiments, continuous seam 108 is formed by adhesively bonding the topsheet and backsheet to each other.

As in the embodiments discussed above, pad 100 preferably comprises a nonwoven fabric in accordance with the present invention. That is a spunbond nonwoven fabric comprising fibers that are a blend of a PLA resin and a secondary alkaline sulfonate.

In some embodiments, the pad 100 may comprise a sustainable articles comprising a bio-based material content of at least 75 weight percent, based on the total weight of the pad, such as comprising a bio-based material content that is at least 80%, 85%, 90%, or 95% by weight of the pad. Suitable materials for the topsheet, backsheet, and absorbent core are discussed previously.

In some embodiments, pad 100 may also include a fluid acquisition layer 112 that is disposed between the absorbent core 106 and the topsheet 102. In one embodiment a fluid acquisition layer could be made by carding a web comprised of a blend of 7 denier hollow PLA-Type 820 2 inch cut length staple fibers plus 3 denier Solid PLA—Type 821 2 inch cut length staple fibers, (both available from Fiber Innovations Technology—Johnson City, Tenn.); treating the resulting carded web via kiss roll with a suspension of cooked starch (for example type STABITEX 65401 from Cargill); exposing the resulting web of fiber and starch to elevated temperature via a combination of hot air and contact to heated dryer cans to cure and dry the web, and winding and slitting the resulting roll in to child rolls for use in the absorbent article.

Various components of the absorbent article are typically joined via thermal or adhesive bonding. When an adhesive is employed, the adhesive preferably comprises a bio-based adhesive. An example of a bio-based adhesive is a pressure sensitive adhesive available from Danimer Scientific under the product code 92721.

In accordance with certain embodiments, for example, at least the PLA spunbond nonwoven fabric layer may comprise bicomponent fibers. In some embodiments, for instance, the bicomponent fibers may comprise a side-by-side arrangement. However, in other embodiments, for example, the bicomponent fibers may comprise a sheath and a core. In further embodiments, for instance, the bicomponent fibers may comprise reverse bicomponent fibers. In certain embodiments, for example, the sheath may comprise PLA. In further embodiments, for instance, the core may comprise at least one of a polyolefin, a polyester, or any combination thereof. In some embodiments, for example, the core may comprise at least one of a polypropylene, a polyethylene, a polyethylene terephthalate, PLA, or any combination thereof. In certain embodiments, for instance, each of the sheath and the core may comprise PLA.

According to certain embodiments, for example, the sheath may comprise a first PLA grade, the core may comprise a second PLA grade, and the first PLA grade and the second PLA grade may be different. In some embodiments, for instance, the first PLA grade may comprise up to about 5% crystallinity, and the second PLA grade may comprise from about 40% to about 50% crystallinity. In other embodiments, for example, the first PLA grade may comprise a melting point from about 125° C. to about 135° C., and the second PLA grade may comprise a melting point from about 155° C. to about 170° C. In further embodiments, for instance, the first PLA grade may comprise a weight percent of D isomer from about 4 wt. % to about 10 wt. %, and the second PLA grade may comprise a weight percent of D isomer of about 2 wt. %. In some embodiments, for example, the bicomponent fibers may comprise about 70 wt. % core and about 30 wt. % sheath.

However, in other embodiments, for instance, at least the PLA spunbond nonwoven fabric layer may comprise a plurality of monocomponent PLA fibers comprising a blend of a PLA resin and a secondary alkane sulfone.

In a preferred embodiment, the PLA nonwoven fabric in accordance with the present invention may be used to manufacture sustainable absorbent articles. Examples of sustainable absorbent articles may be found in U.S. patent application Ser. No. 14/839,026 to Chester et al., incorporated fully by referenced herein.

In accordance with certain embodiments, for example, at least the PLA spunbond nonwoven fabric layer may comprise a three-dimensional geometric bonding pattern. In such embodiments, for instance, the bonding pattern may comprise at least one of a diamond pattern, a hexagonal dot pattern, an oval-elliptic pattern, a rod-shaped pattern, or any combination thereof.

EXAMPLES

The following examples are provided for illustrating one or more embodiments of the present invention and should not be construed as limiting the invention.

Nonwoven fabrics in accordance with the invention were prepared via a Reifenhaeuser Reicofil-3 line or Reicofil-4 line. Each of the examples were prepared using the setup described in Example 1 unless otherwise indicated. Moreover, unless otherwise indicated all percentages are weight percentages. The materials used in the examples are identified below.

Test Methods

Titer was calculated from microscopic measurement of fiber diameter and known polymer density per German textile method C-1570.

Basis Weight was determined generally following the German textile method CM-130 from the weight of 10 layers of fabric cut into 10×10 cm squares.

Tensile was determined in accordance with Method 10 DIN 53857 using a sample with 5 cm width, 100 mm gauge length, and cross-head speed of 200 mm/min. Tensile strengths were measured at peak.

Elongation was determined in accordance with Method 10 DIN 53857 using a sample with 5 cm width, 100 mm gauge length, and cross-head speed of 200 mm/min. Elongations were measured at peak.

Fabric Shrinkage was determined by cutting three samples taken across the web width of nominal dimensions of MD of 29.7 cm and CD of 21.0 cm; measuring the actual MD and CD width at three locations in the sheet; placing the sample in water heated to 60 C for 1 minute; and remeasuring the MD and CD dimensions at the above three locations. The average width measurement after exposure divided by the original measurement X 100% yielded the % Shrinkage. A low % shrinkage value suggests that the continuous fibers comprising PLA have been spun and drawn at sufficient speed to yield after bonding a high strength stable fabric.

Comparative Examples 1, 2, and 3

In Comparative Examples 1, 2 and 3 a 100% PLA bicomponent fabric was prepared on a Reicofil-4 beam. A press roll (R-4 press roll) was positioned on the collection surface downstream of where the filaments are deposited on the collection surface. An Ionis Elektrostatik Discharging Electrode E3412 (i.e. ionization bar) was positioned above and extending over the collection surface in the cross direction and placed approximately 1 to 3 inches above the collection surface and 2 to 3 inches downstream of the R-4 press roll.

The fabrics were bicomponent 30/70 NatureWorks Grade 6752/NatureWorks Grade 6202/sheath/core made with ionization bars positioned as discussed above to minimize static. The fabrics of Comparative Examples 1, 2 and 3 were produced at spin beam temperatures of 235° C. at the extruder and 240° C. at the die. The fabric of Comparative Example 1 was produced at a fiber draw speed of 3600 m/min and a line speed of 145 m/min. The calender for Comparative Example 1 had calender temperatures of 160° C. for the pattern roll and 147° C. for the anvil roll and a calender pressure of 40 N/mm.

The fabric of Comparative Example 2 was produced using a fiber draw speed of 3800 m/min and a line speed of 90 m/min. The calender for Comparative Example 2 had calender temperatures of 160° C. for the pattern roll and 147° C. for the anvil roll and a calender pressure of 40 N/mm.

The fabric of Comparative Example 3 was produced using a fiber draw speed of 3200 m/min and a line speed of 145 m/min. The calender for Comparative Example 3 had calender temperatures of 160° C. for the pattern roll and 147° C. for the anvil roll and a calender pressure of 40 N/mm. Mechanical properties of Comparative Examples 1, 2, and 3 are summarized in Tables 4 and 5 below.

Inventive Example 1

In Inventive Example 1, a 100% PLA bicomponent fabric having a sheath/core structure was prepared in which 2 weight percent of a masterbatch comprising a PLA resin and a secondary alkane sulfonate was added to the polymer component defining the sheath. The setup of the system is the same as described above for Comparative Examples 1, 2, and 3.

The fabric was a bicomponent 30/70 NatureWorks Grade 6752/NatureWorks Grade 6202/sheath/core made with ionization bars as discussed above to minimize static. At the sheath extruder, 2% by weight of a masterbatch of Sukano Antistatic Product S 546 was combined with NatureWorks Grade 6752 to provide the sheath of the bicomponent fibers. BICO. The fabric of Inventive Example 1 was produced at spin beam temperatures of 235° C. at the extruder and 240° C. at the die. The fabric of Inventive Example 1 was produced at a fiber draw speed of 3800 m/min and a line speed of 145 m/min. The calender for Inventive Example 1 had calender temperatures of 160° C. for the pattern roll and 147° C. for the anvil roll and a calender pressure of 40 N/mm. Properties of Inventive Example 1 are summarized in Tables 4 and 5 below.

Inventive Example 2

In Inventive Example 2, a 100% PLA bicomponent fabric having a sheath/core arrangement was prepared in which 3 weight percent of a masterbatch comprising a PLA resin and a secondary alkane sulfonate was added to the polymer component defining the sheath. The setup of the system is the same as described above for Comparative Examples 1, 2, and 3.

The fabric was a bicomponent 30/70 NatureWorks Grade 6752/NatureWorks Grade 6202/sheath/core made with ionization bars as discussed above to minimize static. At the sheath extruder, 3% by weight of a masterbatch of Sukano Antistatic Product S 546 was combined with NatureWorks Grade 6752 to provide the sheath of BICO Example 12. The fabric of Inventive Example 2 was produced at spin beam temperatures of 235° C. at the extruder and 240° C. at the die. The fabric of Inventive Example 2 was produced at a fiber draw speed of 3550 m/min and a line speed of 145 m/min. The calender for Inventive Example 2 had calender temperatures of 160° C. for the pattern roll and 147° C. for the anvil roll and a calender pressure of 40 N/mm. Properties of Inventive Example 2 are summarized in Tables 4 and 5 below.

Inventive Example 3

In Inventive Example 3, a 100% PLA bicomponent fabric having a sheath/core arrangement was prepared in which 2 weight percent of a masterbatch comprising a PLA resin and a secondary alkane sulfonate was added to the polymer component defining the sheath. The setup of the system is the same as described above for Comparative Examples 1, 2, and 3.

The fabric was bicomponent 30/70 NatureWorks Grade 6752/NatureWorks Grade 6202/sheath/core made with ionization bars as discussed above to minimize static. At the sheath extruder, 2% by weight of a masterbatch of Sukano Antistatic Product S 546 was combined with NatureWorks Grade 6752 to provide the sheath of the fabric. The fabric was produced at spin beam temperatures of 235° C. at the extruder and 240° C. at the die. The fabric was produced at a fiber draw speed of 3400 m/min and a line speed of 90 m/min. The calender for Inventive Example 3 had calender temperatures of 160° C. for the pattern roll and 147° C. for the anvil roll and a calender pressure of 40 N/mm. Properties of Inventive Example 3 are summarized in Tables 4 and 5 below.

Inventive Example 4

In Inventive Example 4, a 100% PLA bicomponent fabric having a sheath/core arrangement was prepared in which 2 weight percent of a masterbatch comprising a PLA resin and a secondary alkane sulfonate was added to the polymer component defining the sheath. The setup of the system is the same as described above for Comparative Examples 1, 2, and 3.

The fabric was a bicomponent 30/70 NatureWorks Grade 6752/NatureWorks Grade 6202/sheath/core made with ionization bars as discussed above to minimize static. At the sheath extruder, 2% by weight of a masterbatch of Sukano Antistatic Product S 546 was combined with NatureWorks Grade 6752 to provide the sheath of bicomponent fabric. The fabric of Inventive Example 4 was produced at spin beam temperatures of 235° C. at the extruder and 240° C. at the die. The fabric of Inventive Example 4 was produced at a fiber draw speed of approximately 3400 m/min and a line speed of 241 m/min to yield a calculated basis weight of 15 grams/square meter. The calender for Inventive Example 4 had calender temperatures of 160° C. for the pattern roll and 147° C. for the anvil roll and a calender pressure of 40 N/mm. The mechanical properties of Inventive Example 14 were not evaluated.

TABLE 4

| | | | | Nonwoven Mechanical Properties | | | | | | |
|---|---|---|---|---|---|---|---|---|---|---|
| | | Titer | Basis Weight | MD Tensile | MD Tensile per Basis Weight | CD Tensile | CD Tensile per Basis Weight | MD % Elong. | CD % Elong. | MD Toughness Index | CD Toughness Index |
| | | | | | Units | | | | | | |
| Example | | DTEX | g/m$^2$ | N/5 cm | N-m$^2$/g-5 cm | N/5 cm | N-m$^2$/g-5 cm | % | % | N-% | N-% |
| Comparative Example 1 | | 1.8 | 23.8 | 35.1 | 1.47 | 13.0 | 0.546 | 13.3 | 24.03 | 467 | 312 |
| Comparative Example 2 | | 1.7 | 39.8 | 70.7 | 1.78 | 26.6 | 0.668 | 14.7 | 28.61 | 1881 | 761 |
| Comparative Example 3 | | 2.0 | 24.3 | 38.4 | 1.58 | 14.8 | 0.609 | 15.6 | 26.30 | 599 | 389 |
| Inventive Example 1 | | 1.7 | 27.6 | 83.2 | 3.01 | 29.0 | 1.051 | 28.3 | 44.28 | 2355 | 1284 |
| Inventive Example 2 | | 1.8 | 27.6 | 85.2 | 3.09 | 29.0 | 1.051 | 29.4 | 49.44 | 2505 | 1434 |
| Inventive Example 3 | | 1.9 | 51.3 | 142.2 | 2.77 | 73.8 | 1.435 | 40.8 | 46.54 | 5802 | 3435 |
| Inventive Example 4 | | — | 15.0* | — | — | — | — | — | — | — | — |

*Calculated basis weight for sample produced.

TABLE 5

Properties Normalized for Basis Weights.

| Example | Basis Weight | MD Tensile per Basis Weight | CD Tensile per Basis Weight | MD Toughness Index (MDTI) | CD Toughness Index (CDTI) | MD Relative Toughness Index per Basis Weight | CD Relative Toughness Index per Basis Weight | Fabric Root mean Square Toughness index per Basis Weight* |
|---|---|---|---|---|---|---|---|---|
| Units | g/m$^2$ | N-m$^2$/g-5 cm | N-m$^2$/g-5 cm | N-% | N-% | N-%/g/m$^2$ | N-%/g/m$^2$ | N-%/g/m$^2$ |
| Comparative Example 1 | 23.8 | 1.47 | 0.546 | 467 | 312 | 19.62 | 13.11 | 16.69 |
| Comparative Example 2 | 39.8 | 1.78 | 0.668 | 1881 | 761 | 47.26 | 19.12 | 36.05 |
| Comparative Example 3 | 24.3 | 1.58 | 0.609 | 599 | 389 | 24.65 | 16.01 | 20.78 |
| Inventive Example 1 | 27.6 | 3.01 | 1.051 | 2355 | 1284 | 85.32 | 46.52 | 68.12 |
| Inventive Example 2 | 27.6 | 3.09 | 1.051 | 2505 | 1434 | 90.76 | 51.96 | 73.95 |
| Inventive Example 3 | 51.3 | 2.77 | 1.435 | 5802 | 3435 | 113.1 | 66.96 | 92.94 |

*Root Mean Square = $\sqrt{\dfrac{(MDTI)^2 + (CDTI)^2}{2}}$ ;

Fabric Root mean Square Toughness Index Per Basis Weight = $\left(\sqrt{\dfrac{(MDTI)^2 + (CDTI)^2}{2}}\right) /$ Basis Weight

TABLE 6

Percent Increase in MD and CD Relative Index in Toughness

| Example | Inventive Example 1 (MD) | Inventive Example 2 (MD) | Inventive Example 3 (MD) | Inventive Example 1 (CD) | Inventive Example 2 (CD) | Inventive Example 3 (CD) |
|---|---|---|---|---|---|---|
| Units | (%) | (%) | (%) | (%) | (%) | (%) |
| Comparative Example 1 | 334.9 | 362.6 | 476.5 | 254.8 | 296.3 | 410.7 |
| Comparative Example 2 | 80.5 | 92.0 | 139.3 | 143.3 | 171.6 | 250.2 |
| Comparative Example 3 | 246.1 | 268.2 | 358.8 | 190.6 | 224.5 | 318.2 |

Percent Increase: (ending value − starting value)/starting value × 100

TABLE 7

Shrinkage Resistance for PLA Spunbond Fabric

| Example | Shrink (MD) % | Shrink (CD) % | Area Shrink % |
|---|---|---|---|
| Comparative Example 1 | 3.1 | −1.1 | 2.1 |
| Comparative Example 2 | 3.1 | −1.4 | 1.8 |
| Comparative Example 3 | 2.9 | −1.5 | 1.4 |
| Inventive Example 1 | 7.8 | −0.9 | 7.0 |
| Inventive Example 2 | 6.4 | −2.5 | 4.0 |
| Inventive Example 3 | 2.2 | −3.3 | −1.0 |

From Tables 4 and 5 above, it can be seen that the inventive nonwoven fabrics exhibit significant improvements in mechanical properties in comparison to the identically prepared nonwoven fabrics that do not include the secondary alkane sulfonate. In this regard, the results provided in Table 5 are particularly telling. In Table 5, the results have been normalized to account for the differences in basis weights. Based on this data, it can be seen that the inventive nonwoven fabrics exhibited an increase in tensile strengths of greater than 50% in comparison to the comparative examples. For example, the inventive nonwoven fabrics exhibited an increase in MD tensile strength ranging from 55.6% (comparison of Inventive Example 3 and Comparative Example 2) to 110.2% (comparison of Inventive Example 2 and Comparative Example 1). For CD tensile strength, the inventive nonwoven fabrics exhibited an increase in CD tensile strength ranging from 57.3% (comparison of Inventive Example 1 and Comparative Example 2) to 162.8% (comparison of Inventive Example 3 and Comparative Example 1).

The inventive nonwoven fabrics also exhibited significant increases in toughness in comparison to the nonwoven fabrics of the comparative examples. Table 5 below shows both MD and CD Relative Index of Toughness (normalized for basis weight) for Comparative Examples 1-3 and Invention Examples 1-3. For example, the inventive nonwoven fabrics exhibited an increase in MD Relative Index of Toughness ranging from 80.5% (comparison of Inventive Example 1 and Comparative Example 2) to 476% (comparison of Inventive Example 3 and Comparative Example 1). For the CD Relative Index of Toughness, the inventive nonwoven fabrics exhibited an increase in CD Relative Index of Toughness ranging from 143% (comparison of Inventive Example 1 and Comparative Example 2) to 411% (comparison of Inventive Example 3 and Comparative Example 1).

When comparing properties of different nonwovens it is often useful to compare the root mean square of the combined values of the MD and CD property of interest. This method allows comparison of single values. The root mean square provides a single number that combines input from both the MD and the CD values by taking the square root of the sum of the square of the MD value plus the square of the CD value. Use of the root mean square method to combine the MD and the CD results is particularly useful if samples to be compared were made on different machines or under some different condition that might influence the MD/CD ratio. Table 5 below shows the root mean square of the Toughness Index per basis weight for the Comparative Samples 1-3 as well as the Invention samples 1-3. The Root Mean Square Toughness Index values normalized for basis weight show the comparative samples grouped between 10 and 40 N-%/g/m$^2$. In contrast, the inventive nonwoven fabrics exhibited Root Mean Square Toughness Index values above 65 N-%/g/m$^2$, and in particular, within a range of 55 to 100 N-%/g/m$^2$. Thus, a very clear separation in the root mean square of the normalized Index of Toughness values can be seen for fabrics of the invention and the comparative samples.

To further evaluate the basis for the increases in tensile strengths, elongation, and toughness of the inventive nonwoven fabrics, SEM images of the fabric surfaces of Comparative Example 1 and Inventive Example 1 were obtained. FIGS. 1A and 1B are SEM images of Comparative Example 1 taken at a magnification of 250× and 100×, respectively. FIGS. 2A and 2B are SEM images of Inventive Example 1 taken at a magnification of 250× and 100×, respectively. The images were obtained with a PERSONAL SEM 75, available from RJ Lee Instruments Ltd., and a DESK V Sputterer, available from Denton Vacuum. As the SEM images were made at low magnification, 100× and 250×, sputtering with gold was not required. 5 mm×5 mm samples of each fabric were obtained and placed with in the SEM instrument. A low vacuum was obtained, and then the images were captured.

Surprisingly, a significant difference in bonding between the fibers was observed. In particular, the bond points of the fabric of Comparative Example 1 showed that the individual fibers were loosely bonded together, and that there was minimal polymer flow bonding adjacent fibers to each other. In comparison, the bond points of the fabric of Inventive Example 1, showed significant melting and flowing of the polymer of the individual fibers. Thus, the inventive fabric exhibited significant improvements in bonding in comparison to the comparative fabric that did not include the secondary alkane sulfonate.

In the following examples, the effect of the carrier resin for the secondary alkane sulfonate on the physical properties was explored. As explained below, the improvements in mechanical properties in the fabrics were shown to be due primarily to the presence of the secondary alkane sulfonate, and not to the presence of a lower molecular weight carrier resin in the masterbatch.

Comparative Example 4

In Comparative Example 4, a 100% PLA bicomponent fabric having a sheath/core arrangement was prepared in which 0.5% weight percent of NatureWorks Grade 6302 was added to the polymer component defining the sheath. NatureWorks Grade 6302 is commonly used as the carrier polymer for masterbatches added to PLA polymer formulations. It is therefore believed that this PLA resin provides a good approximation of the PLA resin in the secondary alkane sulfonate. The setup of the system is the same as described above for Comparative Examples 1, 2, and 3.

The fabric was a bicomponent 30/70 NatureWorks Grade 6752/NatureWorks Grade 6202/sheath/core made with ionization bars as discussed above to minimize static. At the sheath extruder, 0.5% weight percent of NatureWorks Grade 6302 2% by weight was combined with NatureWorks Grade 6752 to provide the sheath of bicomponent fabric. The fabric of Comparative Example 4 was made at processing conditions similar to those used for Inventive Examples 1-4, with the exceptions as shown in Table 8 below and the line speed was adjusted to provide a final basis weight of 25 GSM. Properties of Comparative Example 4 are summarized below in Table 9, below.

Comparative Example 5

In Comparative Example 5 a 100% PLA bicomponent fabric having a sheath/core arrangement was prepared in which 1.0% weight percent of NatureWorks Grade 6302 was added to the polymer component defining the sheath. The setup of the system is the same as described above for Comparative Examples 1, 2, and 3.

The fabric was a bicomponent 30/70 NatureWorks Grade 6752/NatureWorks Grade 6202/sheath/core made with ionization bars as discussed above to minimize static. At the sheath extruder, 1.0% weight percent of NatureWorks Grade 6302 2% by weight was combined with NatureWorks Grade 6752 to provide the sheath of bicomponent fabric. The fabric of Comparative Sample 4 was made at processing conditions similar to those used for Inventive Examples 1-4 except as shown in Table 8, below, and the line speed was adjusted to provide a final basis weight of 25 GSM. Properties of Comparative Example 5 are summarized below in Table 9.

Comparative Example 6

In Comparative Example 6 a 100% PLA bicomponent fabric having a sheath/core arrangement was prepared in which 2.0% weight percent of NatureWorks Grade 6302 was added to the polymer component defining the sheath. The setup of the system is the same as described above for Comparative Examples 1, 2, and 3.

The fabric was a bicomponent 30/70 NatureWorks Grade 6752/NatureWorks Grade 6202/sheath/core made with ionization bars as discussed above to minimize static. At the sheath extruder, 2.0% weight percent of NatureWorks Grade 6302 2% by weight was combined with NatureWorks Grade 6752 to provide the sheath of bicomponent fabric. The fabric of Comparative Example 6 was made at processing conditions similar to those used for Inventive Examples 1-4 except as shown in Table 8, below, and the line speed was adjusted to provide a final basis weight of 25 GSM. Properties of Comparative Example 6 are summarized below in 9, below.

Comparative Example 7

In Comparative Example 7 a 100% PLA bicomponent fabric having a sheath/core arrangement was prepared in which 3.5% weight percent of NatureWorks Grade 6302 was added to the polymer component defining the sheath. The setup of the system is the same as described above for Comparative Examples 1, 2, and 3.

The fabric was a bicomponent 30/70 NatureWorks Grade 6752/NatureWorks Grade 6202/sheath/core made with ionization bars as discussed above to minimize static. At the sheath extruder, 3.5% weight percent of NatureWorks Grade 6302 2% by weight was combined with NatureWorks Grade 6752 to provide the sheath of bicomponent fabric. The fabric of Comparative Sample 7 was made at processing conditions similar to those used for Examples of this invention 1-4 except as shown in Table 8, below, and the line speed was adjusted to provide a final basis weight of 25 GSM. Properties of Comparative Sample 7 are summarized below in Table 9, below.

Inventive Example 5

In Inventive Example 5, a 100% PLA bicomponent fabric having a sheath/core arrangement was prepared in which 0.3 weight percent of a masterbatch comprising a PLA resin and a secondary alkane sulfonate was added to the polymer component defining the sheath. The setup of the system is the same as described above for Comparative Examples 1, 2, and 3.

The fabric was a bicomponent 50/50 NatureWorks Grade 6752/NatureWorks Grade 6202/sheath/core made with ionization bars as discussed above to minimize static. At the sheath extruder, 0.3% by weight of a masterbatch of Sukano Product S 546 was combined with NatureWorks Grade 6752 to provide the sheath of bicomponent fabric. The fabric of Inventive Example 5 was produced was made at processing conditions similar to those used for Inventive Examples 1-4 except as shown in Table 8, below, and the line speed was adjusted to provide a final basis weight of 28 GSM. Properties of Inventive Example 5 are summarized below in Table 9, below.

Inventive Example 6

In Inventive Example 5, a 100% PLA bicomponent fabric having a sheath/core arrangement was prepared in which 0.3 weight percent of a masterbatch comprising a PLA resin and a secondary alkane sulfonate was added to the polymer component defining the sheath. The setup of the system is the same as described above for Inventive Examples 1, 2, and 3.

The fabric was a bicomponent 50/50 NatureWorks Grade 6752/NatureWorks Grade 6202/sheath/core made with ionization bars as discussed above to minimize static. At the sheath extruder, 0.3% by weight of a masterbatch of Sukano Product S 546 was combined with NatureWorks Grade 6752 to provide the sheath of bicomponent fabric. The fabric of Inventive Example 6 was produced was made at processing conditions similar to those used for Inventive Examples 1-4 except as shown in Table 8 below, and the line speed was adjusted to provide a final basis weight of 23 GSM. Properties of Inventive Example 6 are summarized below in Table 9, below.

TABLE 8

Process Conditions for Comparative Examples 4-7 and Inventive Examples 5-6

| Example | Through-Put | Cabin Pressure | Calender Temperature (Embossed/Smooth) Units | Calender Pressure | Gap |
|---|---|---|---|---|---|
| | Kg/hr | Pa | C./C. | N/mm | Setting |
| Comparative Example 4 | 230 | 6000 | 165/140 | 40 | 22/26 |
| Comparative Example 5 | 230 | 6000 | 165/140 | 40 | 22/26 |
| Comparative Example 6 | 230 | 6000 | 165/140 | 40 | 22/26 |
| Comparative Example 7 | 230 | 6000 | 165/140 | 40 | 22/26 |
| Inventive Example 5 | 240 | 6500 | 152/142 | 40 | 20/24 |
| Inventive Example 6 | 240 | 6500 | 152/142 | 40 | 20/24 |

TABLE 9

Mechanical Properties

| Example | Titer | Basis Weight | MD Tensile | MD Tensile per Basis Weight | CD Tensile | CD Tensile per Basis Weight | M % Elong. | CD % Elong. | MD Toughness Index | CD Toughness Index | MD Toughness Index per BW | CD Toughness Index per BW |
|---|---|---|---|---|---|---|---|---|---|---|---|---|
| | DTEX | g/m$^2$ | N/5 cm | N-m$^2$/g-5 cm | N/5 cm | N-m$^2$/g-5 cm | % | % | N-% | N-% | N-%/gsm | N-%/gsm |
| Comparative Example 4 | 1.8 | 23.12 | 38.97 | 1.69 | 13.85 | 0.599 | 14.75 | 25.33 | 574.81 | 477.47 | 24.86 | 20.65 |
| Comparative Example 5 | No Data | 28.37 | 35.33 | 1.24 | 12.59 | 0.444 | 13.17 | 24.39 | 465.30 | 307.07 | 16.40 | 10.82 |
| Comparative Example 6 | No Data | 22.62 | 34.87 | 1.54 | 12.15 | 0.537 | 13.21 | 24.56 | 460.63 | 298.40 | 20.36 | 13.19 |
| Comparative Example 7 | No Data | 23.38 | 34.24 | 1.46 | 12.94 | 0.553 | 12.58 | 26.79 | 430.74 | 346.67 | 18.42 | 14.83 |
| Inventive Example 5 | 2.40 | 28.37 | 69.48 | 2.45 | 20.96 | 0.739 | 23.64 | 32.32 | 1642.51 | 677.43 | 57.90 | 23.88 |

TABLE 9-continued

Mechanical Properties

| | Titer | Basis Weight | MD Tensile | MD Tensile per Basis Weight | CD Tensile | CD Tensile per Basis Weight | M % Elong. | CD % Elong. | MD Toughness Index | CD Toughness Index | MD Toughness Index per BW | CD Toughness Index per BW |
|---|---|---|---|---|---|---|---|---|---|---|---|---|
| | | | | Units | | | | | | | | |
| Example | DTEX | g/m² | N/5 cm | N-m²/g-5 cm | N/5 cm | N-m²/g-5 cm | % | % | N-% | N-% | N-%/gsm | N-%/gsm |
| Inventive Example 6 | 2.07 | 23.12 | 52.93 | 2.89 | 15.43 | 0.667 | 25.18 | 32.79 | 1332.78 | 505.95 | 57.65 | 21.88 |

There was no visible difference in the bonding sites for nonwovens fabrics above (Comparative Examples 4-7) made with PLA 6302 used as an additive versus nonwovens above made using addition of the masterbatch of Sukano Product 546 (Inventive Examples 5 and 6). However, as from the mechanical data summarized in Table 9, a significant difference between the Comparative Examples and Inventive Examples 5 and 6 was observed. In particular, the examples including secondary alkane sulfonate exhibited significant improvements in MD and CD tensile strength, MD and CD elongation, and MD and CD Toughness Index in comparison to the comparative examples that only include the masterbatch PLA resin, but no secondary alkane sulfonate. Accordingly, it can be seen that the improvement in properties are attributed to the presence of the secondary alkane sulfonate, and not to the lower molecular weight PLA resin of the masterbatch.

It was also observed that during the manufacture of the fabrics, the fabrics of Inventive Examples 5 and 6 were more stable during calender bonding calender in comparison to the fabrics of Comparative Examples 4-7.

In the following examples, the hydrophilic nature of the PLA fabrics, and the effects of the secondary alkane sulfonate on the hydrophilicity of the fabrics were investigated. Inventive Examples 7-12 were prepared in accordance with the fabric of Inventive Fabrics 6 and 7. In each example, the amount of Sukano additive added to the sheath was varied and the effects on liquid Run-Off and Strike-through was evaluated at different time periods. The results are summarized in Tables 10 and 11, below.

Run-Off data was measured in accordance with the procedures set forth in WSP 80.9, and Strikethrough data as measured by test method WSP 70.3.

Runoff data measures the percent of a specified volume of fluid that runs off a fabric/absorbent combination that is supported at a specified angle from vertical. The fabric being evaluated is positioned overlying an absorbent material. During the test procedure, a fluid runs down the fabric and may, or may not, be absorbed into the absorbent material placed under the fabric being tested. If the fabric is hydrophobic a very high % of the fluid runs down and off the fabric/absorbent combination into a container for collection. If the fabric is very hydrophilic nearly all of the liquid is absorbed by the fabric/absorbent combination and the % Run-off is nearly equal to zero. The Runoff test is commonly repeated on the same piece of fabric three times. This procedure simulates multiple voids by the baby or adult into the diaper. Most typical commercial topsheets show a very low % run-off in the first insult. However the Run-off values commonly increases in the second and third insults as the surfactant is washed off and transported into the absorbent material under the test fabric. Thus, all hydrophilic surfactant may be lost following a first voiding. As a result, repeated voidings by a wearer, such as a baby, may result in loss of hydrophilicity of the fabric, which may undesirably lead to leakage of the diaper.

Strike Through data measures the time for a specified volume of liquid applied at downward at a 90 degree angle to the a test fabric surface that is backed by an absorbent layer. The strike though values after one or multiple insults can be measured. A low strike through value suggests that liquid will rapidly penetrate the hydrophilic treated fabric and be absorbed by the absorbent material simulated the core of the diaper. Results after multiple strike through tests provide an indication of the permanence of the surfactant treatment. Increasing values of strikethrough with multiple insults suggests that the surfactant is being washed into the underlying absorbent material, such as an absorbent core, with risk that the diaper topsheet will become hydrophobic and the diaper will leak. An optimized topsheet will provide strikethrough values of 4 seconds or less even after up to three insults.

TABLE 10

Run-Off Test Results

| Example | Sukano Additive Level % | % Run-Off Tested Fresh as Made First Gush | % Run-Off Tested 24 Hours after Made First Gush | % Run Off Tested 14 days after Made First Gush | % Run Off Tested 14 days after Made Second Gush | % Run Off Tested 14 days after Made Third Gush | % Run Off 30 days after Made First Gush | % Run Off 30 days after Made Second Gush | % Run Off 30 days after Made Third Gush |
|---|---|---|---|---|---|---|---|---|---|
| Example 7 | 0.25% | 98.6 | 99.5 | 96.36 | 96.16 | 96.92 | 98.85 | 92.20 | 86.48 |
| Example 8 | 0.5% | 98.3 | 98.8 | 95.88 | 96.08 | 95.36 | 98.97 | 98.20 | 98.99 |
| Example 9 | 1.0% | 98.4 | 97.6 | — | — | — | 98.01 | 6.87 | 2.15 |
| Example 10 | ..5% | 98.4 | 98.3 | — | — | — | 97.15 | 0.00 | 0.11 |
| Example 11 | 2% | 98.0 | 97.7 | — | — | — | 95.79 | 0.00 | 0.00 |
| Example 12 | 2.5% | 93.0 | 89.4 | — | — | — | 72.91 | 0.00 | 0.00 |

TABLE 11

Strike-through Test Results

| Example | Sukano Additive Level % | Strike-Through (Sec.) Tested Fresh as Made First Gush | Strike-Through (Sec.) Tested 24 Hours after Made First Gush | Strike-Through (Sec.) Tested 14 days after Made First Gush | Strike-Through (Sec.) Tested 14 days after Made Second Gush | Strike-Through (Sec.) Tested 14 days after Made Third Gush | Strike-Through (Sec.) 30 days after Made First Gush | Strike-Through (Sec.) 30 days after Made Second Gush | Strike-Through (Sec.) 30 days after Made Third Gush |
|---|---|---|---|---|---|---|---|---|---|
| Example 7 | 0.25% | 8.2 | 9.3 | 4.95 | 4.86 | 4.43 | 8.34 | 5.43 | 5.03 |
| Example 8 | 0.5% | 8.6 | 8.4 | 6.09 | 4.42 | 3.58 | 4.65 | 3.70 | 3.28 |
| Example 9 | 1.0% | 9.6 | 8.6 | — | — | — | 5.15 | 1.95 | 2.30 |
| Example 10 | 1.5% | 5.9 | 5.5 | — | — | — | 4.08 | 1.90 | 2.38 |
| Example 11 | 2% | 4.4 | 4.3 | — | — | — | 3.35 | 1.90 | 2.16 |
| Example 12 | 2.5% | 2.9 | 3.4 | — | — | — | 1.88 | 2.00 | 2.18 |

The % Run-Off and Strike-Through Data in Tables 10 and 11 surprisingly demonstrated that not only does the secondary alkane sulfonate improve the mechanical properties of the PLA fabric, but it also modifies the liquid transport properties of the fabrics.

In addition, the results demonstrate that the Run-Off and Strike-through are dependent, at least in part, on the level of the secondary alkane sulfonate as well as age of the fabric. For example, at two weeks 100% PLA fabric containing 0.25% and 0.5% of the additive exhibited hydrophobic properties as measured by both runoff and strikethrough. After a month following production, the fabrics containing 0.25% and 0.5% of the additive still exhibited hydrophobic properties. However, at higher additive levels a response is observed suggestive of decreasing hydrophobicity. Surprising and unexpected, the response is opposite to that seen with typical surfactant treated topsheet. Initial runoff and strikethrough suggests a hydrophobic fabric. However, following the second and third insults, the fabric exhibits hydrophilic properties.

This effect suggests that fabrics in accordance with the invention may be prepared that provide hydrophilic properties following multiple voids. In particular, fabrics for use as a topsheet may be prepared in which the fabric is treated with a low add-on surfactant to provide initial hydrophilicity, but then takes advantage of the additive to provide a wash-off resistant hydrophilicity after multiple insults. Such a topsheet may be of particular interest for use in overnight diapers and incontinent products.

Non-Limiting Exemplary Embodiments

Having described various aspects and embodiments of the invention herein, further specific embodiments of the invention include those set forth in the following paragraphs.

Certain embodiments according to the invention are directed to a spunbond nonwoven fabric comprising a plurality of fibers that are bonded to each other to form a coherent web, wherein the fibers comprise a blend of a polylactic acid (PLA) and at least one secondary alkane sulfonate. In some embodiments, the blend is present at a surface of the plurality of fibers. In one embodiment, the at least one secondary alkane sulfonate comprises an alkane chain having from $C_{10}$-$C_{18}$, and wherein at least one of the secondary carbons of the alkane chain includes a sulfonate moiety. For example, the at least one secondary alkane sulfonate has one of the following structures:

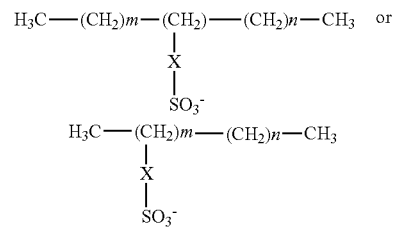

wherein m+n is a number between 7 and 16, and X is independently a $C_1$-$C_4$ alkyl or absent. In some embodiments, the at least one secondary alkane sulfonate has the following structure:

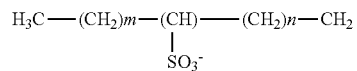

wherein m+n is a number between 8 and 15, and in particular, wherein m+n is a number between 11 and 14. In some embodiments, the at least one secondary alkane sulfonate comprises a salt of sodium or potassium.

In certain embodiments, the at least one secondary alkane sulfonate is present in an amount ranging from about 0.0125 to 2.5 weight percent, based on the total weight of the fiber. For example, the fiber may have a sheath/core bicomponent arrangement in which the blend is present in the sheath, and wherein the secondary alkane sulfonate is present in the sheath in an amount ranging from about 0.1 to 0.75 weight percent, based on the total weight of the sheath. In another embodiment, the fiber may have a sheath/core bicomponent arrangement in which the blend is present in the sheath, and wherein the secondary alkane sulfonate is present in the sheath in an amount ranging from about 0.2 to 0.6 weight percent, based on the total weight of the sheath. In yet another embodiment, the fiber has a sheath/core bicomponent arrangement in which the blend is present in the sheath, and wherein the secondary alkane sulfonate is present in the sheath in an amount ranging from about 0.3 to 0.4 weight percent, based on the total weight of the sheath.

In one embodiment, the plurality of fibers comprise bicomponent fibers. In some embodiments, the plurality of fibers comprise bicomponent fibers and the at least one secondary alkane sulfonate is present in only one of the component of the fibers. In one embodiment, the bicomponent fibers have a sheath/core configuration and the sheath comprises a blend of the PLA and the at least one secondary alkane sulfonate. In some embodiments, the core comprises PLA and does not include the at least one secondary alkane sulfonate. In still other embodiments, the bicomponent fibers comprise a side-by-side arrangement.

In one embodiment, the core comprises at least one of a polyolefin, a polyester, a PLA, or any combination thereof. In a preferred embodiment, each of the sheath and the core comprises PLA. In certain embodiments, the sheath comprises a first PLA grade, the core comprises a second PLA grade, and the first PLA grade and the second PLA grade are different.

In some embodiments, the fabric exhibits an increase in tensile strength in at least one of the machine direction or cross direction in comparison to an identical fabric that does not include the at least one secondary alkane sulfonate. For example, the fabric may exhibit an increase in tensile strength in at least one of the machine direction or cross direction of at least 50% in comparison to an identical fabric that does not include the at least one secondary alkane sulfonate.

In one embodiment, the fabric exhibits an increase in tensile strength in at least one of the machine direction or cross direction that is from 50% to 200% in comparison to an identical fabric that does not include the at least one secondary alkane sulfonate.

In one embodiment, the fabric exhibits an increase in machine direction tensile strength that is from about 50 to 150% in comparison to an identical fabric that does not include the at least one secondary alkane sulfonate.

In one embodiment, the fabric exhibits an increase in machine direction tensile strength that is from about 55 to 125% in comparison to an identical fabric that does not include the at least one secondary alkane sulfonate.

In one embodiment, the fabric exhibits an increase in machine direction tensile strength that is from about 65 to 110% in comparison to an identical fabric that does not include the at least one secondary alkane sulfonate.

In one embodiment, the fabric exhibits an increase in machine direction tensile strength that is from about 65 to 110% in comparison to an identical fabric that does not include the at least one secondary alkane sulfonate.

In one embodiment, the fabric exhibits an increase in machine direction tensile strength that is from about 85 to 110% in comparison to an identical fabric that does not include the at least one secondary alkane sulfonate.

In one embodiment, the fabric exhibits an increase in machine direction tensile strength that is from about 90 to 110% in comparison to an identical fabric that does not include the at least one secondary alkane sulfonate.

In one embodiment, the fabric exhibits an increase in cross direction tensile strength that is from about 50 to 200% in comparison to an identical fabric that does not include the at least one secondary alkane sulfonate.

In one embodiment, the fabric exhibits an increase in cross direction tensile strength that is from about 50 to 170% in comparison to an identical fabric that does not include the at least one secondary alkane sulfonate.

In one embodiment, the fabric exhibits an increase in cross direction tensile strength that is from about 55 to 165% in comparison to an identical fabric that does not include the at least one secondary alkane sulfonate.

In one embodiment, the fabric exhibits an increase in cross direction tensile strength that is from about 65 to 160% in comparison to an identical fabric that does not include the at least one secondary alkane sulfonate.

In one embodiment, the fabric exhibits an increase in cross direction tensile strength that is from about 85 to 150% in comparison to an identical fabric that does not include the at least one secondary alkane sulfonate.

In one embodiment, the fabric exhibits an increase in cross direction tensile strength that is from about 90 to 125% in comparison to an identical fabric that does not include the at least one secondary alkane sulfonate.

In one embodiment, the fabric exhibits an increase in elongation in at least one of the machine direction or cross direction in comparison to an identical fabric that does not include the at least one secondary alkane sulfonate.

In one embodiment, the fabric exhibits a machine direction Index of Toughness that is from about 2,000 to 7,500 N-%.

In one embodiment, the fabric exhibits a machine direction Index of Toughness that is from about 2,300 to 6,500 N-%.

In one embodiment, the fabric exhibits a machine direction Index of Toughness that is from about 2,300 to 6,000 N-%.

In one embodiment, the fabric exhibits a cross direction Index of Toughness that is from about 1,000 to 5,000 N-%.

In one embodiment, the fabric exhibits a cross direction Index of Toughness that is from about 1,250 to 5,000 N-%.

In one embodiment, the fabric exhibits a cross direction Index of Toughness that is from about 1,250 to 3,500 N-%.

In one embodiment, the fabric exhibits an increase in machine direction Index of Toughness that is from about 20 to 1,250% in comparison to an identical fabric that does not include the at least one secondary alkane sulfonate.

In one embodiment, the fabric exhibits an increase in machine direction Index of Toughness that is at least 100% in comparison to an identical fabric that does not include the at least one secondary alkane sulfonate.

In one embodiment, the fabric exhibits an increase in cross direction Index of Toughness that is from about 50 to 1,000% in comparison to an identical fabric that does not include the at least one secondary alkane sulfonate.

In one embodiment, the fabric exhibits an increase in cross direction Index of Toughness that is at least 85% in comparison to an identical fabric that does not include the at least one secondary alkane sulfonate.

In some embodiments, the fabric exhibits a machine direction Relative Index of Toughness that is from about 50 to 150 N-%/g/m$^2$, such as a machine direction Relative Index of Toughness that is from about 75 to 125 N-%/g/m$^2$, and in particular, a machine direction Relative Index of Toughness that is from about 85 to 115 N-%/g/m$^2$. In one embodiment, the fabric exhibits a cross direction Relative Index of Toughness that is from about 40 to 100 N-%/g/m$^2$, such as a cross direction Relative Index of Toughness that is from about 45 to 85 N-%/g/m$^2$.

In certain embodiments, the fabric exhibits an increase in machine direction Relative Index of Toughness that is from about 100 to 1,000% in comparison to an identical fabric that does not include the at least one secondary alkane sulfonate, such as an increase in machine direction Relative Index of Toughness that is from 80 to 500% in comparison to an identical fabric that does not include the at least one secondary alkane sulfonate.

In one embodiment, the fabric exhibits an increase in cross direction Relative Index of Toughness that is at least 100% in comparison to an identical fabric that does not include the at least one secondary alkane sulfonate, such as an increase in cross direction Relative Index of Toughness that is from about 140 to 410% in comparison to an identical fabric that does not include the at least one secondary alkane sulfonate.

Additional aspects of the invention are directed to a spunbond nonwoven fabric comprising a plurality of fibers that are bonded to each other to form a coherent web, wherein the fibers comprise from 95 to 100% polylactic acid (PLA), and wherein the fibers exhibit a root mean square of a Toughness Index per basis weight having a value that is at least 55 N-%/g/m$^2$. In one such embodiment, the root mean square of the Toughness Index per basis weight is a value that is greater than 65 N-%/g/m$^2$, such as a value from about from about 65 to 150 N-%/g/m$^2$. In one embodiment, the fibers of the fabric comprise less than 5 weight % of additives.

Aspects of the invention are also directed to absorbent articles comprising a nonwoven fabric having fibers comprising a blend of a PLA resin and at least one secondary alkane sulfonate. Examples of absorbent articles include diapers and feminine sanitary pads.

Additional aspects of the invention are directed to a process for preparing a polylactic acid (PLA) spunbond nonwoven fabric, the process comprising: blending a PLA resin and at least one secondary alkane sulfonate, under heat and pressure, to form a stream of molten or semi-molten PLA resin; forming a plurality of PLA continuous filaments from said stream; depositing the plurality of PLA continuous filaments onto a collection surface; exposing the plurality of PLA continuous filaments to ions; and bonding the plurality of PLA continuous filaments to form the PLA spunbond nonwoven fabric, wherein the continuous filaments comprise a blend of PLA and the at least one secondary alkane sulfonate.

In one embodiment, the filaments comprise a blend of PLA and the at least on secondary alkane sulfonate. The filaments may be monocomponent or bicomponent. In a preferred embodiment, the filaments have a sheath/core bicomponent configuration in which the sheath comprises the blend of the PLA and the at least one secondary alkane sulfonate. In some embodiments, the core may comprise PLA or a synthetic polymer, such as a polyolefin or a polyester. Preferably, the core comprises PLA.

Advantageously, the process may be performed at relatively high draw speeds. For example, the continuous filaments may be drawn at a fiber draw speed greater than about 2500 m/min., such as a fiber draw speed from about 3000 m/min to about 5500 m/min., or a fiber draw speed from about 3000 m/min to about 4000 m/min.

In one embodiment, the step of exposing the plurality of PLA continuous filaments to ions comprising passing the filaments in close proximity to an ionization source, such as an ionization bar. In one embodiment, the ionization source comprises an ionization bar that is positioned above the collection surface, and in the cross direction of the fabric.

In one embodiment, the step of bonding the continuous filaments to form the PLA spunbond nonwoven fabric comprises thermal point bonding the web with heat and pressure via a calender having a pair of cooperating rolls including a patterned roll. In some embodiments, the thermal point bonding the continuous filaments comprises imparting a three-dimensional geometric bonding pattern onto the PLA spunbond nonwoven fabric.

In one embodiment, the bonding of the pattern onto the PLA spunbond nonwoven fabric comprises imparting at least one of a diamond pattern, a hexagonal dot pattern, an oval-elliptic pattern, a rod-shaped pattern, or any combination thereof onto the PLA spunbond nonwoven fabric. In some embodiments, the bonding pattern covers from about 5% to about 30% of the surface area of the patterned roll. For example, the bonding pattern may cover from about 10% to about 25% of the surface area of the patterned roll.

In one embodiment, the process additionally comprises dissipating static charge from the PLA spunbond nonwoven fabric proximate to the calender via a first static control unit. In one embodiment, the static control unit comprises a second ionization source, such as an ionization bar. For instance, the second ionization source may comprise an ionization bar extending over at least one of the plurality of PLA continuous filaments or the PLA spunbond nonwoven fabric in a cross direction.

In one embodiment, dissipating static charge from the PLA spunbond nonwoven fabric comprises contacting the PLA spunbond nonwoven fabric with a static bar.

In some embodiments, the process may further comprise cutting the PLA spunbond nonwoven fabric to form cut PLA spunbond nonwoven fabric; exposing the cut PLA spunbond nonwoven fabric to ions via a third ionization source; and winding the cut PLA spunbond nonwoven fabric into rolls. In one embodiment, the third ionization source comprises an ionization bar extending over at least one of the plurality of PLA continuous filaments or the PLA spunbond nonwoven fabric in a cross direction.

Additional aspects of the invention are directed to a system for preparing a polylactic acid (PLA) spunbond nonwoven fabric, the system comprising: a first PLA source and a source of a secondary alkane sulfonate, configured to provide a stream comprising molten or semi-molten PLA resin and the secondary alkane sulfonate; a spin beam in fluid communication with the first PLA source, the spin beam configured to extrude and draw a plurality of PLA continuous filaments, wherein the PLA continuous filaments comprise a blend of the PLA and the secondary alkane sulfonate; a collection surface disposed below an outlet of the spin beam onto which the PLA continuous filaments are deposited to form the PLA spunbond nonwoven fabric; a first ionization source positioned and arranged to expose the PLA continuous filaments to ions; and a calender positioned downstream of the first ionization source.

In one embodiment, the first ionization source is positioned above the collection surface and downstream of a point at where the PLA continuous filaments are deposited on the collection surface. In another embodiment, the first ionization source is positioned between the outlet of the spin beam and the collection surface. Preferably, the first ionization source and the collection surface are separated by a distance from about 1 inch to about 24 inches, such as a distance from about 1 inch to about 12 inches, and in particular, a distance from about 1 inch to about 5 inches.

In some embodiments, the system may further comprise a static control unit positioned and arranged to dissipate static from the PLA spunbond nonwoven fabric proximate to the calender. In one embodiment, the static control unit comprises a passive static bar, or a second ionization source, or a combination thereof.

In one embodiment, the system includes a press roll positioned downstream from the outlet of the spin beam. In some embodiments, the system may comprise a vacuum source disposed below the collection surface.

In certain embodiments, the system may include a winder positioned downstream from the calender; and a third ionization source positioned and arranged to expose the PLA spunbond nonwoven fabric to ions proximate to the winder.

In one embodiment, the at least one of the first ionization source, the static control source, and the third ionization source each comprise an ionization bar extending over at least one of the plurality of PLA continuous filaments or the PLA spunbond nonwoven fabric in a cross direction. In one embodiment, the first ionization source, the static control source, and the third ionization source are configured to actively dissipate static charge created during preparation of the PLA spunbond nonwoven fabric.

In one embodiment, the first ionization source is positioned downstream from the press roll. In some embodiments, the first ionization source is positioned between the spin beam and the press roll. When present, the static control unit may be positioned upstream from, and adjacent to, the calender. In other embodiments, the static control unit is positioned downstream from, and adjacent to, the calender.

In one embodiment, the calender comprises a pair of cooperating rolls including a patterned roll, the patterned roll comprising a three-dimensional geometric bonding pattern. In some embodiments, the bonding pattern comprises at least one of a diamond pattern, a hexagonal dot pattern, an oval-elliptic pattern, a rod-shaped pattern, or any combination thereof. In one embodiment, the bonding pattern covers from about 5% to about 30% of the surface area of the patterned roll, such as from about 10% to about 25% of the surface area of the patterned roll.

In one embodiment, the system is configured to produce a nonwoven fabric of continuous filaments having a bicomponent arrangement. In one embodiment, the continuous filaments have a sheath/core arrangement. In a preferred embodiment, the system is configured to produce filaments in which the blend of the PLA and the secondary alkane sulfonate defines the sheath. In some embodiments, the core comprises a PLA resin. The PLA resin may be the same or different than that of the sheath. In one embodiment, the core is free of the secondary alkane sulfonate.

In some embodiments, the secondary alkane sulfonate is present in an amount ranging from about 0.0125 to 2.5 weight percent, based on the total weight of the fiber. In one embodiment, the continuous filaments have a sheath/core bicomponent arrangement in which the blend is present in the sheath, and wherein the secondary alkane sulfonate is present in the sheath in an amount ranging from about 0.1 to 0.75 weight percent, based on the total weight of the sheath.

In one particular embodiment, the system is configured to prepare continuous filaments having a sheath/core bicomponent in which the blend is present in the sheath, and wherein the secondary alkane sulfonate is present in the sheath in an amount ranging from about 0.2 to 0.6 weight percent, based on the total weight of the sheath. In other embodiments, the system is configured to produce continuous filaments having a sheath/core bicomponent arrangement in which the blend is present in the sheath, and wherein the secondary alkane sulfonate is present in the sheath in an amount ranging from about 0.3 to 0.4 weight percent, based on the total weight of the sheath.

Modifications of the invention set forth herein will come to mind to one skilled in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A spunbond nonwoven fabric comprising a plurality of fibers that are bonded to each other to form a coherent web, wherein the fibers comprise a blend of a polylactic acid (PLA) and at least one secondary alkane sulfonate, wherein the at least one secondary alkane sulfonate is present in an amount ranging from 0.00375 to 0.2 weight percent, based on the total weight of the fiber, and wherein the fabric exhibits at least one of the following:

an increase in tensile strength in at least one of the machine or cross direction in comparison to an identical fabric that does not include the at least one secondary alkane sulfonate; and an increase in elongation in at least one of the machine direction or cross direction in comparison to an identical fabric that does not include the at least one secondary alkane sulfonate.

2. The fabric of claim 1, wherein the blend is present at a surface of the plurality of fibers.

3. The fabric of claim 1, wherein the at least one secondary alkane sulfonate comprises an alkane chain having from $C_{10}$-$C_{18}$, and wherein at least one of the secondary carbons of the alkane chain includes a sulfonate moiety.

4. The fabric of claim 1, wherein the at least one secondary alkane sulfonate has one of the following structures:

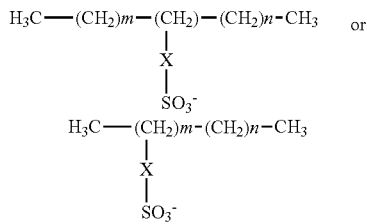

wherein m+n is a number between 7 and 16, and X is independently a $C_1$-$C_4$ alkyl or absent.

5. The fabric of claim 1, wherein the at least one secondary alkane sulfonate has the following structure:

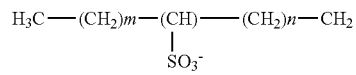

wherein m+n is a number between 8 and 15.

6. The fabric of claim 1, wherein the at least one secondary alkane sulfonate comprises a salt of sodium or potassium.

7. The fabric of claim 1, wherein the at least one secondary alkane sulfonate is present in an amount ranging from about 0.0125 to 0.15 weight percent, based on the total weight of the fiber.

8. The fabric of claim 1, wherein the fiber has a sheath/core bicomponent arrangement in which the blend is present in the sheath, and wherein the secondary alkane sulfonate is present in the sheath in an amount ranging from about 0.1 to 0.1875 weight percent, based on the total weight of the sheath.

9. The fabric of claim 1, wherein plurality of fibers comprise bicomponent fibers.

10. The fabric of claim 9, wherein the bicomponent fibers have a sheath/core configuration and each of the sheath and the core comprises PLA.

11. The fabric of claim 1, wherein plurality of fibers comprise bicomponent fibers and the at least one secondary alkane sulfonate is present in only one of the component of the fibers.

12. The fabric of claim 11, wherein the bicomponent fibers have a sheath/core configuration and the sheath comprises said blend of the PLA and the at least one secondary alkane sulfonate.

13. The fabric of claim 1, wherein the fabric exhibits a machine direction Index of Toughness that is from about 2,000 to 7,500 N-%.

14. An absorbent article comprising the fabric of claim 1.

15. The absorbent article of claim 14, wherein the article comprises a diaper or a sanitary pad.

16. The fabric of claim 1, wherein the at least one secondary alkane sulfonate has the following structure:

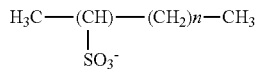

wherein n is a number between 7 and 16.

17. The fabric of claim 1, wherein the fiber has a sheath/core configuration in which the at least one secondary alkane sulfonate is present only in the sheath, and wherein the amount of the at least one secondary alkane sulfonate in the sheath is from 0.0125 to 0.2 weight percent, based on the total weight of the sheath.

18. A process for preparing a polylactic acid (PLA) spunbond nonwoven fabric, the process comprising:
  blending a PLA resin and at least one secondary alkane sulfonate, under heat and pressure, to form a stream of molten or semi-molten PLA resin;
  forming a plurality of PLA continuous filaments from said stream;
  depositing the plurality of PLA continuous filaments onto a collection surface; and
  bonding the plurality of PLA continuous filaments to form the PLA spunbond nonwoven fabric as recited in claim 1, wherein the continuous filaments comprise a blend of PLA and the at least one secondary alkane sulfonate, and wherein the at least one secondary alkane sulfonate is present in the blend an amount ranging from 0.00375 to 0.2 weight percent, based on the total weight of the filaments.

19. The process of claim 18, wherein the at least one secondary alkane sulfonate has the following structure:

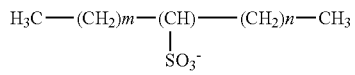

wherein m+n is a number between 8 and 15.

20. The process of claim 18, wherein forming the plurality of PLA continuous filaments comprises forming bicomponent fibers having a side-by-side or sheath/core orientation.

21. The process of claim 20, wherein the sheath comprises the blend of PLA and the at least one secondary alkane sulfonate.

22. The process of claim 18 further comprising a step of exposing the plurality of PLA continuous filaments to ions.

23. A system for preparing a polylactic acid (PLA) spunbond nonwoven fabric of claim 1, the system comprising:
  a first PLA source and a source of a secondary alkane sulfonate, configured to provide a stream comprising molten or semi-molten PLA resin and the secondary alkane sulfonate;
  a spin beam in fluid communication with the first PLA source, the spin beam configured to extrude and draw a plurality of PLA continuous filaments, wherein the PLA continuous filaments comprise a blend of the PLA and the secondary alkane sulfonate, and the at least one secondary alkane sulfonate is present in the blend an amount ranging from 0.00375 to 0.2 weight percent, based on the total weight of the filament;
  a collection surface disposed below an outlet of the spin beam onto which the PLA continuous filaments are deposited to form the PLA spunbond nonwoven fabric; and
  a calender positioned downstream of the spin beam.

24. The system of claim 23, wherein secondary alkane sulfonate has the following structure:

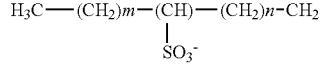

wherein m+n is a number between 8 and 15.

* * * * *